(12) United States Patent
Wu et al.

(10) Patent No.: US 11,771,366 B2
(45) Date of Patent: Oct. 3, 2023

(54) METHOD, APPARATUS, AND SYSTEM FOR RADIO BASED SLEEP TRACKING

(71) Applicants: Chenshu Wu, Hong Kong (CN); Beibei Wang, Clarksville, MD (US); Oscar Chi-Lim Au, San Jose, CA (US); Hung-Quoc Duc Lai, Parkville, MD (US); K. J. Ray Liu, Potomac, MD (US)

(72) Inventors: Chenshu Wu, Hong Kong (CN); Beibei Wang, Clarksville, MD (US); Oscar Chi-Lim Au, San Jose, CA (US); Hung-Quoc Duc Lai, Parkville, MD (US); K. J. Ray Liu, Potomac, MD (US)

(73) Assignee: ORIGIN WIRELESS, INC., Rockville, MD (US)

( * ) Notice: Subject to any disclaimer, the term of this patent is extended or adjusted under 35 U.S.C. 154(b) by 0 days.

(21) Appl. No.: 17/888,429

(22) Filed: Aug. 15, 2022

(65) Prior Publication Data
US 2022/0386945 A1    Dec. 8, 2022

Related U.S. Application Data

(63) Continuation-in-part of application No. 16/790,610, filed on Feb. 13, 2020, and a continuation-in-part of
(Continued)

(51) Int. Cl.
  *A61B 5/00*    (2006.01)
  *A61B 5/11*    (2006.01)
  *A61B 5/0507*  (2021.01)

(52) U.S. Cl.
  CPC ......... *A61B 5/4809* (2013.01); *A61B 5/0507* (2013.01); *A61B 5/1116* (2013.01); *A61B 5/7264* (2013.01)

(58) Field of Classification Search
  CPC combination set(s) only.
  See application file for complete search history.

(56) References Cited

U.S. PATENT DOCUMENTS

2014/0179340 A1*  6/2014  Do ..................... G01S 5/021
                                              455/456.1

OTHER PUBLICATIONS

Liu et al., "Tracking Vital Signs During Sleep Leveraging Off-the-shelf WiFi", Jun. 2015, ACM, pp. 267-276 (Year: 2015).*
(Continued)

*Primary Examiner* — Zhiyu Lu

(57) ABSTRACT

Methods, apparatus and systems for radio-based sleep tracking are described. In one example, a described system comprises: a transmitter configured to transmit a first wireless signal through a wireless multipath channel in a venue; a receiver configured to receive a second wireless signal through the wireless multipath channel, wherein the second wireless signal differs from the first wireless signal due to the wireless multipath channel which is impacted by a sleeping motion of an object in the venue; and a processor. The processor is configured for: obtaining a time series of channel information (TSCI) of the wireless multipath channel based on the second wireless signal, wherein each channel information (CI) of the TSCI comprises N1 components, wherein N1 is a positive integer larger than one, computing N1 component-wise analytics each associated with one of the N1 components of the TSCI, identifying N2 largest component-wise analytics among the N1 component-wise analytics, wherein N2 is a positive integer less than N1, computing at least one first motion statistics based on the N2 largest component-wise analytics of the TSCI, and monitoring the sleeping motion of the object based on the at least one first motion statistics.

26 Claims, 11 Drawing Sheets

Related U.S. Application Data application No. 16/871,000, filed on May 10, 2020, and a continuation-in-part of application No. 16/871,004, filed on May 10, 2020, and a continuation-in-part of application No. 16/909,913, filed on Jun. 23, 2020, and a continuation-in-part of application No. 16/945,827, filed on Aug. 1, 2020, now Pat. No. 11,444,710, and a continuation-in-part of application No. 16/945,837, filed on Aug. 1, 2020, now Pat. No. 11,439,344, and a continuation-in-part of application No. 17/019,270, filed on Sep. 13, 2020, and a continuation-in-part of application No. 17/113,023, filed on Dec. 5, 2020, and a continuation-in-part of application No. 17/149,625, filed on Jan. 14, 2021, and a continuation-in-part of application No. 17/149,667, filed on Jan. 14, 2021, and a continuation-in-part of application No. 17/180,763, filed on Feb. 20, 2021, and a continuation-in-part of application No. 17/180,762, filed on Feb. 20, 2021, and a continuation-in-part of application No. 17/180,766, filed on Feb. 20, 2021, and a continuation-in-part of application No. 17/214,841, filed on Mar. 27, 2021, which is a continuation-in-part of application No. 16/667,648, filed on Oct. 29, 2019, now Pat. No. 11,035,940, which is a continuation-in-part of application No. 16/446,589, filed on Jun. 19, 2019, now Pat. No. 10,742,475, which is a continuation-in-part of application No. 16/101,444, filed on Aug. 11, 2018, now Pat. No. 10,291,460, application No. 17/888,429 is a continuation-in-part of application No. 17/214,836, filed on Mar. 27, 2021, and a continuation-in-part of application No. 17/352,185, filed on Jun. 18, 2021, and a continuation-in-part of application No. 17/352,306, filed on Jun. 20, 2021, and a continuation-in-part of application No. 17/492,599, filed on Oct. 2, 2021, now Pat. No. 11,448,727, and a continuation-in-part of application No. 17/492,598, filed on Oct. 2, 2021, now Pat. No. 11,448,728, and a continuation-in-part of application No. 17/537,432, filed on Nov. 29, 2021, and a continuation-in-part of application No. 17/539,058, filed on Nov. 30, 2021, and a continuation-in-part of application No. 17/540,156, filed on Dec. 1, 2021, and a continuation-in-part of application No. 17/827,902, filed on May 30, 2022, and a continuation-in-part of application No. 17/492,642, filed on Oct. 3, 2021, and a continuation-in-part of application No. 17/838,228, filed on Jun. 12, 2022, and a continuation-in-part of application No. 17/838,231, filed on Jun. 12, 2022, and a continuation-in-part of application No. 17/838,244, filed on Jun. 12, 2022.

(60) Provisional application No. 63/253,083, filed on Oct. 6, 2021, provisional application No. 63/253,083, filed on Oct. 6, 2021, provisional application No. 63/276,652, filed on Nov. 7, 2021, provisional application No. 63/281,043, filed on Nov. 18, 2021, provisional application No. 63/293,065, filed on Dec. 22, 2021, provisional application No. 63/308,927, filed on Feb. 10, 2022, provisional application No. 63/332,658, filed on Apr. 19, 2022, provisional application No. 63/349,082, filed on Jun. 4, 2022, provisional application No. 63/300,042, filed on Jan. 16, 2022, provisional application No. 63/354,184, filed on Jun. 21, 2022, provisional application No. 63/388,625, filed on Jul. 12, 2022.

(56) References Cited

OTHER PUBLICATIONS

Cao et al., "Wi-Sleep: Contactless Sleep Monitoring via WiFi Signals", 2014, IEEE, pp. 346-355 (Year: 2014).*

* cited by examiner

METHOD, APPARATUS, AND SYSTEM FOR RADIO BASED SLEEP TRACKING

CROSS-REFERENCE TO RELATED APPLICATIONS

The present application hereby incorporates by reference the entirety of the disclosures of, and claims priority to, each of the following cases:

(a) U.S. patent application Ser. No. 16/790,610, entitled "METHOD, APPARATUS, AND SYSTEM FOR WIRELESS GAIT RECOGNITION", filed Feb. 13, 2020, (b) U.S. patent application Ser. No. 16/871,000, entitled "METHOD, APPARATUS, AND SYSTEM FOR WIRELESS TRACKING WITH GRAPH-BASED PARTICLE FILTERING", filed on May 10, 2020, (c) U.S. patent application Ser. No. 16/871,004, entitled "METHOD, APPARATUS, AND SYSTEM FOR PEOPLE COUNTING AND RECOGNITION BASED ON RHYTHMIC MOTION MONITORING", filed on May 10, 2020, (d) U.S. patent application Ser. No. 16/909,913, entitled "METHOD, APPARATUS, AND SYSTEM FOR IMPROVING TOPOLOGY OF WIRELESS SENSING SYSTEMS", filed on Jun. 23, 2020, (e) U.S. patent application Ser. No. 16/945,827, entitled "METHOD, APPARATUS, AND SYSTEM FOR PROCESSING AND PRESENTING LIFE LOG BASED ON A WIRELESS SIGNAL", filed on Aug. 1, 2020, (f) U.S. patent application Ser. No. 16/945,837, entitled "METHOD, APPARATUS, AND SYSTEM FOR WIRELESS SLEEP MONITORING", filed on Aug. 1, 2020, (g) U.S. patent application Ser. No. 17/019,270, entitled "METHOD, APPARATUS, AND SYSTEM FOR VEHICLE WIRELESS MONITORING", filed on Sep. 13, 2020, (h) U.S. patent application Ser. No. 17/113,023, entitled "METHOD, APPARATUS, AND SYSTEM FOR ACCURATE WIRELESS MONITORING", filed on Dec. 5, 2020, (i) U.S. patent application Ser. No. 17/492,642, entitled "METHOD, APPARATUS, AND SYSTEM FOR MOVEMENT TRACKING", filed on Oct. 3, 2021, (j) U.S. patent application Ser. No. 17/149,625, entitled "METHOD, APPARATUS, AND SYSTEM FOR WIRELESS MONITORING WITH MOTION LOCALIZATION", filed on Jan. 14, 2021, (k) U.S. patent application Ser. No. 17/149,667, entitled "METHOD, APPARATUS, AND SYSTEM FOR WIRELESS MONITORING WITH FLEXIBLE POWER SUPPLY", filed on Jan. 14, 2021, (l) U.S. patent application Ser. No. 17/180,763, entitled "METHOD, APPARATUS, AND SYSTEM FOR WIRELESS WRITING TRACKING", filed on Feb. 20, 2021, (m) U.S. patent application Ser. No. 17/180,762, entitled "METHOD, APPARATUS, AND SYSTEM FOR FALL-DOWN DETECTION BASED ON A WIRELESS SIGNAL", filed on Feb. 20, 2021, (n) U.S. patent application Ser. No. 17/180,766, entitled "METHOD, APPARATUS, AND SYSTEM FOR WIRELESS MOTION RECOGNITION", filed on Feb. 20, 2021, (o) U.S. patent application Ser. No. 17/214,841, entitled "METHOD, APPARATUS, AND SYSTEM FOR WIRELESS PROXIMITY SENSING", filed on Mar. 27, 2021,
  (1) which is a Continuation-in-Part of U.S. patent application Ser. No. 16/667,648, entitled "METHOD, APPARATUS, AND SYSTEM FOR WIRELESS PROXIMITY AND PRESENCE MONITORING", filed on Oct. 29, 2019, issued as U.S. Pat. No. 11,035,940 on Jun. 15, 2021,
    a. which is a Continuation-in-Part of U.S. patent application Ser. No. 16/446,589, entitled "METHOD, APPARATUS, AND SYSTEM FOR OBJECT TRACKING AND SENSING USING BROADCASTING", filed Jun. 19, 2019, issued as U.S. Pat. No. 10,742,475 on Aug. 11, 2020,
      1. which is a Continuation-in-Part of U.S. patent application Ser. No. 16/101,444, entitled "METHOD, APPARATUS, AND SYSTEM FOR WIRELESS MOTION MONITORING", filed on Aug. 11, 2018, issued as U.S. Pat. No. 10,291,460 on May 14, 2019, (p) U.S. patent application Ser. No. 17/214,836, entitled "METHOD, APPARATUS, AND SYSTEM FOR WIRELESSLY TRACKING KEYSTROKES", filed on Mar. 27, 2021, (q) U.S. patent application Ser. No. 17/352,185, entitled "METHOD, APPARATUS, AND SYSTEM FOR WIRELESS MICRO MOTION MONITORING", filed on Jun. 18, 2021, (r) U.S. patent application Ser. No. 17/352,306, entitled "METHOD, APPARATUS, AND SYSTEM FOR WIRELESS MONITORING TO ENSURE SECURITY", filed on Jun. 20, 2021, (s) U.S. Provisional Patent application 63/235,103, entitled "METHOD, APPARATUS, AND SYSTEM FOR NAMING IOT DEVICES FOR WIRELESS SENSING", filed on Aug. 19, 2021, (t) U.S. Provisional Patent application 63/253,083, entitled "METHOD, APPARATUS, AND SYSTEM FOR WIRELESS SENSING, DETECTION AND TRACKING", filed on Oct. 6, 2021, (u) U.S. patent application Ser. No. 17/492,599, entitled "METHOD, APPARATUS, AND SYSTEM FOR HUMAN RECOGNITION BASED ON GAIT FEATURES", filed on Oct. 2, 2021, (v) U.S. patent application Ser. No. 17/492,598, entitled "METHOD, APPARATUS, AND SYSTEM FOR SOUND SENSING BASED ON WIRELESS SIGNALS", filed on Oct. 2, 2021, (w) U.S. Provisional Patent application 63/276,652, entitled "METHOD, APPARATUS, AND SYSTEM FOR WIRELESSLY MONITORING VITAL SIGN AND PERIODIC MOTIONS", filed on Nov. 7, 2021, (x) U.S. Provisional Patent application 63/281,043, entitled "METHOD, APPARATUS, AND SYSTEM FOR SENSING", filed on Nov. 18, 2021, (y) U.S. patent application Ser. No. 17/537,432, entitled "METHOD, APPARATUS, AND SYSTEM FOR AUTOMATIC AND ADAPTIVE WIRELESS MONITORING AND TRACKING", filed on Nov. 29, 2021, (z) U.S. patent application Ser. No. 17/539,058, entitled "METHOD, APPARATUS, AND SYSTEM FOR HUMAN IDENTIFICATION BASED ON HUMAN RADIO BIOMETRIC INFORMATION", filed on Nov. 30, 2021, (aa) U.S. patent application Ser. No. 17/540,156, entitled "METHOD, APPARATUS, AND SYSTEM FOR POSITIONING AND POWERING A WIRELESS MONITORING SYSTEM", filed on Dec. 1, 2021, (bb) U.S. Provisional Patent application 63/293,065, entitled "METHOD, APPARATUS, AND SYSTEM FOR SPEECH ENHANCEMENT AND SEPARATION", filed on Dec. 22, 2021, (cc) U.S. Provisional Patent application 63/300,042, entitled "METHOD, APPARATUS, AND SYSTEM FOR WIRELESS SENSING AND SLEEP TRACKING", filed on Jan. 16, 2022, (dd) U.S. Provisional Patent application 63/308,927, entitled "METHOD, APPARATUS, AND SYSTEM FOR WIRELESS SENSING BASED ON MULTIPLE GROUPS OF WIRELESS DEVICES", filed on Feb. 19, 2022, (ee) U.S. Provisional Patent application 63/332,658, entitled "METHOD, APPARATUS, AND SYSTEM FOR WIRELESS SENSING", filed on Apr. 19, 2022, (ff) U.S. patent application Ser. No. 17/827,902, entitled "METHOD, APPARATUS, AND SYSTEM FOR SPEECH ENHANCEMENT AND SEPARATION BASED ON AUDIO AND RADIO SIGNALS", filed on May 30, 2022, (gg) U.S. Provisional Patent application 63/349,082, entitled "METHOD, APPARATUS, AND SYSTEM FOR WIRELESS SENSING VOICE ACTIVITY DETECTION", filed on Jun. 4, 2022, (hh) U.S. patent application Ser. No. 17/838,228, entitled "METHOD, APPARATUS, AND SYSTEM FOR WIRELESS SENSING BASED ON CHANNEL INFORMATION", filed on Jun. 12, 2022, (ii) U.S. patent application Ser. No. 17/838,231, entitled "METHOD, APPARATUS, AND SYSTEM FOR IDENTIFYING AND QUALIFYING DEVICES FOR WIRELESS SENSING", filed on Jun. 12, 2022, (jj) U.S. patent application Ser. No. 17/838,244, entitled "METHOD, APPARATUS, AND SYSTEM FOR WIRELESS SENSING BASED ON LINKWISE MOTION STATISTICS", filed on Jun. 12, 2022.

(kk) U.S. Provisional Patent application 63/354,184, entitled "METHOD, APPARATUS, AND SYSTEM FOR MOTION LOCALIZATION AND OUTLIER REMOVAL", filed on Jun. 21, 2022, (ll) U.S. Provisional Patent application 63/388,625, entitled "METHOD, APPARATUS, AND SYSTEM FOR WIRELESS SENSING AND INDOOR LOCALIZATION", filed on Jul. 12, 2022.

TECHNICAL FIELD

The present teaching generally relates to radio-based sleep tracking. More specifically, the present teaching relates to Wi-Fi-based sleep monitoring system that can work on any low-cost Internet-of-things (IoT) devices.

BACKGROUND

Sleep plays a vital role in an individual's health and well-being, both mentally and physically. It is well recognized that sleep quantity and quality is fundamentally related to health risks like cardiovascular decease, stroke, kidney failure, diabetes, and adverse mental conditions, etc. Unfortunately, in modern society, a number of people suffer from sleep disorders. As recently reported, 10% of the population suffers from chronic insomnia (which is even higher among elders), and ⅓ of Americans do not get sufficient sleep. Monitoring sleep emerges as an essential demand to help, manage, diagnose, and treat the growing group of sleep disorders as well as to keep regular tabs on personal health.

Sleep monitoring, however, is a challenging task that has drawn tremendous efforts for decades. Generally, it measures sleep time, recognizes different sleep stages, e.g., wake, REM (Rapid Eye Movement) and NREM (Non-REM), and accordingly assesses an individual's sleep quality. Various solutions have been proposed. The medical gold standard relies on Polysomnography (PSG), which monitors various physiological parameters such as brain activities, respirations, and body movements by a number of wired sensors attached to the patient. Albeit accurate and comprehensive, PSG is usually expensive and cumbersome with the invasive sensors that may cause sleep difficulties, limiting itself to clinical usage for confirmed patients. Other approaches including photoplethysmography (PPG) and actigraphy (ACT) require users to wear dedicated sensors during sleep. Ballistocardiogram (BCG) needs to instrument the mattress with an array of EMFi sensors to measure ballistic force. Despite of the costs, these approaches provide suitable solutions for those who need special cares but are less-than-ideal for the public. Recent efforts in mobile computing envision in-home sleep monitoring using smartphones and wearables. These methods, however, only provide coarse-grained, less accurate measurements and fail to monitor vital signs like respiratory rate. In addition, mobiles and wearables are undesirable for especially elders and those with dementia.

The rapid development of wireless sensing has transformed Wi-Fi from a pure communication platform to a ubiquitous sensing infrastructure. Many applications have been studied, including motion detection, sleep monitoring, gesture recognition, fall detection, gait monitoring, imaging, etc. In Wi-Fi sensing, more antennas and larger bandwidths are preferred for better performance, which, however, are not always available. Particularly, there is frequently only one single antenna with 20 MHz bandwidth on 2.4 GHz channels on low-cost, compact IoT devices, creating an extremely challenging environment for Wi-Fi sensing to be implemented. Many existing approaches would fail in such stringent conditions, since many of them rely on antenna arrays and/or larger bandwidths for channel parameter estimation or phase cleaning.

SUMMARY

The present teaching generally relates to radio-based sleep tracking. More specifically, the present teaching relates to Wi-Fi-based sleep monitoring system that can work on any low-cost Internet-of-things (IoT) devices.

In one embodiment, a system for radio-based sleep tracking is described. The system comprises: a transmitter configured to transmit a first wireless signal through a wireless multipath channel in a venue; a receiver configured to receive a second wireless signal through the wireless multipath channel, wherein the second wireless signal differs from the first wireless signal due to the wireless multipath channel which is impacted by a sleeping motion of an object in the venue; and a processor. The processor is configured for: obtaining a time series of channel information (TSCI) of the wireless multipath channel based on the second wireless signal, wherein each channel information (CI) of the TSCI comprises N1 components, wherein N1 is a positive integer larger than one, computing N1 component-wise analytics each associated with one of the N1 components of the TSCI, identifying N2 largest component-wise analytics among the N1 component-wise analytics, wherein N2 is a positive integer less than N1, computing at least one first motion statistics based on the N2 largest component-wise analytics of the TSCI, and monitoring the sleeping motion of the object based on the at least one first motion statistics.

In another embodiment, a wireless device of a system for radio-based sleep tracking is described. The wireless device comprises: a processor; a memory communicatively coupled to the processor; and a receiver communicatively coupled to the processor. An additional wireless device of the system is configured to transmit a first wireless signal through a wireless multipath channel in a venue. The receiver is configured to receive a second wireless signal through the wireless multipath channel. The second wireless signal differs from the first wireless signal due to the wireless multipath channel which is impacted by a sleeping motion of an object in the venue. The processor is configured for: obtaining a time series of channel information (TSCI) of the wireless multipath channel based on the second wireless signal, wherein each channel information (CI) of the TSCI comprises N1 components, wherein N1 is a positive integer larger than one, computing N1 component-wise analytics each associated with one of the N1 components of the TSCI, identifying N2 largest component-wise analytics among the N1 component-wise analytics, wherein N2 is a positive integer less than N1, computing at least one first motion statistics based on the N2 largest component-wise analytics of the TSCI, and monitoring the sleeping motion of the object based on the at least one first motion statistics.

In yet another embodiment, a method for radio-based sleep tracking is described. The method comprises: transmitting a first wireless signal through a wireless multipath channel in a venue; receiving a second wireless signal through the wireless multipath channel, wherein the second wireless signal differs from the first wireless signal due to the wireless multipath channel which is impacted by a sleeping motion of an object in the venue; obtaining a time series of channel information (TSCI) of the wireless multipath channel based on the second wireless signal, wherein each channel information (CI) of the TSCI comprises N1 components, wherein N1 is a positive integer larger than one; computing N1 component-wise analytics each associated with one of the N1 components of the TSCI; identifying N2 largest component-wise analytics among the N1 component-wise analytics, wherein N2 is a positive integer less than N1; computing at least one first motion statistics based on the N2 largest component-wise analytics of the TSCI; and monitoring the sleeping motion of the object based on the at least one first motion statistics.

Other concepts relate to software for implementing the present teaching on radio-based sleep tracking. Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF DRAWINGS

The methods, systems, and/or devices described herein are further described in terms of exemplary embodiments. These exemplary embodiments are described in detail with reference to the drawings. These embodiments are non-limiting exemplary embodiments, in which like reference numerals represent similar structures throughout the several views of the drawings.

DETAILED DESCRIPTION

Figure 1:
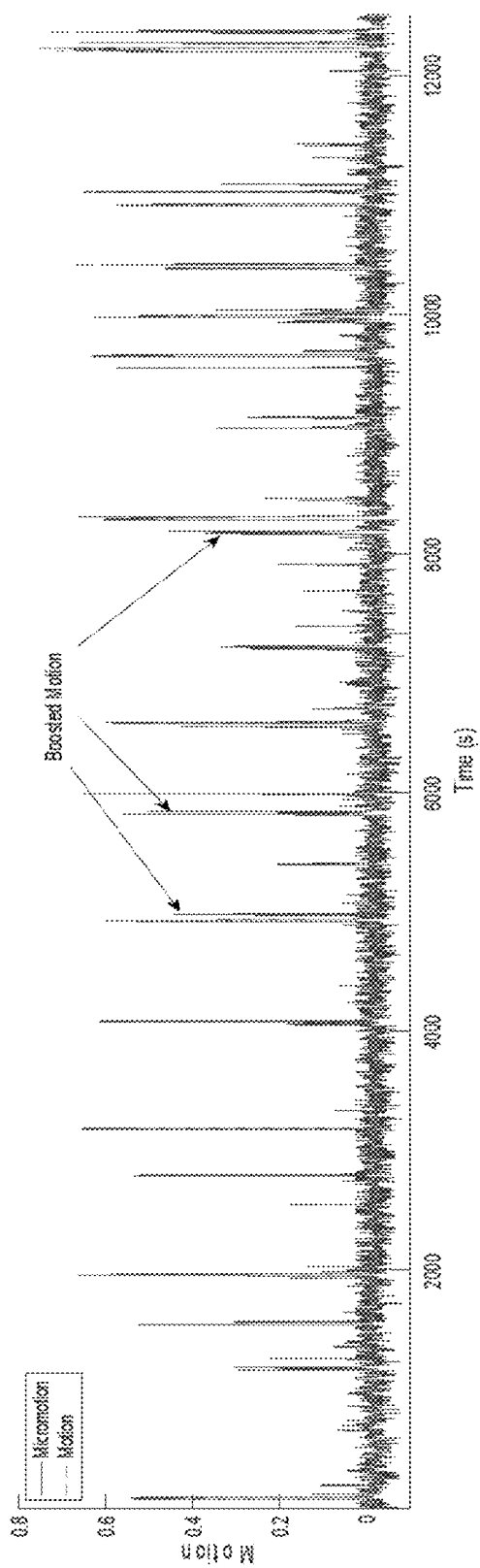
FIG. 1 illustrates an example of sleep related motion and micromotion data, according to some embodiments of the present disclosure.

In one embodiment, the present teaching discloses a method, apparatus, device, system, and/or software (method/apparatus/device/system/software) of a wireless monitoring system. A time series of channel information (CI) of a wireless multipath channel (channel) may be obtained (e.g. dynamically) using a processor, a memory communicatively coupled with the processor and a set of instructions stored in the memory. The time series of CI (TSCI) may be extracted from a wireless signal (signal) transmitted between a Type 1 heterogeneous wireless device (e.g. wireless transmitter, TX) and a Type 2 heterogeneous wireless device (e.g. wireless receiver, RX) in a venue through the channel. The channel may be impacted by an expression (e.g. motion, movement, expression, and/or change in position/pose/shape/expression) of an object in the venue. A characteristics and/or a spatial-temporal information (STI, e.g. motion information) of the object and/or of the motion of the object may be monitored based on the TSCI. A task may be performed based on the characteristics and/or STI. A presentation associated with the task may be generated in a user-interface (UI) on a device of a user. The TSCI may be a wireless signal stream. The TSCI or each CI may be preprocessed. A device may be a station (STA). The symbol "A/B" means "A and/or B" in the present teaching.

The expression may comprise placement, placement of moveable parts, location, position, orientation, identifiable place, region, spatial coordinate, presentation, state, static expression, size, length, width, height, angle, scale, shape, curve, surface, area, volume, pose, posture, manifestation, body language, dynamic expression, motion, motion sequence, gesture, extension, contraction, distortion, deformation, body expression (e.g. head, face, eye, mouth, tongue, hair, voice, neck, limbs, arm, hand, leg, foot, muscle, moveable parts), surface expression (e.g. shape, texture, material, color, electromagnetic (EM) characteristics, visual pattern, wetness, reflectance, translucency, flexibility), material property (e.g. living tissue, hair, fabric, metal, wood, leather, plastic, artificial material, solid, liquid, gas, temperature), movement, activity, behavior, change of expression, and/or some combination.

The wireless signal may comprise: transmitted/received signal, EM radiation, RF signal/transmission, signal in licensed/unlicensed/ISM band, bandlimited signal, baseband signal, wireless/mobile/cellular communication signal, wireless/mobile/cellular network signal, mesh signal, light signal/communication, downlink/uplink signal, unicast/multicast/broadcast signal, standard (e.g. WLAN, WWAN, WPAN, WBAN, international, national, industry, defacto, IEEE, IEEE 802, 802.11/15/16, WiFi, 802.11n/ac/ax/be, 3G/4G/LTE/5G/6G/7G/8G, 3GPP, Bluetooth, BLE, Zigbee, RFID, UWB, WiMax) compliant signal, protocol signal, standard frame, beacon/pilot/probe/enquiry/acknowledgement/handshake/synchronization signal, management/control/data frame, management/control/data signal, standardized wireless/cellular communication protocol, reference signal, source signal, motion probe/detection/sensing signal, and/or series of signals. The wireless signal may comprise a line-of-sight (LOS), and/or a non-LOS component (or path/link). Each CI may be extracted/generated/computed/sensed at a layer (e.g. PHY/MAC layer in OSI model) of Type 2 device and may be obtained by an application (e.g. software, firmware, driver, app, wireless monitoring software/system).

The wireless multipath channel may comprise: a communication channel, analog frequency channel (e.g. with analog carrier frequency near 700/800/900 MHz, 1.8/1.8/2.4/3/5/6/27/60 GHz), coded channel (e.g. in CDMA), and/or channel of a wireless network/system (e.g. WLAN, WiFi, mesh, LTE, 4G/5G, Bluetooth, Zigbee, UWB, RFID, microwave). It may comprise more than one channel. The channels may be consecutive (e.g. with adjacent/overlapping bands) or non-consecutive channels (e.g. non-overlapping WiFi channels, one at 2.4 GHz and one at 5 GHz).

The TSCI may be extracted from the wireless signal at a layer of the Type 2 device (e.g. a layer of OSI reference model, physical layer, data link layer, logical link control layer, media access control (MAC) layer, network layer, transport layer, session layer, presentation layer, application layer, TCP/IP layer, internet layer, link layer). The TSCI may be extracted from a derived signal (e.g. baseband signal, motion detection signal, motion sensing signal) derived from the wireless signal (e.g. RF signal). It may be (wireless) measurements sensed by the communication protocol (e.g. standardized protocol) using existing mechanism (e.g. wireless/cellular communication standard/network, 3G/LTE/4G/5G/6G/7G/8G, WiFi, IEEE 802.11/15/16). The derived signal may comprise a packet with at least one of: a preamble, a header and a payload (e.g. for data/control/management in wireless links/networks). The TSCI may be extracted from a probe signal (e.g. training sequence, STF, LTF, L-STF, L-LTF, L-SIG, HE-STF, HE-LTF, HE-SIG-A, HE-SIG-B, CEF) in the packet. A motion detection/sensing signal may be recognized/identified base on the probe signal. The packet may be a standard-compliant protocol frame, management frame, control frame, data frame, sounding frame, excitation frame, illumination frame, null data frame, beacon frame, pilot frame, probe frame, request frame, response frame, association frame, reassociation frame, disassociation frame, authentication frame, action frame, report frame, poll frame, announcement frame, extension frame, enquiry frame, acknowledgement frame, RTS frame, CTS frame, QoS frame, CF-Poll frame, CF-Ack frame, block acknowledgement frame, reference frame, training frame, and/or synchronization frame.

The packet may comprise a control data and/or a motion detection probe. A data (e.g. ID/parameters/characteristics/settings/control signal/command/instruction/notification/broadcasting-related information of the Type 1 device) may be obtained from the payload. The wireless signal may be transmitted by the Type 1 device. It may be received by the Type 2 device. A database (e.g. in local server, hub device, cloud server, storage network) may be used to store the TSCI, characteristics, STI, signatures, patterns, behaviors, trends, parameters, analytics, output responses, identification information, user information, device information, channel information, venue (e.g. map, environmental model, network, proximity devices/networks) information, task information, class/category information, presentation (e.g. UI) information, and/or other information.

The Type 1/Type 2 device may comprise at least one of: electronics, circuitry, transmitter (TX)/receiver (RX)/transceiver, RF interface, "Origin Satellite"/"Tracker Bot", unicast/multicast/broadcasting device, wireless source device, source/destination device, wireless node, hub device, target device, motion detection device, sensor device, remote/wireless sensor device, wireless communication device, wireless-enabled device, standard compliant device, and/or receiver. The Type 1 (or Type 2) device may be heterogeneous because, when there are more than one instances of Type 1 (or Type 2) device, they may have different circuitry, enclosure, structure, purpose, auxiliary functionality, chip/IC, processor, memory, software, firmware, network connectivity, antenna, brand, model, appearance, form, shape, color, material, and/or specification. The Type 1/Type 2 device may comprise: access point, router, mesh router, internet-of-things (IoT) device, wireless terminal, one or more radio/RF subsystem/wireless interface (e.g. 2.4 GHz radio, 5 GHz radio, front haul radio, backhaul radio), modem, RF front end, RF/radio chip or integrated circuit (IC).

At least one of: Type 1 device, Type 2 device, a link between them, the object, the characteristics, the STI, the monitoring of the motion, and the task may be associated with an identification (ID) such as UUID. The Type 1/Type2/another device may obtain/store/retrieve/access/preprocess/condition/process/analyze/monitor/apply the TSCI. The Type 1 and Type 2 devices may communicate network traffic in another channel (e.g. Ethernet, HDMI, USB, Bluetooth, BLE, WiFi, LTE, other network, the wireless multipath channel) in parallel to the wireless signal. The Type 2 device may passively observe/monitor/receive the wireless signal from the Type 1 device in the wireless multipath channel without establishing connection (e.g. association/authentication) with, or requesting service from, the Type 1 device.

The transmitter (i.e. Type 1 device) may function as (play role of) receiver (i.e. Type 2 device) temporarily, sporadically, continuously, repeatedly, interchangeably, alternately, simultaneously, concurrently, and/or contemporaneously; and vice versa. A device may function as Type 1 device (transmitter) and/or Type 2 device (receiver) temporarily, sporadically, continuously, repeatedly, simultaneously, concurrently, and/or contemporaneously. There may be multiple wireless nodes each being Type 1 (TX) and/or Type 2 (RX) device. A TSCI may be obtained between every two nodes when they exchange/communicate wireless signals. The characteristics and/or STI of the object may be monitored individually based on a TSCI, or jointly based on two or more (e.g. all) TSCI.

The motion of the object may be monitored actively (in that Type 1 device, Type 2 device, or both, are wearable of/associated with the object) and/or passively (in that both Type 1 and Type 2 devices are not wearable of/associated with the object). It may be passive because the object may not be associated with the Type 1 device and/or the Type 2 device. The object (e.g. user, an automated guided vehicle or AGV) may not need to carry/install any wearables/fixtures (i.e. the Type 1 device and the Type 2 device are not wearable/attached devices that the object needs to carry in order perform the task). It may be active because the object may be associated with either the Type 1 device and/or the Type 2 device. The object may carry (or installed) a wearable/a fixture (e.g. the Type 1 device, the Type 2 device, a device communicatively coupled with either the Type 1 device or the Type 2 device).

The presentation may be visual, audio, image, video, animation, graphical presentation, text, etc. A computation of the task may be performed by a processor (or logic unit) of the Type 1 device, a processor (or logic unit) of an IC of the Type 1 device, a processor (or logic unit) of the Type 2 device, a processor of an IC of the Type 2 device, a local server, a cloud server, a data analysis subsystem, a signal analysis subsystem, and/or another processor. The task may be performed with/without reference to a wireless fingerprint or a baseline (e.g. collected, processed, computed, transmitted and/or stored in a training phase/survey/current survey/previous survey/recent survey/initial wireless survey, a passive fingerprint), a training, a profile, a trained profile, a static profile, a survey, an initial wireless survey, an initial setup, an installation, a retraining, an updating and a reset.

The Type 1 device (TX device) may comprise at least one heterogeneous wireless transmitter. The Type 2 device (RX device) may comprise at least one heterogeneous wireless receiver. The Type 1 device and the Type 2 device may be collocated. The Type 1 device and the Type 2 device may be the same device. Any device may have a data processing unit/apparatus, a computing unit/system, a network unit/system, a processor (e.g. logic unit), a memory communicatively coupled with the processor, and a set of instructions stored in the memory to be executed by the processor. Some processors, memories and sets of instructions may be coordinated.

There may be multiple Type 1 devices interacting (e.g. communicating, exchange signal/control/notification/other data) with the same Type 2 device (or multiple Type 2 devices), and/or there may be multiple Type 2 devices interacting with the same Type 1 device. The multiple Type 1 devices/Type 2 devices may be synchronized and/or asynchronous, with same/different window width/size and/or time shift, same/different synchronized start time, synchronized end time, etc. Wireless signals sent by the multiple Type 1 devices may be sporadic, temporary, continuous, repeated, synchronous, simultaneous, concurrent, and/or contemporaneous. The multiple Type 1 devices/Type 2 devices may operate independently and/or collaboratively. A Type 1 and/or Type 2 device may have/comprise/be heterogeneous hardware circuitry (e.g. a heterogeneous chip or a heterogeneous IC capable of generating/receiving the wireless signal, extracting CI from received signal, or making the CI available). They may be communicatively coupled to same or different servers (e.g. cloud server, edge server, local server, hub device).

Operation of one device may be based on operation, state, internal state, storage, processor, memory output, physical location, computing resources, network of another device. Difference devices may communicate directly, and/or via another device/server/hub device/cloud server. The devices may be associated with one or more users, with associated settings. The settings may be chosen once, pre-programmed, and/or changed (e.g. adjusted, varied, modified)/varied over time. There may be additional steps in the method. The steps and/or the additional steps of the method may be performed in the order shown or in another order. Any steps may be performed in parallel, iterated, or otherwise repeated or performed in another manner. A user may be human, adult, older adult, man, woman, juvenile, child, baby, pet, animal, creature, machine, computer module/software, etc.

In the case of one or multiple Type 1 devices interacting with one or multiple Type 2 devices, any processing (e.g. time domain, frequency domain) may be different for different devices. The processing may be based on locations, orientation, direction, roles, user-related characteristics, settings, configurations, available resources, available bandwidth, network connection, hardware, software, processor, co-processor, memory, battery life, available power, antennas, antenna types, directional/unidirectional characteristics of the antenna, power setting, and/or other parameters/characteristics of the devices.

The wireless receiver (e.g. Type 2 device) may receive the signal and/or another signal from the wireless transmitter (e.g. Type 1 device). The wireless receiver may receive another signal from another wireless transmitter (e.g. a second Type 1 device). The wireless transmitter may transmit the signal and/or another signal to another wireless receiver (e.g. a second Type 2 device). The wireless transmitter, wireless receiver, another wireless receiver and/or another wireless transmitter may be moving with the object and/or another object. The another object may be tracked.

The Type 1 and/or Type 2 device may be capable of wirelessly coupling with at least two Type 2 and/or Type 1 devices. The Type 1 device may be caused/controlled to switch/establish wireless coupling (e.g. association, authentication) from the Type 2 device to a second Type 2 device at another location in the venue. Similarly, the Type 2 device may be caused/controlled to switch/establish wireless coupling from the Type 1 device to a second Type 1 device at yet another location in the venue. The switching may be controlled by a server (or a hub device), the processor, the Type 1 device, the Type 2 device, and/or another device. The radio used before and after switching may be different. A second wireless signal (second signal) may be caused to be transmitted between the Type 1 device and the second Type 2 device (or between the Type 2 device and the second Type 1 device) through the channel. A second TSCI of the channel extracted from the second signal may be obtained. The second signal may be the first signal. The characteristics, STI and/or another quantity of the object may be monitored based on the second TSCI. The Type 1 device and the Type 2 device may be the same. The characteristics, STI and/or another quantity with different time stamps may form a waveform. The waveform may be displayed in the presentation.

The wireless signal and/or another signal may have data embedded. The wireless signal may be a series of probe signals (e.g. a repeated transmission of probe signals, a re-use of one or more probe signals). The probe signals may change/vary over time. A probe signal may be a standard compliant signal, protocol signal, standardized wireless protocol signal, control signal, data signal, wireless communication network signal, cellular network signal, WiFi signal, LTE/5G/6G/7G signal, reference signal, beacon signal, motion detection signal, and/or motion sensing signal. A probe signal may be formatted according to a wireless network standard (e.g. WiFi), a cellular network standard (e.g. LTE/5G/6G), or another standard. A probe signal may comprise a packet with a header and a payload. A probe signal may have data embedded. The payload may comprise data. A probe signal may be replaced by a data signal. The probe signal may be embedded in a data signal. The wireless receiver, wireless transmitter, another wireless receiver and/or another wireless transmitter may be associated with at least one processor, memory communicatively coupled with respective processor, and/or respective set of instructions stored in the memory which when executed cause the processor to perform any and/or all steps needed to determine the STI (e.g. motion information), initial STI, initial time, direction, instantaneous location, instantaneous angle, and/or speed, of the object.

The processor, the memory and/or the set of instructions may be associated with the Type 1 device, one of the at least one Type 2 device, the object, a device associated with the object, another device associated with the venue, a cloud server, a hub device, and/or another server.

The Type 1 device may transmit the signal in a broadcasting manner to at least one Type 2 device(s) through the channel in the venue. The signal is transmitted without the Type 1 device establishing wireless connection (e.g. association, authentication) with any Type 2 device, and without any Type 2 device requesting services from the Type 1 device. The Type 1 device may transmit to a particular media access control (MAC) address common for more than one Type 2 devices. Each Type 2 device may adjust its MAC address to the particular MAC address. The particular MAC address may be associated with the venue. The association may be recorded in an association table of an Association Server (e.g. hub device). The venue may be identified by the Type 1 device, a Type 2 device and/or another device based on the particular MAC address, the series of probe signals, and/or the at least one TSCI extracted from the probe signals.

For example, a Type 2 device may be moved to a new location in the venue (e.g. from another venue). The Type 1 device may be newly set up in the venue such that the Type 1 and Type 2 devices are not aware of each other. During set up, the Type 1 device may be instructed/guided/caused/controlled (e.g. using dummy receiver, using hardware pin setting/connection, using stored setting, using local setting, using remote setting, using downloaded setting, using hub device, or using server) to send the series of probe signals to the particular MAC address. Upon power up, the Type 2 device may scan for probe signals according to a table of MAC addresses (e.g. stored in a designated source, server, hub device, cloud server) that may be used for broadcasting at different locations (e.g. different MAC address used for different venue such as house, office, enclosure, floor, multi-storey building, store, airport, mall, stadium, hall, station, subway, lot, area, zone, region, district, city, country, continent). When the Type 2 device detects the probe signals sent to the particular MAC address, the Type 2 device can use the table to identify the venue based on the MAC address.

A location of a Type 2 device in the venue may be computed based on the particular MAC address, the series of probe signals, and/or the at least one TSCI obtained by the Type 2 device from the probe signals. The computing may be performed by the Type 2 device.

The particular MAC address may be changed (e.g. adjusted, varied, modified) over time. It may be changed according to a time table, rule, policy, mode, condition, situation and/or change. The particular MAC address may be selected based on availability of the MAC address, a pre-selected list, collision pattern, traffic pattern, data traffic between the Type 1 device and another device, effective bandwidth, random selection, and/or a MAC address switching plan. The particular MAC address may be the MAC address of a second wireless device (e.g. a dummy receiver, or a receiver that serves as a dummy receiver).

The Type 1 device may transmit the probe signals in a channel selected from a set of channels. At least one CI of the selected channel may be obtained by a respective Type 2 device from the probe signal transmitted in the selected channel.

The selected channel may be changed (e.g. adjusted, varied, modified) over time. The change may be according to a time table, rule, policy, mode, condition, situation, and/or change. The selected channel may be selected based on availability of channels, random selection, a pre-selected list, co-channel interference, inter-channel interference, channel traffic pattern, data traffic between the Type 1 device and another device, effective bandwidth associated with channels, security criterion, channel switching plan, a criterion, a quality criterion, a signal quality condition, and/or consideration.

The particular MAC address and/or an information of the selected channel may be communicated between the Type 1 device and a server (e.g. hub device) through a network. The particular MAC address and/or the information of the selected channel may also be communicated between a Type 2 device and a server (e.g. hub device) through another network. The Type 2 device may communicate the particular MAC address and/or the information of the selected channel to another Type 2 device (e.g. via mesh network, Bluetooth, WiFi, NFC, ZigBee, etc.). The particular MAC address and/or selected channel may be chosen by a server (e.g. hub device). The particular MAC address and/or selected channel may be signaled in an announcement channel by the Type 1 device, the Type 2 device and/or a server (e.g. hub device). Before being communicated, any information may be pre-processed.

Wireless connection (e.g. association, authentication) between the Type 1 device and another wireless device may be established (e.g. using a signal handshake). The Type 1 device may send a first handshake signal (e.g. sounding frame, probe signal, request-to-send RTS) to the another device. The another device may reply by sending a second handshake signal (e.g. a command, or a clear-to-send CTS) to the Type 1 device, triggering the Type 1 device to transmit the signal (e.g. series of probe signals) in the broadcasting manner to multiple Type 2 devices without establishing connection with any Type 2 device. The second handshake signals may be a response or an acknowledge (e.g. ACK) to the first handshake signal. The second handshake signal may contain a data with information of the venue, and/or the Type 1 device. The another device may be a dummy device with a purpose (e.g. primary purpose, secondary purpose) to establish the wireless connection with the Type 1 device, to receive the first signal, and/or to send the second signal. The another device may be physically attached to the Type 1 device.

In another example, the another device may send a third handshake signal to the Type 1 device triggering the Type 1 device to broadcast the signal (e.g. series of probe signals) to multiple Type 2 devices without establishing connection (e.g. association, authentication) with any Type 2 device. The Type 1 device may reply to the third special signal by transmitting a fourth handshake signal to the another device. The another device may be used to trigger more than one Type 1 devices to broadcast. The triggering may be sequential, partially sequential, partially parallel, or fully parallel. The another device may have more than one wireless circuitries to trigger multiple transmitters in parallel. Parallel trigger may also be achieved using at least one yet another device to perform the triggering (similar to what as the another device does) in parallel to the another device. The another device may not communicate (or suspend communication) with the Type 1 device after establishing connection with the Type 1 device. Suspended communication may be resumed. The another device may enter an inactive mode, hibernation mode, sleep mode, stand-by mode, low-power mode, OFF mode and/or power-down mode, after establishing the connection with the Type 1 device. The another device may have the particular MAC address so that the Type 1 device sends the signal to the particular MAC address. The Type 1 device and/or the another device may be controlled and/or coordinated by a first processor associated with the Type 1 device, a second processor associated with the another device, a third processor associated with a designated source and/or a fourth processor associated with another device. The first and second processors may coordinate with each other.

A first series of probe signals may be transmitted by a first antenna of the Type 1 device to at least one first Type 2 device through a first channel in a first venue. A second series of probe signals may be transmitted by a second antenna of the Type 1 device to at least one second Type 2 device through a second channel in a second venue. The first series and the second series may/may not be different. The at least one first Type 2 device may/may not be different from the at least one second Type 2 device. The first and/or second series of probe signals may be broadcasted without connection (e.g. association, authentication) established between the Type 1 device and any Type 2 device. The first and second antennas may be same/different.

The two venues may have different sizes, shape, multipath characteristics. The first and second venues may overlap. The respective immediate areas around the first and second antennas may overlap. The first and second channels may be same/different. For example, the first one may be WiFi while the second may be LTE. Or, both may be WiFi, but the first one may be 2.4 GHz WiFi and the second may be 5 GHz WiFi. Or, both may be 2.4 GHz WiFi, but have different channel numbers, SSID names, and/or WiFi settings.

Each Type 2 device may obtain at least one TSCI from the respective series of probe signals, the CI being of the respective channel between the Type 2 device and the Type 1 device. Some first Type 2 device(s) and some second Type 2 device(s) may be the same. The first and second series of probe signals may be synchronous/asynchronous. A probe signal may be transmitted with data or replaced by a data signal. The first and second antennas may be the same.

The first series of probe signals may be transmitted at a first rate (e.g. 30 Hz). The second series of probe signals may be transmitted at a second rate (e.g. 200 Hz). The first and second rates may be same/different. The first and/or second rate may be changed (e.g. adjusted, varied, modified) over time. The change may be according to a time table, rule, policy, mode, condition, situation, and/or change. Any rate may be changed (e.g. adjusted, varied, modified) over time.

The first and/or second series of probe signals may be transmitted to a first MAC address and/or second MAC address respectively. The two MAC addresses may be same/different. The first series of probe signals may be transmitted in a first channel. The second series of probe signals may be transmitted in a second channel. The two channels may be same/different. The first or second MAC address, first or second channel may be changed over time. Any change may be according to a time table, rule, policy, mode, condition, situation, and/or change.

The Type 1 device and another device may be controlled and/or coordinated, physically attached, or may be of/in/of a common device. They may be controlled by/connected to a common data processor, or may be connected to a common bus interconnect/network/LAN/Bluetooth network/NFC network/BLE network/wired network/wireless network/mesh network/mobile network/cloud. They may share a common memory, or be associated with a common user, user device, profile, account, identity (ID), identifier, household, house, physical address, location, geographic coordinate, IP subnet, SSID, home device, office device, and/or manufacturing device.

Each Type 1 device may be a signal source of a set of respective Type 2 devices (i.e. it sends a respective signal (e.g. respective series of probe signals) to the set of respective Type 2 devices). Each respective Type 2 device chooses the Type 1 device from among all Type 1 devices as its signal source. Each Type 2 device may choose asynchronously. At least one TSCI may be obtained by each respective Type 2 device from the respective series of probe signals from the Type 1 device, the CI being of the channel between the Type 2 device and the Type 1 device.

The respective Type 2 device chooses the Type 1 device from among all Type 1 devices as its signal source based on identity (ID) or identifier of Type 1/Type 2 device, task to be performed, past signal source, history (e.g. of past signal source, Type 1 device, another Type 1 device, respective Type 2 receiver, and/or another Type 2 receiver), threshold for switching signal source, and/or information of a user, account, access info, parameter, characteristics, and/or signal strength (e.g. associated with the Type 1 device and/or the respective Type 2 receiver).

Initially, the Type 1 device may be signal source of a set of initial respective Type 2 devices (i.e. the Type 1 device sends a respective signal (series of probe signals) to the set of initial respective Type 2 devices) at an initial time. Each initial respective Type 2 device chooses the Type 1 device from among all Type 1 devices as its signal source.

The signal source (Type 1 device) of a particular Type 2 device may be changed (e.g. adjusted, varied, modified) when (1) time interval between two adjacent probe signals (e.g. between current probe signal and immediate past probe signal, or between next probe signal and current probe signal) received from current signal source of the Type 2 device exceeds a first threshold; (2) signal strength associated with current signal source of the Type 2 device is below a second threshold; (3) a processed signal strength associated with current signal source of the Type 2 device is below a third threshold, the signal strength processed with low pass filter, band pass filter, median filter, moving average filter, weighted averaging filter, linear filter and/or non-linear filter; and/or (4) signal strength (or processed signal strength) associated with current signal source of the Type 2 device is below a fourth threshold for a significant percentage of a recent time window (e.g. 70%, 80%, 90%). The percentage may exceed a fifth threshold. The first, second, third, fourth and/or fifth thresholds may be time varying.

Condition (1) may occur when the Type 1 device and the Type 2 device become progressively far away from each other, such that some probe signal from the Type 1 device becomes too weak and is not received by the Type 2 device. Conditions (2)-(4) may occur when the two devices become far from each other such that the signal strength becomes very weak.

The signal source of the Type 2 device may not change if other Type 1 devices have signal strength weaker than a factor (e.g. 1, 1.1, 1.2, or 1.5) of the current signal source.

If the signal source is changed (e.g. adjusted, varied, modified), the new signal source may take effect at a near future time (e.g. the respective next time). The new signal source may be the Type 1 device with strongest signal strength, and/or processed signal strength. The current and new signal source may be same/different.

A list of available Type 1 devices may be initialized and maintained by each Type 2 device. The list may be updated by examining signal strength and/or processed signal strength associated with the respective set of Type 1 devices. A Type 2 device may choose between a first series of probe signals from a first Type 1 device and a second series of probe signals from a second Type 1 device based on: respective probe signal rate, MAC addresses, channels, characteristics/properties/states, task to be performed by the Type 2 device, signal strength of first and second series, and/or another consideration.

The series of probe signals may be transmitted at a regular rate (e.g. 100 Hz). The series of probe signals may be scheduled at a regular interval (e.g. 0.01 s for 100 Hz), but each probe signal may experience small time perturbation, perhaps due to timing requirement, timing control, network control, handshaking, message passing, collision avoidance, carrier sensing, congestion, availability of resources, and/or another consideration.

The rate may be changed (e.g. adjusted, varied, modified). The change may be according to a time table (e.g. changed once every hour), rule, policy, mode, condition and/or change (e.g. changed whenever some event occur). For example, the rate may normally be 100 Hz, but changed to 1000 Hz in demanding situations, and to 1 Hz in low power/standby situation. The probe signals may be sent in burst.

The probe signal rate may change based on a task performed by the Type 1 device or Type 2 device (e.g. a task may need 100 Hz normally and 1000 Hz momentarily for 20 seconds). In one example, the transmitters (Type 1 devices), receivers (Type 2 device), and associated tasks may be associated adaptively (and/or dynamically) to classes (e.g. classes that are: low-priority, high-priority, emergency, critical, regular, privileged, non-subscription, subscription, paying, and/or non-paying). A rate (of a transmitter) may be adjusted for the sake of some class (e.g. high priority class). When the need of that class changes, the rate may be changed (e.g. adjusted, varied, modified). When a receiver has critically low power, the rate may be reduced to reduce power consumption of the receiver to respond to the probe signals. In one example, probe signals may be used to transfer power wirelessly to a receiver (Type 2 device), and the rate may be adjusted to control the amount of power transferred to the receiver.

The rate may be changed by (or based on): a server (e.g. hub device), the Type 1 device and/or the Type 2 device. Control signals may be communicated between them. The server may monitor, track, forecast and/or anticipate the needs of the Type 2 device and/or the tasks performed by the Type 2 device, and may control the Type 1 device to change the rate. The server may make scheduled changes to the rate according to a time table. The server may detect an emergency situation and change the rate immediately. The server may detect a developing condition and adjust the rate gradually.

The characteristics and/or STI (e.g. motion information) may be monitored individually based on a TSCI associated with a particular Type 1 device and a particular Type 2 device, and/or monitored jointly based on any TSCI associated with the particular Type 1 device and any Type 2 device, and/or monitored jointly based on any TSCI associated with the particular Type 2 device and any Type 1 device, and/or monitored globally based on any TSCI associated with any Type 1 device and any Type 2 device. Any joint monitoring may be associated with: a user, user account, profile, household, map of venue, environmental model of the venue, and/or user history, etc.

A first channel between a Type 1 device and a Type 2 device may be different from a second channel between another Type 1 device and another Type 2 device. The two channels may be associated with different frequency bands, bandwidth, carrier frequency, modulation, wireless standards, coding, encryption, payload characteristics, networks, network ID, SSID, network characteristics, network settings, and/or network parameters, etc.

The two channels may be associated with different kinds of wireless system (e.g. two of the following: WiFi, LTE, LTE-A, LTE-U, 2.5G, 3G, 3.5G, 4G, beyond 4G, 5G, 6G, 7G, a cellular network standard, UMTS, 3GPP, GSM, EDGE, TDMA, FDMA, CDMA, WCDMA, TD-SCDMA, 802.11 system, 802.15 system, 802.16 system, mesh network, Zigbee, NFC, WiMax, Bluetooth, BLE, RFID, UWB, microwave system, radar like system). For example, one is WiFi and the other is LTE.

The two channels may be associated with similar kinds of wireless system, but in different network. For example, the first channel may be associated with a WiFi network named "Pizza and Pizza" in the 2.4 GHz band with a bandwidth of 20 MHz while the second may be associated with a WiFi network with SSID of "StarBud hotspot" in the 5 GHz band with a bandwidth of 40 MHz. The two channels may be different channels in same network (e.g. the "StarBud hotspot" network).

In one embodiment, a wireless monitoring system may comprise training a classifier of multiple events in a venue based on training TSCI associated with the multiple events. A CI or TSCI associated with an event may be considered/may comprise a wireless sample/characteristics/fingerprint associated with the event (and/or the venue, the environment, the object, the motion of the object, a state/emotional state/mental state/condition/stage/gesture/gait/action/movement/activity/daily activity/history/event of the object, etc.).

For each of the multiple known events happening in the venue in a respective training (e.g. surveying, wireless survey, initial wireless survey) time period associated with the known event, a respective training wireless signal (e.g. a respective series of training probe signals) may be transmitted by an antenna of a first Type 1 heterogeneous wireless device using a processor, a memory and a set of instructions of the first Type 1 device to at least one first Type 2 heterogeneous wireless device through a wireless multipath channel in the venue in the respective training time period.

At least one respective time series of training CI (training TSCI) may be obtained asynchronously by each of the at least one first Type 2 device from the (respective) training signal. The CI may be CI of the channel between the first Type 2 device and the first Type 1 device in the training time period associated with the known event. The at least one training TSCI may be preprocessed. The training may be a wireless survey (e.g. during installation of Type 1 device and/or Type 2 device).

For a current event happening in the venue in a current time period, a current wireless signal (e.g. a series of current probe signals) may be transmitted by an antenna of a second Type 1 heterogeneous wireless device using a processor, a memory and a set of instructions of the second Type 1 device to at least one second Type 2 heterogeneous wireless device through the channel in the venue in the current time period associated with the current event.

At least one time series of current CI (current TSCI) may be obtained asynchronously by each of the at least one second Type 2 device from the current signal (e.g. the series of current probe signals). The CI may be CI of the channel between the second Type 2 device and the second Type 1 device in the current time period associated with the current event. The at least one current TSCI may be preprocessed.

The classifier may be applied to classify at least one current TSCI obtained from the series of current probe signals by the at least one second Type 2 device, to classify at least one portion of a particular current TSCI, and/or to classify a combination of the at least one portion of the particular current TSCI and another portion of another TSCI. The classifier may partition TSCI (or the characteristics/STI or other analytics or output responses) into clusters and associate the clusters to specific events/objects/subjects/locations/movements/activities. Labels/tags may be generated for the clusters. The clusters may be stored and retrieved. The classifier may be applied to associate the current TSCI (or characteristics/STI or the other analytics/output response, perhaps associated with a current event) with: a cluster, a known/specific event, a class/category/group/grouping/list/cluster/set of known events/subjects/locations/movements/activities, an unknown event, a class/category/group/grouping/list/cluster/set of unknown events/subjects/locations/movements/activities, and/or another event/subject/location/movement/activity/class/category/group/grouping/list/cluster/set. Each TSCI may comprise at least one CI each associated with a respective timestamp. Two TSCI associated with two Type 2 devices may be different with different: starting time, duration, stopping time, amount of CI, sampling frequency, sampling period. Their CI may have different features. The first and second Type 1 devices may be at same location in the venue. They may be the same device. The at least one second Type 2 device (or their locations) may be a permutation of the at least one first Type 2 device (or their locations). A particular second Type 2 device and a particular first Type 2 device may be the same device.

A subset of the first Type 2 device and a subset of the second Type 2 device may be the same. The at least one second Type 2 device and/or a subset of the at least one second Type 2 device may be a subset of the at least one first Type 2 device. The at least one first Type 2 device and/or a subset of the at least one first Type 2 device may be a permutation of a subset of the at least one second Type 2 device. The at least one second Type 2 device and/or a subset of the at least one second Type 2 device may be a permutation of a subset of the at least one first Type 2 device. The at least one second Type 2 device and/or a subset of the at least one second Type 2 device may be at same respective location as a subset of the at least one first Type 2 device. The at least one first Type 2 device and/or a subset of the at least one first Type 2 device may be at same respective location as a subset of the at least one second Type 2 device.

The antenna of the Type 1 device and the antenna of the second Type 1 device may be at same location in the venue. Antenna(s) of the at least one second Type 2 device and/or antenna(s) of a subset of the at least one second Type 2 device may be at same respective location as respective antenna(s) of a subset of the at least one first Type 2 device. Antenna(s) of the at least one first Type 2 device and/or antenna(s) of a subset of the at least one first Type 2 device may be at same respective location(s) as respective antenna(s) of a subset of the at least one second Type 2 device.

A first section of a first time duration of the first TSCI and a second section of a second time duration of the second section of the second TSCI may be aligned. A map between items of the first section and items of the second section may be computed. The first section may comprise a first segment (e.g. subset) of the first TSCI with a first starting/ending time, and/or another segment (e.g. subset) of a processed first TSCI. The processed first TSCI may be the first TSCI processed by a first operation. The second section may comprise a second segment (e.g. subset) of the second TSCI with a second starting time and a second ending time, and another segment (e.g. subset) of a processed second TSCI. The processed second TSCI may be the second TSCI processed by a second operation. The first operation and/or the second operation may comprise: subsampling, re-sampling, interpolation, filtering, transformation, feature extraction, pre-processing, and/or another operation.

A first item of the first section may be mapped to a second item of the second section. The first item of the first section may also be mapped to another item of the second section. Another item of the first section may also be mapped to the second item of the second section. The mapping may be one-to-one, one-to-many, many-to-one, many-to-many. At least one function of at least one of: the first item of the first section of the first TSCI, another item of the first TSCI, timestamp of the first item, time difference of the first item, time differential of the first item, neighboring timestamp of the first item, another timestamp associated with the first item, the second item of the second section of the second TSCI, another item of the second TSCI, timestamp of the second item, time difference of the second item, time differential of the second item, neighboring timestamp of the second item, and another timestamp associated with the second item, may satisfy at least one constraint.

One constraint may be that a difference between the timestamp of the first item and the timestamp of the second item may be upper-bounded by an adaptive (and/or dynamically adjusted) upper threshold and lower-bounded by an adaptive lower threshold.

The first section may be the entire first TSCI. The second section may be the entire second TSCI. The first time duration may be equal to the second time duration. A section of a time duration of a TSCI may be determined adaptively (and/or dynamically). A tentative section of the TSCI may be computed. A starting time and an ending time of a section (e.g. the tentative section, the section) may be determined. The section may be determined by removing a beginning portion and an ending portion of the tentative section. A beginning portion of a tentative section may be determined as follows. Iteratively, items of the tentative section with increasing timestamp may be considered as a current item, one item at a time.

In each iteration, at least one activity measure/index may be computed and/or considered. The at least one activity measure may be associated with at least one of: the current item associated with a current timestamp, past items of the tentative section with timestamps not larger than the current timestamp, and/or future items of the tentative section with timestamps not smaller than the current timestamp. The current item may be added to the beginning portion of the tentative section if at least one criterion (e.g. quality criterion, signal quality condition) associated with the at least one activity measure is satisfied.

The at least one criterion associated with the activity measure may comprise at least one of: (a) the activity measure is smaller than an adaptive (e.g. dynamically adjusted) upper threshold, (b) the activity measure is larger than an adaptive lower threshold, (c) the activity measure is smaller than an adaptive upper threshold consecutively for at least a predetermined amount of consecutive timestamps, (d) the activity measure is larger than an adaptive lower threshold consecutively for at least another predetermined amount of consecutive timestamps, (e) the activity measure is smaller than an adaptive upper threshold consecutively for at least a predetermined percentage of the predetermined amount of consecutive timestamps, (f) the activity measure is larger than an adaptive lower threshold consecutively for at least another predetermined percentage of the another predetermined amount of consecutive timestamps, (g) another activity measure associated with another timestamp associated with the current timestamp is smaller than another adaptive upper threshold and larger than another adaptive lower threshold, (h) at least one activity measure associated with at least one respective timestamp associated with the current timestamp is smaller than respective upper threshold and larger than respective lower threshold, (i) percentage of timestamps with associated activity measure smaller than respective upper threshold and larger than respective lower threshold in a set of timestamps associated with the current timestamp exceeds a threshold, and (j) another criterion (e.g. a quality criterion, signal quality condition).

An activity measure/index associated with an item at time T1 may comprise at least one of: (1) a first function of the item at time T1 and an item at time T1−D1, wherein D1 is a pre-determined positive quantity (e.g. a constant time offset), (2) a second function of the item at time T1 and an item at time T1+D1, (3) a third function of the item at time T1 and an item at time T2, wherein T2 is a pre-determined quantity (e.g. a fixed initial reference time; T2 may be changed (e.g. adjusted, varied, modified) over time; T2 may be updated periodically; T2 may be the beginning of a time period and T1 may be a sliding time in the time period), and (4) a fourth function of the item at time T1 and another item.

At least one of: the first function, the second function, the third function, and/or the fourth function may be a function (e.g. $F(X, Y, \ldots)$) with at least two arguments: X and Y. The two arguments may be scalars. The function (e.g. F) may be a function of at least one of: $X, Y, (X-Y), (Y-X), abs(X-Y), X^a, Y^b, abs(X^a-Y^b), (X-Y)^a, (X/Y), (X+a)/(Y+b), (X^a/Y^b)$, and $((X/Y)^a-b)$, wherein a and b are may be some predetermined quantities. For example, the function may simply be $abs(X-Y)$, or $(X-Y)^2, (X-Y)^4$. The function may be a robust function. For example, the function may be $(X-Y)^2$ when abs $(X-Y)$ is less than a threshold T, and $(X-Y)+a$ when $abs(X-Y)$ is larger than T. Alternatively, the function may be a constant when $abs(X-Y)$ is larger than T. The function may also be bounded by a slowly increasing function when $abs(X-y)$ is larger than T, so that outliers cannot severely affect the result. Another example of the function may be $(abs(X/Y)-a)$, where a=1. In this way, if X=Y (i.e. no change or no activity), the function will give a value of 0. If X is larger than Y, (X/Y) will be larger than 1 (assuming X and Y are positive) and the function will be positive. And if X is less than Y, (X/Y) will be smaller than 1 and the function will be negative. In another example, both arguments X and Y may be n-tuples such that $X=(x\_1, x\_2, \ldots, x\_n)$ and $Y=(y\_1, y\_2, \ldots, y\_n)$. The function may be a function of at least one of: $x\_i, y\_i, (x\_i-y\_i), (y\_i-x\_i), abs(x\_i-y\_i), x\_i^a, y\_i^b, abs(x\_i^a-y\_i^b), (x\_i-y\_i)^a, (x\_i/y\_i), (x\_i+a)/(y\_i+b), (x\_i^a/y\_i^b)$, and $((x\_i/y\_i)^a-b)$, wherein i is a component index of the n-tuple X and Y, and $1<=i<=n$, e.g. component index of x_1 is i=1, component index of x_2 is i=2. The function may comprise a component-by-component summation of another function of at least one of the following: $x\_i, y\_i, (x\_i-y\_i), (y\_i-x\_i), abs(x\_i-y\_i), x\_i^a, y\_i^b, abs(x\_i^a-y\_i^b), (x\_i-y\_i)^a, (x\_i/y\_i), (x\_i+a)/(y\_i+b), (x\_i^a/y\_i^b)$, and $((x\_i/y\_i)^a-b)$, wherein i is the component index of the n-tuple X and Y. For example, the function may be in a form of $sum\_\{i=1\}^n (abs(x\_i/y\_i)-1)/n$, or $sum\_\{i=1\}^n w\_i * (abs(x\_i/y\_i)-1)$, where $w\_i$ is some weight for component i.

The map may be computed using dynamic time warping (DTW). The DTW may comprise a constraint on at least one of: the map, the items of the first TSCI, the items of the second TSCI, the first time duration, the second time duration, the first section, and/or the second section. Suppose in the map, the $i^{\{th\}}$ domain item is mapped to the $j^{\{th\}}$ range item. The constraint may be on admissible combination of i and j (constraint on relationship between i and j). Mismatch cost between a first section of a first time duration of a first TSCI and a second section of a second time duration of a second TSCI may be computed.

The first section and the second section may be aligned such that a map comprising more than one links may be established between first items of the first TSCI and second items of the second TSCI. With each link, one of the first items with a first timestamp may be associated with one of the second items with a second timestamp. A mismatch cost between the aligned first section and the aligned second section may be computed. The mismatch cost may comprise a function of: an item-wise cost between a first item and a second item associated by a particular link of the map, and a link-wise cost associated with the particular link of the map.

The aligned first section and the aligned second section may be represented respectively as a first vector and a second vector of same vector length. The mismatch cost may comprise at least one of: an inner product, inner-product-like quantity, quantity based on correlation, correlation indicator, quantity based on covariance, discriminating score, distance, Euclidean distance, absolute distance, Lk distance (e.g. L1, L2, . . . ), weighted distance, distance-like quantity and/or another similarity value, between the first vector and the second vector. The mismatch cost may be normalized by the respective vector length.

A parameter derived from the mismatch cost between the first section of the first time duration of the first TSCI and the second section of the second time duration of the second TSCI may be modeled with a statistical distribution. At least one of: a scale parameter, location parameter and/or another parameter, of the statistical distribution may be estimated.

The first section of the first time duration of the first TSCI may be a sliding section of the first TSCI. The second section of the second time duration of the second TSCI may be a sliding section of the second TSCI.

A first sliding window may be applied to the first TSCI and a corresponding second sliding window may be applied to the second TSCI. The first sliding window of the first TSCI and the corresponding second sliding window of the second TSCI may be aligned.

Mismatch cost between the aligned first sliding window of the first TSCI and the corresponding aligned second sliding window of the second TSCI may be computed. The current event may be associated with at least one of: the known event, the unknown event and/or the another event, based on the mismatch cost.

The classifier may be applied to at least one of: each first section of the first time duration of the first TSCI, and/or each second section of the second time duration of the second TSCI, to obtain at least one tentative classification results. Each tentative classification result may be associated with a respective first section and a respective second section.

The current event may be associated with at least one of: the known event, the unknown event, a class/category/group/grouping/list/set of unknown events, and/or the another event, based on the mismatch cost. The current event may be associated with at least one of: the known event, the unknown event and/or the another event, based on a largest number of tentative classification results in more than one sections of the first TSCI and corresponding more than sections of the second TSCI. For example, the current event may be associated with a particular known event if the mismatch cost points to the particular known event for N consecutive times (e.g. N=10). In another example, the current event may be associated with a particular known event if the percentage of mismatch cost within the immediate past N consecutive N pointing to the particular known event exceeds a certain threshold (e.g. >80%).

In another example, the current event may be associated with a known event that achieves smallest mismatch cost for the most times within a time period. The current event may be associated with a known event that achieves smallest overall mismatch cost, which is a weighted average of at least one mismatch cost associated with the at least one first sections. The current event may be associated with a particular known event that achieves smallest of another overall cost. The current event may be associated with the "unknown event" if none of the known events achieve mismatch cost lower than a first threshold T1 in a sufficient percentage of the at least one first section. The current event may also be associated with the "unknown event" if none of the events achieve an overall mismatch cost lower than a second threshold T2. The current event may be associated with at least one of: the known event, the unknown event and/or the another event, based on the mismatch cost and additional mismatch cost associated with at least one additional section of the first TSCI and at least one additional section of the second TSCI. The known events may comprise at least one of: a door closed event, door open event, window closed event, window open event, multi-state event, on-state event, off-state event, intermediate state event, continuous state event, discrete state event, human-present event, human-absent event, sign-of-life-present event, and/or a sign-of-life-absent event.

A projection for each CI may be trained using a dimension reduction method based on the training TSCI. The dimension reduction method may comprise at least one of: principal component analysis (PCA), PCA with different kernel, independent component analysis (ICA), Fisher linear discriminant, vector quantization, supervised learning, unsupervised learning, self-organizing maps, auto-encoder, neural network, deep neural network, and/or another method. The projection may be applied to at least one of: the training TSCI associated with the at least one event, and/or the current TSCI, for the classifier.

The classifier of the at least one event may be trained based on the projection and the training TSCI associated with the at least one event. The at least one current TSCI may be classified/categorized based on the projection and the current TSCI. The projection may be re-trained using at least one of: the dimension reduction method, and another dimension reduction method, based on at least one of: the training TSCI, at least one current TSCI before retraining the projection, and/or additional training TSCI. The another dimension reduction method may comprise at least one of: principal component analysis (PCA), PCA with different kernels, independent component analysis (ICA), Fisher linear discriminant, vector quantization, supervised learning, unsupervised learning, self-organizing maps, auto-encoder, neural network, deep neural network, and/or yet another method. The classifier of the at least one event may be re-trained based on at least one of: the re-trained projection, the training TSCI associated with the at least one events, and/or at least one current TSCI. The at least one current TSCI may be classified based on: the re-trained projection, the re-trained classifier, and/or the current TSCI.

Each CI may comprise a vector of complex values. Each complex value may be preprocessed to give the magnitude of the complex value. Each CI may be preprocessed to give a vector of non-negative real numbers comprising the magnitude of corresponding complex values. Each training TSCI may be weighted in the training of the projection. The projection may comprise more than one projected components. The projection may comprise at least one most significant projected component. The projection may comprise at least one projected component that may be beneficial for the classifier.

Channel/Channel Information/Venue/Spatial-Temporal Info/Motion/Object

The channel information (CI) may be associated with/may comprise signal strength, signal amplitude, signal phase, spectral power measurement, modem parameters (e.g. used in relation to modulation/demodulation in digital communication systems such as WiFi, 4G/LTE), dynamic beamforming information (including feedback or steering matrices generated by wireless communication devices, according to a standardized process, e.g., IEEE 802.11, or another standard), transfer function components, radio state (e.g. used in digital communication systems to decode digital data, baseband processing state, RF processing state, etc.), measurable variables, sensed data, coarse-grained/fine-grained information of a layer (e.g. physical layer, data link layer, MAC layer, etc.), digital setting, gain setting, RF filter setting, RF front end switch setting, DC offset setting, DC correction setting, IQ compensation setting, effect(s) on the wireless signal by the environment (e.g. venue) during propagation, transformation of an input signal (the wireless signal transmitted by the Type 1 device) to an output signal (the wireless signal received by the Type 2 device), a stable behavior of the environment, a state profile, wireless channel measurements, received signal strength indicator (RSSI), channel state information (CSI), channel impulse response (CIR), channel frequency response (CFR), characteristics of frequency components (e.g. subcarriers) in a bandwidth, channel characteristics, channel filter response, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another channel information. Each CI may be associated with a time stamp, and/or an arrival time. A CSI can be used to equalize/undo/minimize/reduce the multipath channel effect (of the transmission channel) to demodulate a signal similar to the one transmitted by the transmitter through the multipath channel. The CI may be associated with information associated with a frequency band, frequency signature, frequency phase, frequency amplitude, frequency trend, frequency characteristics, frequency-like characteristics, time domain element, frequency domain element, time-frequency domain element, orthogonal decomposition characteristics, and/or non-orthogonal decomposition characteristics of the signal through the channel. The TSCI may be a stream of wireless signals (e.g. CI).

The CI may be preprocessed, processed, postprocessed, stored (e.g. in local memory, portable/mobile memory, removable memory, storage network, cloud memory, in a volatile manner, in a non-volatile manner), retrieved, transmitted and/or received. One or more modem parameters and/or radio state parameters may be held constant. The modem parameters may be applied to a radio subsystem. The modem parameters may represent a radio state. A motion detection signal (e.g. baseband signal, and/or packet decoded/demodulated from the baseband signal, etc.) may be obtained by processing (e.g. down-converting) the first wireless signal (e.g. RF/WiFi/LTE/5G signal) by the radio subsystem using the radio state represented by the stored modem parameters. The modem parameters/radio state may be updated (e.g. using previous modem parameters or previous radio state). Both the previous and updated modem parameters/radio states may be applied in the radio subsystem in the digital communication system. Both the previous and updated modem parameters/radio states may be compared/analyzed/processed/monitored in the task.

The channel information may also be modem parameters (e.g. stored or freshly computed) used to process the wireless signal. The wireless signal may comprise a plurality of probe signals. The same modem parameters may be used to process more than one probe signals. The same modem parameters may also be used to process more than one wireless signals. The modem parameters may comprise parameters that indicate settings or an overall configuration for the operation of a radio subsystem or a baseband subsystem of a wireless sensor device (or both). The modem parameters may include one or more of: a gain setting, an RF filter setting, an RF front end switch setting, a DC offset setting, or an IQ compensation setting for a radio subsystem, or a digital DC correction setting, a digital gain setting, and/or a digital filtering setting (e.g. for a baseband subsystem). The CI may also be associated with information associated with a time period, time signature, timestamp, time amplitude, time phase, time trend, and/or time characteristics of the signal. The CI may be associated with information associated with a time-frequency partition, signature, amplitude, phase, trend, and/or characteristics of the signal. The CI may be associated with a decomposition of the signal. The CI may be associated with information associated with a direction, angle of arrival (AoA), angle of a directional antenna, and/or a phase of the signal through the channel. The CI may be associated with attenuation patterns of the signal through the channel. Each CI may be associated with a Type 1 device and a Type 2 device. Each CI may be associated with an antenna of the Type 1 device and an antenna of the Type 2 device.

The CI may be obtained from a communication hardware (e.g. of Type 2 device, or Type 1 device) that is capable of providing the CI. The communication hardware may be a WiFi-capable chip/IC (integrated circuit), chip compliant with a 802.11 or 802.16 or another wireless/radio standard, next generation WiFi-capable chip, LTE-capable chip, 5G-capable chip, 6G/7G/8G-capable chip, Bluetooth-enabled chip, NFC (near field communication)-enabled chip, BLE (Bluetooth low power)-enabled chip, UWB chip, another communication chip (e.g. Zigbee, WiMax, mesh network), etc. The communication hardware computes the CI and stores the CI in a buffer memory and make the CI available for extraction. The CI may comprise data and/or at least one matrices related to channel state information (CSI). The at least one matrices may be used for channel equalization, and/or beam forming, etc. The channel may be associated with a venue. The attenuation may be due to signal propagation in the venue, signal propagating/reflection/refraction/diffraction through/at/around air (e.g. air of venue), refraction medium/reflection surface such as wall, doors, furniture, obstacles and/or barriers, etc. The attenuation may be due to reflection at surfaces and obstacles (e.g. reflection surface, obstacle) such as floor, ceiling, furniture, fixtures, objects, people, pets, etc. Each CI may be associated with a timestamp. Each CI may comprise N1 components (e.g. N1 frequency domain components in CFR, N1 time domain components in CIR, or N1 decomposition components). Each component may be associated with a component index. Each component may be a real, imaginary, or complex quantity, magnitude, phase, flag, and/or set. Each CI may comprise a vector or matrix of complex numbers, a set of mixed quantities, and/or a multi-dimensional collection of at least one complex numbers.

Components of a TSCI associated with a particular component index may form a respective component time series associated with the respective index. A TSCI may be divided into N1 component time series. Each respective component time series is associated with a respective component index. The characteristics/STI of the motion of the object may be monitored based on the component time series. In one example, one or more ranges of CI components (e.g. one range being from component 11 to component 23, a second range being from component 44 to component 50, and a third range having only one component) may be selected based on some criteria/cost function/signal quality metric (e.g. based on signal-to-noise ratio, and/or interference level) for further processing.

A component-wise characteristic of a component-feature time series of a TSCI may be computed. The component-wise characteristics may be a scalar (e.g. energy) or a function with a domain and a range (e.g. an autocorrelation function, transform, inverse transform). The characteristics/STI of the motion of the object may be monitored based on the component-wise characteristics. A total characteristics (e.g. aggregate characteristics) of the TSCI may be computed based on the component-wise characteristics of each component time series of the TSCI. The total characteristics may be a weighted average of the component-wise characteristics. The characteristics/STI of the motion of the object may be monitored based on the total characteristics. An aggregate quantity may be a weighted average of individual quantities.

The Type 1 device and Type 2 device may support WiFi, WiMax, 3G/beyond 3G, 4G/beyond 4G, LTE, LTE-A, 5G, 6G, 7G, Bluetooth, NFC, BLE, Zigbee, UWB, UMTS, 3GPP, GSM, EDGE, TDMA, FDMA, CDMA, WCDMA, TD-SCDMA, mesh network, proprietary wireless system, IEEE 802.11 standard, 802.15 standard, 802.16 standard, 3GPP standard, and/or another wireless system.

A common wireless system and/or a common wireless channel may be shared by the Type 1 transceiver and/or the at least one Type 2 transceiver. The at least one Type 2 transceiver may transmit respective signal contemporaneously (or: asynchronously, synchronously, sporadically, continuously, repeatedly, concurrently, simultaneously and/or temporarily) using the common wireless system and/or the common wireless channel. The Type 1 transceiver may transmit a signal to the at least one Type 2 transceiver using the common wireless system and/or the common wireless channel.

Each Type 1 device and Type 2 device may have at least one transmitting/receiving antenna. Each CI may be associated with one of the transmitting antenna of the Type 1 device and one of the receiving antenna of the Type 2 device. Each pair of a transmitting antenna and a receiving antenna may be associated with a link, a path, a communication path, signal hardware path, etc. For example, if the Type 1 device has M (e.g. 3) transmitting antennas, and the Type 2 device has N (e.g. 2) receiving antennas, there may be M×N (e.g. 3×2=6) links or paths. Each link or path may be associated with a TSCI.

The at least one TSCI may correspond to various antenna pairs between the Type 1 device and the Type 2 device. The Type 1 device may have at least one antenna. The Type 2 device may also have at least one antenna. Each TSCI may be associated with an antenna of the Type 1 device and an antenna of the Type 2 device. Averaging or weighted averaging over antenna links may be performed. The averaging or weighted averaging may be over the at least one TSCI. The averaging may optionally be performed on a subset of the at least one TSCI corresponding to a subset of the antenna pairs.

Timestamps of CI of a portion of a TSCI may be irregular and may be corrected so that corrected timestamps of time-corrected CI may be uniformly spaced in time. In the case of multiple Type 1 devices and/or multiple Type 2 devices, the corrected timestamp may be with respect to the same or different clock. An original timestamp associated with each of the CI may be determined. The original timestamp may not be uniformly spaced in time. Original timestamps of all CI of the particular portion of the particular TSCI in the current sliding time window may be corrected so that corrected timestamps of time-corrected CI may be uniformly spaced in time.

The characteristics and/or STI (e.g. motion information) may comprise: location, location coordinate, change in location, position (e.g. initial position, new position), position on map, height, horizontal location, vertical location, distance, displacement, speed, acceleration, rotational speed, rotational acceleration, direction, angle of motion, azimuth, direction of motion, rotation, path, deformation, transformation, shrinking, expanding, gait, gait cycle, head motion, repeated motion, periodic motion, pseudo-periodic motion, impulsive motion, sudden motion, fall-down motion, transient motion, behavior, transient behavior, period of motion, frequency of motion, time trend, temporal profile, temporal characteristics, occurrence, change, temporal change, change of CI, change in frequency, change in timing, change of gait cycle, timing, starting time, initiating time, ending time, duration, history of motion, motion type, motion classification, frequency, frequency spectrum, frequency characteristics, presence, absence, proximity, approaching, receding, identity/identifier of the object, composition of the object, head motion rate, head motion direction, mouth-related rate, eye-related rate, breathing rate, heart rate, tidal volume, depth of breath, inhale time, exhale time, inhale time to exhale time ratio, airflow rate, heart heat-to-beat interval, heart rate variability, hand motion rate, hand motion direction, leg motion, body motion, walking rate, hand motion rate, positional characteristics, characteristics associated with movement (e.g. change in position/location) of the object, tool motion, machine motion, complex motion, and/or combination of multiple motions, event, signal statistics, signal dynamics, anomaly, motion statistics, motion parameter, indication of motion detection, motion magnitude, motion phase, similarity score, distance score, Euclidean distance, weighted distance, L_1 norm, L_2 norm, L_k norm for k>2, statistical distance, correlation, correlation indicator, auto-correlation, covariance, auto-covariance, cross-covariance, inner product, outer product, motion signal transformation, motion feature, presence of motion, absence of motion, motion localization, motion identification, motion recognition, presence of object, absence of object, entrance of object, exit of object, a change of object, motion cycle, motion count, gait cycle, motion rhythm, deformation motion, gesture, handwriting, head motion, mouth motion, heart motion, internal organ motion, motion trend, size, length, area, volume, capacity, shape, form, tag, starting/initiating location, ending location, starting/initiating quantity, ending quantity, event, fall-down event, security event, accident event, home event, office event, factory event, warehouse event, manufacturing event, assembly line event, maintenance event, car-related event, navigation event, tracking event, door event, door-open event, door-close event, window event, window-open event, window-close event, repeatable event, one-time event, consumed quantity, unconsumed quantity, state, physical state, health state, well-being state, emotional state, mental state, another event, analytics, output responses, and/or another information. The characteristics and/or STI may be computed/monitored based on a feature computed from a CI or a TSCI (e.g. feature computation/extraction). A static segment or profile (and/or a dynamic segment/profile) may be identified/computed/analyzed/monitored/extracted/obtained/marked/presented/indicated/highlighted/stored/communicated based on an analysis of the feature. The analysis may comprise a motion detection/movement assessment/presence detection. Computational workload may be shared among the Type 1 device, the Type 2 device and another processor.

The Type 1 device and/or Type 2 device may be a local device. The local device may be: a smart phone, smart device, TV, sound bar, set-top box, access point, router, repeater, wireless signal repeater/extender, remote control, speaker, fan, refrigerator, microwave, oven, coffee machine, hot water pot, utensil, table, chair, light, lamp, door lock, camera, microphone, motion sensor, security device, fire hydrant, garage door, switch, power adapter, computer, dongle, computer peripheral, electronic pad, sofa, tile, accessory, home device, vehicle device, office device, building device, manufacturing device, watch, glasses, clock, television, oven, air-conditioner, accessory, utility, appliance, smart machine, smart vehicle, internet-of-thing (IoT) device, internet-enabled device, computer, portable computer, tablet, smart house, smart office, smart building, smart parking lot, smart system, and/or another device.

Each Type 1 device may be associated with a respective identifier (e.g. ID). Each Type 2 device may also be associated with a respective identify (ID). The ID may comprise: numeral, combination of text and numbers, name, password, account, account ID, web link, web address, index to some information, and/or another ID. The ID may be assigned. The ID may be assigned by hardware (e.g. hardwired, via dongle and/or other hardware), software and/or firmware. The ID may be stored (e.g. in database, in memory, in server (e.g. hub device), in the cloud, stored locally, stored remotely, stored permanently, stored temporarily) and may be retrieved. The ID may be associated with at least one record, account, user, household, address, phone number, social security number, customer number, another ID, another identifier, timestamp, and/or collection of data. The ID and/or part of the ID of a Type 1 device may be made available to a Type 2 device. The ID may be used for registration, initialization, communication, identification, verification, detection, recognition, authentication, access control, cloud access, networking, social networking, logging, recording, cataloging, classification, tagging, association, pairing, transaction, electronic transaction, and/or intellectual property control, by the Type 1 device and/or the Type 2 device.

The object may be person, user, subject, passenger, child, older person, baby, sleeping baby, baby in vehicle, patient, worker, high-value worker, expert, specialist, waiter, customer in mall, traveler in airport/train station/bus terminal/shipping terminals, staff/worker/customer service personnel in factory/mall/supermarket/office/workplace, serviceman in sewage/air ventilation system/lift well, lifts in lift wells, elevator, inmate, people to be tracked/monitored, animal, plant, living object, pet, dog, cat, smart phone, phone accessory, computer, tablet, portable computer, dongle, computing accessory, networked devices, WiFi devices, IoT devices, smart watch, smart glasses, smart devices, speaker, keys, smart key, wallet, purse, handbag, backpack, goods, cargo, luggage, equipment, motor, machine, air conditioner, fan, air conditioning equipment, light fixture, moveable light, television, camera, audio and/or video equipment, stationary, surveillance equipment, parts, signage, tool, cart, ticket, parking ticket, toll ticket, airplane ticket, credit card, plastic card, access card, food packaging, utensil, table, chair, cleaning equipment/tool, vehicle, car, cars in parking facilities, merchandise in warehouse/store/supermarket/distribution center, boat, bicycle, airplane, drone, remote control car/plane/boat, robot, manufacturing device, assembly line, material/unfinished part/robot/wagon/transports on factory floor, object to be tracked in airport/shopping mart/supermarket, non-object, absence of an object, presence of an object, object with form, object with changing form, object with no form, mass of fluid, mass of liquid, mass of gas/smoke, fire, flame, electromagnetic (EM) source, EM medium, and/or another object.

The object itself may be communicatively coupled with some network, such as WiFi, MiFi, 3G/4G/LTE/5G/6G/7G, Bluetooth, NFC, BLE, WiMax, Zigbee, UMTS, 3GPP, GSM, EDGE, TDMA, FDMA, CDMA, WCDMA, TD-SCDMA, mesh network, adhoc network, and/or other network. The object itself may be bulky with AC power supply, but is moved during installation, cleaning, maintenance, renovation, etc. It may also be installed in moveable platform such as lift, pad, movable, platform, elevator, conveyor belt, robot, drone, forklift, car, boat, vehicle, etc. The object may have multiple parts, each part with different movement (e.g. change in position/location). For example, the object may be a person walking forward. While walking, his left hand and right hand may move in different direction, with different instantaneous speed, acceleration, motion, etc.

The wireless transmitter (e.g. Type 1 device), the wireless receiver (e.g. Type 2 device), another wireless transmitter and/or another wireless receiver may move with the object and/or another object (e.g. in prior movement, current movement and/or future movement. They may be communicatively coupled to one or more nearby device. They may transmit TSCI and/or information associated with the TSCI to the nearby device, and/or each other. They may be with the nearby device. The wireless transmitter and/or the wireless receiver may be part of a small (e.g. coin-size, cigarette box size, or even smaller), light-weight portable device. The portable device may be wirelessly coupled with a nearby device.

The nearby device may be smart phone, iPhone, Android phone, smart device, smart appliance, smart vehicle, smart gadget, smart TV, smart refrigerator, smart speaker, smart watch, smart glasses, smart pad, iPad, computer, wearable computer, notebook computer, gateway. The nearby device may be connected to a cloud server, local server (e.g. hub device) and/or other server via internet, wired internet connection and/or wireless internet connection. The nearby device may be portable. The portable device, the nearby device, a local server (e.g. hub device) and/or a cloud server may share the computation and/or storage for a task (e.g. obtain TSCI, determine characteristics/STI of the object associated with the movement (e.g. change in position/location) of the object, computation of time series of power (e.g. signal strength) information, determining/computing the particular function, searching for local extremum, classification, identifying particular value of time offset, denoising, processing, simplification, cleaning, wireless smart sensing task, extract CI from signal, switching, segmentation, estimate trajectory/path/track, process the map, processing trajectory/path/track based on environment models/constraints/limitations, correction, corrective adjustment, adjustment, map-based (or model-based) correction, detecting error, checking for boundary hitting, thresholding) and information (e.g. TSCI). The nearby device may/may not move with the object. The nearby device may be portable/not portable/moveable/non-moveable. The nearby device may use battery power, solar power, AC power and/or other power source. The nearby device may have replaceable/non-replaceable battery, and/or rechargeable/non-rechargeable battery. The nearby device may be similar to the object. The nearby device may have identical (and/or similar) hardware and/or software to the object. The nearby device may be a smart device, network enabled device, device with connection to WiFi/3G/4G/5G/6G/Zigbee/Bluetooth/NFC/UMTS/3GPP/GSM/EDGE/TDMA/FDMA/CDMA/WCDMA/TD-SCDMA/adhoc network/other network, smart speaker, smart watch, smart clock, smart appliance, smart machine, smart equipment, smart tool, smart vehicle, internet-of-thing (IoT) device, internet-enabled device, computer, portable computer, tablet, and another device. The nearby device and/or at least one processor associated with the wireless receiver, the wireless transmitter, the another wireless receiver, the another wireless transmitter and/or a cloud server (in the cloud) may determine the initial STI of the object. Two or more of them may determine the initial spatial-temporal info jointly. Two or more of them may share intermediate information in the determination of the initial STI (e.g. initial position).

In one example, the wireless transmitter (e.g. Type 1 device, or Tracker Bot) may move with the object. The wireless transmitter may send the signal to the wireless receiver (e.g. Type 2 device, or Origin Register) or determining the initial STI (e.g. initial position) of the object. The wireless transmitter may also send the signal and/or another signal to another wireless receiver (e.g. another Type 2 device, or another Origin Register) for the monitoring of the motion (spatial-temporal info) of the object. The wireless receiver may also receive the signal and/or another signal from the wireless transmitter and/or the another wireless transmitter for monitoring the motion of the object. The location of the wireless receiver and/or the another wireless receiver may be known. In another example, the wireless receiver (e.g. Type 2 device, or Tracker Bot) may move with the object. The wireless receiver may receive the signal transmitted from the wireless transmitter (e.g. Type 1 device, or Origin Register) for determining the initial spatial-temporal info (e.g. initial position) of the object. The wireless receiver may also receive the signal and/or another signal from another wireless transmitter (e.g. another Type 1 device, or another Origin Register) for the monitoring of the current motion (e.g. spatial-temporal info) of the object. The wireless transmitter may also transmit the signal and/or another signal to the wireless receiver and/or the another wireless receiver (e.g. another Type 2 device, or another Tracker Bot) for monitoring the motion of the object. The location of the wireless transmitter and/or the another wireless transmitter may be known.

The venue may be a space such as a sensing area, room, house, office, property, workplace, hallway, walkway, lift, lift well, escalator, elevator, sewage system, air ventilations system, staircase, gathering area, duct, air duct, pipe, tube, enclosed space, enclosed structure, semi-enclosed structure, enclosed area, area with at least one wall, plant, machine, engine, structure with wood, structure with glass, structure with metal, structure with walls, structure with doors, structure with gaps, structure with reflection surface, structure with fluid, building, roof top, store, factory, assembly line, hotel room, museum, classroom, school, university, government building, warehouse, garage, mall, airport, train station, bus terminal, hub, transportation hub, shipping terminal, government facility, public facility, school, university, entertainment facility, recreational facility, hospital, pediatric/neonatal wards, seniors home, elderly care facility, geriatric facility, community center, stadium, playground, park, field, sports facility, swimming facility, track and/or field, basketball court, tennis court, soccer stadium, baseball stadium, gymnasium, hall, garage, shopping mart, mall, supermarket, manufacturing facility, parking facility, construction site, mining facility, transportation facility, highway, road, valley, forest, wood, terrain, landscape, den, patio, land, path, amusement park, urban area, rural area, suburban area, metropolitan area, garden, square, plaza, music hall, downtown facility, over-air facility, semi-open facility, closed area, train platform, train station, distribution center, warehouse, store, distribution center, storage facility, underground facility, space (e.g. above ground, outer-space) facility, floating facility, cavern, tunnel facility, indoor facility, open-air facility, outdoor facility with some walls/doors/ reflective barriers, open facility, semi-open facility, car, truck, bus, van, container, ship/boat, submersible, train, tram, airplane, vehicle, mobile home, cave, tunnel, pipe, channel, metropolitan area, downtown area with relatively tall buildings, valley, well, duct, pathway, gas line, oil line, water pipe, network of interconnecting pathways/alleys/ roads/tubes/cavities/caves/pipe-like structure/air space/fluid space, human body, animal body, body cavity, organ, bone, teeth, soft tissue, hard tissue, rigid tissue, non-rigid tissue, blood/body fluid vessel, windpipe, air duct, den, etc. The venue may be indoor space, outdoor space. The venue may include both the inside and outside of the space. For example, the venue may include both the inside of a building and the outside of the building. For example, the venue can be a building that has one floor or multiple floors, and a portion of the building can be underground. The shape of the building can be, e.g., round, square, rectangular, triangle, or irregular-shaped. These are merely examples. The disclosure can be used to detect events in other types of venue or spaces.

The wireless transmitter (e.g. Type 1 device) and/or the wireless receiver (e.g. Type 2 device) may be embedded in a portable device (e.g. a module, or a device with the module) that may move with the object (e.g. in prior movement and/or current movement). The portable device may be communicatively coupled with the object using a wired connection (e.g. through USB, microUSB, Firewire, HDMI, serial port, parallel port, and other connectors) and/or a connection (e.g. Bluetooth, Bluetooth Low Energy (BLE), WiFi, LTE, NFC, ZigBee). The portable device may be a lightweight device. The portable may be powered by battery, rechargeable battery and/or AC power. The portable device may be very small (e.g. at sub-millimeter scale and/or sub-centimeter scale), and/or small (e.g. coin-size, card-size, pocket-size, or larger). The portable device may be large, sizable, and/or bulky (e.g. heavy machinery to be installed). The portable device may be a WiFi hotspot, access point, mobile WiFi (MiFi), dongle with USB/micro USB/Firewire/ other connector, smartphone, portable computer, computer, tablet, smart device, internet-of-thing (IoT) device, WiFi-enabled device, LTE-enabled device, a smart watch, smart glass, smart mirror, smart antenna, smart battery, smart light, smart pen, smart ring, smart door, smart window, smart clock, small battery, smart wallet, smart belt, smart handbag, smart clothing/garment, smart ornament, smart packaging, smart paper/book/magazine/poster/printed matter/signage/ display/lighted system/lighting system, smart key/tool, smart bracelet/chain/necklace/wearable/accessory, smart pad/cushion, smart tile/block/brick/building material/other material, smart garbage can/waste container, smart food carriage/storage, smart ball/racket, smart chair/sofa/bed, smart shoe/footwear/carpet/mat/shoe rack, smart glove/hand wear/ring/hand ware, smart hat/headwear/makeup/sticker/ tattoo, smart mirror, smart toy, smart pill, smart utensil, smart bottle/food container, smart tool, smart device, IoT device, WiFi enabled device, network enabled device, 3G/4G/5G/6G enabled device, UMTS devices, 3GPP devices, GSM devices, EDGE devices, TDMA devices, FDMA devices, CDMA devices, WCDMA devices, TD-SCDMA devices, embeddable device, implantable device, air conditioner, refrigerator, heater, furnace, furniture, oven, cooking device, television/set-top box (STB)/DVD player/ audio player/video player/remote control, hi-fi, audio device, speaker, lamp/light, wall, door, window, roof, roof tile/shingle/structure/attic structure/device/feature/installation/fixtures, lawn mower/garden tools/yard tools/mechanics tools/garage tools/, garbage can/container, 20-ft/40-ft container, storage container, factory/manufacturing/production device, repair tools, fluid container, machine, machinery to be installed, vehicle, cart, wagon, warehouse vehicle, car, bicycle, motorcycle, boat, vessel, airplane, basket/box/bag/ bucket/container, smart plate/cup/bowl/pot/mat/utensils/ kitchen tools/kitchen devices/kitchen accessories/cabinets/ tables/chairs/tiles/lights/water pipes/taps/gas range/oven/ dishwashing machine/etc. The portable device may have a battery that may be replaceable, irreplaceable, rechargeable, and/or non-rechargeable. The portable device may be wirelessly charged. The portable device may be a smart payment card. The portable device may be a payment card used in parking lots, highways, entertainment parks, or other venues/facilities that need payment. The portable device may have an identity (ID)/identifier as described above.

An event may be monitored based on the TSCI. The event may be an object related event, such as fall-down of the object (e.g. an person and/or a sick person), rotation, hesitation, pause, impact (e.g. a person hitting a sandbag, door, window, bed, chair, table, desk, cabinet, box, another person, animal, bird, fly, table, chair, ball, bowling ball, tennis ball, football, soccer ball, baseball, basketball, volley ball), two-body action (e.g. a person letting go a balloon, catching a fish, molding a clay, writing a paper, person typing on a computer), car moving in a garage, person carrying a smart phone and walking around an airport/mall/government building/office/etc., autonomous moveable object/machine moving around (e.g. vacuum cleaner, utility vehicle, car, drone, self-driving car).

The task or the wireless smart sensing task may comprise: object detection, presence detection, proximity detection, object recognition, activity recognition, object verification, object counting, daily activity monitoring, well-being monitoring, vital sign monitoring, health condition monitoring, baby monitoring, elderly monitoring, sleep monitoring, sleep stage monitoring, walking monitoring, exercise monitoring, tool detection, tool recognition, tool verification, patient detection, patient monitoring, patient verification, machine detection, machine recognition, machine verification, human detection, human recognition, human verification, baby detection, baby recognition, baby verification, human breathing detection, human breathing recognition, human breathing estimation, human breathing verification, human heart beat detection, human heart beat recognition, human heart beat estimation, human heart beat verification, fall-down detection, fall-down recognition, fall-down estimation, fall-down verification, emotion detection, emotion recognition, emotion estimation, emotion verification, motion detection, motion degree estimation, motion recognition, motion estimation, motion verification, periodic motion detection, periodic motion recognition, periodic motion estimation, periodic motion verification, repeated motion detection, repeated motion recognition, repeated motion estimation, repeated motion verification, stationary motion detection, stationary motion recognition, stationary motion estimation, stationary motion verification, cyclo-stationary motion detection, cyclo-stationary motion recognition, cyclo-stationary motion estimation, cyclo-stationary motion verification, transient motion detection, transient motion recognition, transient motion estimation, transient motion verification, trend detection, trend recognition, trend estimation, trend verification, breathing detection, breathing recognition, breathing estimation, breathing estimation, human biometrics detection, human biometric recognition, human biometrics estimation, human biometrics verification, environment informatics detection, environment informatics recognition, environment informatics estimation, environment informatics verification, gait detection, gait recognition, gait estimation, gait verification, gesture detection, gesture recognition, gesture estimation, gesture verification, machine learning, supervised learning, unsupervised learning, semi-supervised learning, clustering, feature extraction, featuring training, principal component analysis, eigen-decomposition, frequency decomposition, time decomposition, time-frequency decomposition, functional decomposition, other decomposition, training, discriminative training, supervised training, unsupervised training, semi-supervised training, neural network, sudden motion detection, fall-down detection, danger detection, life-threat detection, regular motion detection, stationary motion detection, cyclo-stationary motion detection, intrusion detection, suspicious motion detection, security, safety monitoring, navigation, guidance, map-based processing, map-based correction, model-based processing/correction, irregularity detection, locationing, room sensing, tracking, multiple object tracking, indoor tracking, indoor position, indoor navigation, energy management, power transfer, wireless power transfer, object counting, car tracking in parking garage, activating a device/system (e.g. security system, access system, alarm, siren, speaker, television, entertaining system, camera, heater/air-conditioning (HVAC) system, ventilation system, lighting system, gaming system, coffee machine, cooking device, cleaning device, housekeeping device), geometry estimation, augmented reality, wireless communication, data communication, signal broadcasting, networking, coordination, administration, encryption, protection, cloud computing, other processing and/or other task. The task may be performed by the Type 1 device, the Type 2 device, another Type 1 device, another Type 2 device, a nearby device, a local server (e.g. hub device), edge server, a cloud server, and/or another device. The task may be based on TSCI between any pair of Type 1 device and Type 2 device. A Type 2 device may be a Type 1 device, and vice versa. A Type 2 device may play/perform the role (e.g. functionality) of Type 1 device temporarily, continuously, sporadically, simultaneously, and/or contemporaneously, and vice versa. A first part of the task may comprise at least one of: preprocessing, processing, signal conditioning, signal processing, post-processing, processing sporadically/continuously/simultaneously/contemporaneously/dynamically/adaptive/on-demand/as-needed, calibrating, denoising, feature extraction, coding, encryption, transformation, mapping, motion detection, motion estimation, motion change detection, motion pattern detection, motion pattern estimation, motion pattern recognition, vital sign detection, vital sign estimation, vital sign recognition, periodic motion detection, periodic motion estimation, repeated motion detection/estimation, breathing rate detection, breathing rate estimation, breathing pattern detection, breathing pattern estimation, breathing pattern recognition, heart beat detection, heart beat estimation, heart pattern detection, heart pattern estimation, heart pattern recognition, gesture detection, gesture estimation, gesture recognition, speed detection, speed estimation, object locationing, object tracking, navigation, acceleration estimation, acceleration detection, fall-down detection, change detection, intruder (and/or illegal action) detection, baby detection, baby monitoring, patient monitoring, object recognition, wireless power transfer, and/or wireless charging.

A second part of the task may comprise at least one of: a smart home task, smart office task, smart building task, smart factory task (e.g. manufacturing using a machine or an assembly line), smart internet-of-thing (IoT) task, smart system task, smart home operation, smart office operation, smart building operation, smart manufacturing operation (e.g. moving supplies/parts/raw material to a machine/an assembly line), IoT operation, smart system operation, turning on a light, turning off the light, controlling the light in at least one of: a room, region, and/or the venue, playing a sound clip, playing the sound clip in at least one of: the room, the region, and/or the venue, playing the sound clip of at least one of: a welcome, greeting, farewell, first message, and/or a second message associated with the first part of the task, turning on an appliance, turning off the appliance, controlling the appliance in at least one of: the room, the region, and/or the venue, turning on an electrical system, turning off the electrical system, controlling the electrical system in at least one of: the room, the region, and/or the venue, turning on a security system, turning off the security system, controlling the security system in at least one of: the room, the region, and/or the venue, turning on a mechanical system, turning off a mechanical system, controlling the mechanical system in at least one of: the room, the region, and/or the venue, and/or controlling at least one of: an air conditioning system, heating system, ventilation system, lighting system, heating device, stove, entertainment system, door, fence, window, garage, computer system, networked device, networked system, home appliance, office equipment, lighting device, robot (e.g. robotic arm), smart vehicle, smart machine, assembly line, smart device, internet-of-thing (IoT) device, smart home device, and/or a smart office device.

The task may include: detect a user returning home, detect a user leaving home, detect a user moving from one room to another, detect/control/lock/unlock/open/close/partially open a window/door/garage door/blind/curtain/panel/solar panel/sun shade, detect a pet, detect/monitor a user doing something (e.g. sleeping on sofa, sleeping in bedroom, running on treadmill, cooking, sitting on sofa, watching TV, eating in kitchen, eating in dining room, going upstairs/downstairs, going outside/coming back, in the rest room), monitor/detect location of a user/pet, do something (e.g. send a message, notify/report to someone) automatically upon detection, do something for the user automatically upon detecting the user, turn on/off/dim a light, turn on/off music/radio/home entertainment system, turn on/off/adjust/control TV/HiFi/set-top-box (STB)/home entertainment system/smart speaker/smart device, turn on/off/adjust air conditioning system, turn on/off/adjust ventilation system, turn on/off/adjust heating system, adjust/control curtains/light shades, turn on/off/wake a computer, turn on/off/pre-heat/control coffee machine/hot water pot, turn on/off/control/preheat cooker/oven/microwave oven/another cooking device, check/adjust temperature, check weather forecast, check telephone message box, check mail, do a system check, control/adjust a system, check/control/arm/disarm security system/baby monitor, check/control refrigerator, give a report (e.g. through a speaker such as Google home, Amazon Echo, on a display/screen, via a webpage/email/messaging system/notification system).

For example, when a user arrives home in his car, the task may be to, automatically, detect the user or his car approaching, open the garage door upon detection, turn on the driveway/garage light as the user approaches the garage, turn on air conditioner/heater/fan, etc. As the user enters the house, the task may be to, automatically, turn on the entrance light, turn off driveway/garage light, play a greeting message to welcome the user, turn on the music, turn on the radio and tuning to the user's favorite radio news channel, open the curtain/blind, monitor the user's mood, adjust the lighting and sound environment according to the user's mood or the current/imminent event (e.g. do romantic lighting and music because the user is scheduled to eat dinner with girlfriend in 1 hour) on the user's daily calendar, warm the food in microwave that the user prepared in the morning, do a diagnostic check of all systems in the house, check weather forecast for tomorrow's work, check news of interest to the user, check user's calendar and to-do list and play reminder, check telephone answer system/messaging system/email and give a verbal report using dialog system/speech synthesis, remind (e.g. using audible tool such as speakers/HiFi/speech synthesis/sound/voice/music/song/sound field/background sound field/dialog system, using visual tool such as TV/entertainment system/computer/notebook/smart pad/display/light/color/brightness/patterns/symbols, using haptic tool/virtual reality tool/gesture/tool, using a smart device/appliance/material/furniture/fixture, using web tool/server/hub device/cloud server/fog server/edge server/home network/mesh network, using messaging tool/notification tool/communication tool/scheduling tool/email, using user interface/GUI, using scent/smell/fragrance/taste, using neural tool/nervous system tool, using a combination) the user of his mother's birthday and to call her, prepare a report, and give the report (e.g. using a tool for reminding as discussed above). The task may turn on the air conditioner/heater/ventilation system in advance, or adjust temperature setting of smart thermostat in advance, etc. As the user moves from the entrance to the living room, the task may be to turn on the living room light, open the living room curtain, open the window, turn off the entrance light behind the user, turn on the TV and set-top box, set TV to the user's favorite channel, adjust an appliance according to the user's preference and conditions/states (e.g. adjust lighting and choose/play music to build a romantic atmosphere), etc.

Another example may be: When the user wakes up in the morning, the task may be to detect the user moving around in the bedroom, open the blind/curtain, open the window, turn off the alarm clock, adjust indoor temperature from night-time temperature profile to day-time temperature profile, turn on the bedroom light, turn on the restroom light as the user approaches the restroom, check radio or streaming channel and play morning news, turn on the coffee machine and preheat the water, turn off security system, etc. When the user walks from bedroom to kitchen, the task may be to turn on the kitchen and hallway lights, turn off the bedroom and restroom lights, move the music/message/reminder from the bedroom to the kitchen, turn on the kitchen TV, change TV to morning news channel, lower the kitchen blind and open the kitchen window to bring in fresh air, unlock backdoor for the user to check the backyard, adjust temperature setting for the kitchen, etc. Another example may be: When the user leaves home for work, the task may be to detect the user leaving, play a farewell and/or have-a-good-day message, open/close garage door, turn on/off garage light and driveway light, turn off/dim lights to save energy (just in case the user forgets), close/lock all windows/doors (just in case the user forgets), turn off appliance (especially stove, oven, microwave oven), turn on/arm the home security system to guard the home against any intruder, adjust air conditioning/heating/ventilation systems to "away-from-home" profile to save energy, send alerts/reports/updates to the user's smart phone, etc.

A motion may comprise at least one of: a no-motion, resting motion, non-moving motion, movement, change in position/location, deterministic motion, transient motion, fall-down motion, repeating motion, periodic motion, pseudo-periodic motion, periodic/repeated motion associated with breathing, periodic/repeated motion associated with heartbeat, periodic/repeated motion associated with living object, periodic/repeated motion associated with machine, periodic/repeated motion associated with man-made object, periodic/repeated motion associated with nature, complex motion with transient element and periodic element, repetitive motion, non-deterministic motion, probabilistic motion, chaotic motion, random motion, complex motion with non-deterministic element and deterministic element, stationary random motion, pseudo-stationary random motion, cyclo-stationary random motion, non-stationary random motion, stationary random motion with periodic autocorrelation function (ACF), random motion with periodic ACF for period of time, random motion that is pseudo-stationary for a period of time, random motion of which an instantaneous ACF has a pseudo-periodic/repeating element for a period of time, machine motion, mechanical motion, vehicle motion, drone motion, air-related motion, wind-related motion, weather-related motion, water-related motion, fluid-related motion, ground-related motion, change in electro-magnetic characteristics, subsurface motion, seismic motion, plant motion, animal motion, human motion, normal motion, abnormal motion, dangerous motion, warning motion, suspicious motion, rain, fire, flood, tsunami, explosion, collision, imminent collision, human body motion, head motion, facial motion, eye motion, mouth motion, tongue motion, neck motion, finger motion, hand motion, arm motion, shoulder motion, body motion, chest motion, abdominal motion, hip motion, leg motion, foot motion, body joint motion, knee motion, elbow motion, upper body motion, lower body motion, skin motion, below-skin motion, subcutaneous tissue motion, blood vessel motion, intravenous motion, organ motion, heart motion, lung motion, stomach motion, intestine motion, bowel motion, eating motion, breathing motion, facial expression, eye expression, mouth expression, talking motion, singing motion, eating motion, gesture, hand gesture, arm gesture, keystroke, typing stroke, user-interface gesture, man-machine interaction, gait, dancing movement, coordinated movement, and/or coordinated body movement.

The heterogeneous IC of the Type 1 device and/or any Type 2 receiver may comprise low-noise amplifier (LNA), power amplifier, transmit-receive switch, media access controller, baseband radio, 2.4 GHz radio, 3.65 GHz radio, 4.9 GHz radio, 5 GHz radio, 5.9 GHz radio, below 6 GHz radio, below 60 GHz radio and/or another radio. The heterogeneous IC may comprise a processor, a memory communicatively coupled with the processor, and a set of instructions stored in the memory to be executed by the processor. The IC and/or any processor may comprise at least one of: general purpose processor, special purpose processor, microprocessor, multi-processor, multi-core processor, parallel processor, CISC processor, RISC processor, microcontroller, central processing unit (CPU), graphical processor unit (GPU), digital signal processor (DSP), application specific integrated circuit (ASIC), field programmable gate array (FPGA), embedded processor (e.g. ARM), logic circuit, other programmable logic device, discrete logic, and/or a combination. The heterogeneous IC may support broadband network, wireless network, mobile network, mesh network, cellular network, wireless local area network (WLAN), wide area network (WAN), and metropolitan area network (MAN), WLAN standard, WiFi, LTE, LTE-A, LTE-U, 802.11 standard, 802.11a, 802.11b, 802.11g, 802.11n, 802.11ac, 802.11ad, 802.11af, 802.11ah, 802.11ax, 802.11ay, mesh network standard, 802.15 standard, 802.16 standard, cellular network standard, 3G, 3.5G, 4G, beyond 4G, 4.5G, 5G, 6G, 7G, 8G, 9G, UMTS, 3GPP, GSM, EDGE, TDMA, FDMA, CDMA, WCDMA, TD-SCDMA, Bluetooth, Bluetooth Low-Energy (BLE), NFC, Zigbee, WiMax, and/or another wireless network protocol.

The processor may comprise general purpose processor, special purpose processor, microprocessor, microcontroller, embedded processor, digital signal processor, central processing unit (CPU), graphical processing unit (GPU), multi-processor, multi-core processor, and/or processor with graphics capability, and/or a combination. The memory may be volatile, non-volatile, random access memory (RAM), Read Only Memory (ROM), Electrically Programmable ROM (EPROM), Electrically Erasable Programmable ROM (EEPROM), hard disk, flash memory, CD-ROM, DVD-ROM, magnetic storage, optical storage, organic storage, storage system, storage network, network storage, cloud storage, edge storage, local storage, external storage, internal storage, or other form of non-transitory storage medium known in the art. The set of instructions (machine executable code) corresponding to the method steps may be embodied directly in hardware, in software, in firmware, or in combinations thereof. The set of instructions may be embedded, pre-loaded, loaded upon boot up, loaded on the fly, loaded on demand, pre-installed, installed, and/or downloaded.

The presentation may be a presentation in an audio-visual way (e.g. using combination of visual, graphics, text, symbols, color, shades, video, animation, sound, speech, audio, etc.), graphical way (e.g. using GUI, animation, video), textual way (e.g. webpage with text, message, animated text), symbolic way (e.g. emoticon, signs, hand gesture), or mechanical way (e.g. vibration, actuator movement, haptics, etc.).

Basic Computation

Computational workload associated with the method is shared among the processor, the Type 1 heterogeneous wireless device, the Type 2 heterogeneous wireless device, a local server (e.g. hub device), a cloud server, and another processor.

An operation, pre-processing, processing and/or postprocessing may be applied to data (e.g. TSCI, autocorrelation, features of TSCI). An operation may be preprocessing, processing and/or postprocessing. The preprocessing, processing and/or postprocessing may be an operation. An operation may comprise preprocessing, processing, post-processing, scaling, computing a confidence factor, computing a line-of-sight (LOS) quantity, computing a non-LOS (NLOS) quantity, a quantity comprising LOS and NLOS, computing a single link (e.g. path, communication path, link between a transmitting antenna and a receiving antenna) quantity, computing a quantity comprising multiple links, computing a function of the operands, filtering, linear filtering, nonlinear filtering, folding, grouping, energy computation, lowpass filtering, bandpass filtering, highpass filtering, median filtering, rank filtering, quartile filtering, percentile filtering, mode filtering, finite impulse response (FIR) filtering, infinite impulse response (IIR) filtering, moving average (MA) filtering, autoregressive (AR) filtering, autoregressive moving averaging (ARMA) filtering, selective filtering, adaptive filtering, interpolation, decimation, subsampling, upsampling, resampling, time correction, time base correction, phase correction, magnitude correction, phase cleaning, magnitude cleaning, matched filtering, enhancement, restoration, denoising, smoothing, signal conditioning, enhancement, restoration, spectral analysis, linear transform, nonlinear transform, inverse transform, frequency transform, inverse frequency transform, Fourier transform (FT), discrete time FT (DTFT), discrete FT (DFT), fast FT (FFT), wavelet transform, Laplace transform, Hilbert transform, Hadamard transform, trigonometric transform, sine transform, cosine transform, DCT, power-of-2 transform, sparse transform, graph-based transform, graph signal processing, fast transform, a transform combined with zero padding, cyclic padding, padding, zero padding, feature extraction, decomposition, projection, orthogonal projection, non-orthogonal projection, over-complete projection, eigen-decomposition, singular value decomposition (SVD), principle component analysis (PCA), independent component analysis (ICA), grouping, sorting, thresholding, soft thresholding, hard thresholding, clipping, soft clipping, first derivative, second order derivative, high order derivative, convolution, multiplication, division, addition, subtraction, integration, maximization, minimization, least mean square error, recursive least square, constrained least square, batch least square, least absolute error, least mean square deviation, least absolute deviation, local maximization, local minimization, optimization of a cost function, neural network, recognition, labeling, training, clustering, machine learning, supervised learning, unsupervised learning, semi-supervised learning, comparison with another TSCI, similarity score computation, quantization, vector quantization, matching pursuit, compression, encryption, coding, storing, transmitting, normalization, temporal normalization, frequency domain normalization, classification, clustering, labeling, tagging, learning, detection, estimation, learning network, mapping, remapping, expansion, storing, retrieving, transmitting, receiving, representing, merging, combining, splitting, tracking, monitoring, matched filtering, Kalman filtering, particle filter, intrapolation, extrapolation, histogram estimation, importance sampling, Monte Carlo sampling, compressive sensing, representing, merging, combining, splitting, scrambling, error protection, forward error correction, doing nothing, time varying processing, conditioning averaging, weighted averaging, arithmetic mean, geometric mean, harmonic mean, averaging over selected frequency, averaging over antenna links, logical operation, permutation, combination, sorting, AND, OR, XOR, union, intersection, vector addition, vector subtraction, vector multiplication, vector division, inverse, norm, distance, and/or another operation. The operation may be the preprocessing, processing, and/or post-processing. Operations may be applied jointly on multiple time series or functions.

The function (e.g. function of operands) may comprise: scalar function, vector function, discrete function, continuous function, polynomial function, characteristics, feature, magnitude, phase, exponential function, logarithmic function, trigonometric function, transcendental function, logical function, linear function, algebraic function, nonlinear function, piecewise linear function, real function, complex function, vector-valued function, inverse function, derivative of function, integration of function, circular function, function of another function, one-to-one function, one-to-many function, many-to-one function, many-to-many function, zero crossing, absolute function, indicator function, mean, mode, median, range, statistics, histogram, variance, standard deviation, measure of variation, spread, dispersion, deviation, divergence, range, interquartile range, total variation, absolute deviation, total deviation, arithmetic mean, geometric mean, harmonic mean, trimmed mean, percentile, square, cube, root, power, sine, cosine, tangent, cotangent, secant, cosecant, elliptical function, parabolic function, hyperbolic function, game function, zeta function, absolute value, thresholding, limiting function, floor function, rounding function, sign function, quantization, piecewise constant function, composite function, function of function, time function processed with an operation (e.g. filtering), probabilistic function, stochastic function, random function, ergodic function, stationary function, deterministic function, periodic function, repeated function, transformation, frequency transform, inverse frequency transform, discrete time transform, Laplace transform, Hilbert transform, sine transform, cosine transform, triangular transform, wavelet transform, integer transform, power-of-2 transform, sparse transform, projection, decomposition, principle component analysis (PCA), independent component analysis (ICA), neural network, feature extraction, moving function, function of moving window of neighboring items of time series, filtering function, convolution, mean function, histogram, variance/standard deviation function, statistical function, short-time transform, discrete transform, discrete Fourier transform, discrete cosine transform, discrete sine transform, Hadamard transform, eigen-decomposition, eigenvalue, singular value decomposition (SVD), singular value, orthogonal decomposition, matching pursuit, sparse transform, sparse approximation, any decomposition, graph-based processing, graph-based transform, graph signal processing, classification, identifying a class/group/category, labeling, learning, machine learning, detection, estimation, feature extraction, learning network, feature extraction, denoising, signal enhancement, coding, encryption, mapping, remapping, vector quantization, lowpass filtering, highpass filtering, bandpass filtering, matched filtering, Kalman filtering, preprocessing, postprocessing, particle filter, FIR filtering, IIR filtering, autoregressive (AR) filtering, adaptive filtering, first order derivative, high order derivative, integration, zero crossing, smoothing, median filtering, mode filtering, sampling, random sampling, resampling function, downsampling, down-converting, upsampling, up-converting, interpolation, extrapolation, importance sampling, Monte Carlo sampling, compressive sensing, statistics, short term statistics, long term statistics, autocorrelation function, cross correlation, moment generating function, time averaging, weighted averaging, special function, Bessel function, error function, complementary error function, Beta function, Gamma function, integral function, Gaussian function, Poisson function, etc.

Machine learning, training, discriminative training, deep learning, neural network, continuous time processing, distributed computing, distributed storage, acceleration using GPU/DSP/coprocessor/multicore/multiprocessing may be applied to a step (or each step) of this disclosure.

A frequency transform may include Fourier transform, Laplace transform, Hadamard transform, Hilbert transform, sine transform, cosine transform, triangular transform, wavelet transform, integer transform, power-of-2 transform, combined zero padding and transform, Fourier transform with zero padding, and/or another transform. Fast versions and/or approximated versions of the transform may be performed. The transform may be performed using floating point, and/or fixed point arithmetic.

An inverse frequency transform may include inverse Fourier transform, inverse Laplace transform, inverse Hadamard transform, inverse Hilbert transform, inverse sine transform, inverse cosine transform, inverse triangular transform, inverse wavelet transform, inverse integer transform, inverse power-of-2 transform, combined zero padding and transform, inverse Fourier transform with zero padding, and/or another transform. Fast versions and/or approximated versions of the transform may be performed. The transform may be performed using floating point, and/or fixed point arithmetic.

A quantity/feature from a TSCI may be computed. The quantity may comprise statistic of at least one of: motion, location, map coordinate, height, speed, acceleration, movement angle, rotation, size, volume, time trend, pattern, one-time pattern, repeating pattern, evolving pattern, time pattern, mutually excluding patterns, related/correlated patterns, cause-and-effect, correlation, short-term/long-term correlation, tendency, inclination, statistics, typical behavior, atypical behavior, time trend, time profile, periodic motion, repeated motion, repetition, tendency, change, abrupt change, gradual change, frequency, transient, breathing, gait, action, event, suspicious event, dangerous event, alarming event, warning, belief, proximity, collision, power, signal, signal power, signal strength, signal intensity, received signal strength indicator (RSSI), signal amplitude, signal phase, signal frequency component, signal frequency band component, channel state information (CSI), map, time, frequency, time-frequency, decomposition, orthogonal decomposition, non-orthogonal decomposition, tracking, breathing, heart beat, statistical parameters, cardiopulmonary statistics/analytics (e.g. output responses), daily activity statistics/analytics, chronic disease statistics/analytics, medical statistics/analytics, an early (or instantaneous or contemporaneous or delayed) indication/suggestion/sign/indicator/verifier/detection/symptom of a disease/condition/situation, biometric, baby, patient, machine, device, temperature, vehicle, parking lot, venue, lift, elevator, spatial, road, fluid flow, home, room, office, house, building, warehouse, storage, system, ventilation, fan, pipe, duct, people, human, car, boat, truck, airplane, drone, downtown, crowd, impulsive event, cyclo-stationary, environment, vibration, material, surface, 3-dimensional, 2-dimensional, local, global, presence, and/or another measurable quantity/variable.

Sliding Window/Algorithm

Sliding time window may have time varying window width. It may be smaller at the beginning to enable fast acquisition and may increase over time to a steady-state size. The steady-state size may be related to the frequency, repeated motion, transient motion, and/or STI to be monitored. Even in steady state, the window size may be adaptively (and/or dynamically) changed (e.g. adjusted, varied, modified) based on battery life, power consumption, available computing power, change in amount of targets, the nature of motion to be monitored, etc.

The time shift between two sliding time windows at adjacent time instance may be constant/variable/locally adaptive/dynamically adjusted over time. When shorter time shift is used, the update of any monitoring may be more frequent which may be used for fast changing situations, object motions, and/or objects. Longer time shift may be used for slower situations, object motions, and/or objects.

The window width/size and/or time shift may be changed (e.g. adjusted, varied, modified) upon a user request/choice. The time shift may be changed automatically (e.g. as controlled by processor/computer/server/hub device/cloud server) and/or adaptively (and/or dynamically).

At least one characteristics (e.g. characteristic value, or characteristic point) of a function (e.g. auto-correlation function, auto-covariance function, cross-correlation function, cross-covariance function, power spectral density, time function, frequency domain function, frequency transform) may be determined (e.g. by an object tracking server, the processor, the Type 1 heterogeneous device, the Type 2 heterogeneous device, and/or another device). The at least one characteristics of the function may include: a maximum, minimum, extremum, local maximum, local minimum, local extremum, local extremum with positive time offset, first local extremum with positive time offset, nˆth local extremum with positive time offset, local extremum with negative time offset, first local extremum with negative time offset, nˆth local extremum with negative time offset, constrained maximum, constrained minimum, constrained extremum, significant maximum, significant minimum, significant extremum, slope, derivative, higher order derivative, maximum slope, minimum slope, local maximum slope, local maximum slope with positive time offset, local minimum slope, constrained maximum slope, constrained minimum slope, maximum higher order derivative, minimum higher order derivative, constrained higher order derivative, zero-crossing, zero crossing with positive time offset, nˆth zero crossing with positive time offset, zero crossing with negative time offset, nˆth zero crossing with negative time offset, constrained zero-crossing, zero-crossing of slope, zero-crossing of higher order derivative, and/or another characteristics. At least one argument of the function associated with the at least one characteristics of the function may be identified. Some quantity (e.g. spatial-temporal information of the object) may be determined based on the at least one argument of the function.

A characteristics (e.g. characteristics of motion of an object in the venue) may comprise at least one of: an instantaneous characteristics, short-term characteristics, repetitive characteristics, recurring characteristics, history, incremental characteristics, changing characteristics, deviational characteristics, phase, magnitude, degree, time characteristics, frequency characteristics, time-frequency characteristics, decomposition characteristics, orthogonal decomposition characteristics, non-orthogonal decomposition characteristics, deterministic characteristics, probabilistic characteristics, stochastic characteristics, autocorrelation function (ACF), mean, variance, standard deviation, measure of variation, spread, dispersion, deviation, divergence, range, interquartile range, total variation, absolute deviation, total deviation, statistics, duration, timing, trend, periodic characteristics, repetition characteristics, long-term characteristics, historical characteristics, average characteristics, current characteristics, past characteristics, future characteristics, predicted characteristics, location, distance, height, speed, direction, velocity, acceleration, change of the acceleration, angle, angular speed, angular velocity, angular acceleration of the object, change of the angular acceleration, orientation of the object, angular of rotation, deformation of the object, shape of the object, change of shape of the object, change of size of the object, change of structure of the object, and/or change of characteristics of the object.

At least one local maximum and at least one local minimum of the function may be identified. At least one local signal-to-noise-ratio-like (SNR-like) parameter may be computed for each pair of adjacent local maximum and local minimum. The SNR-like parameter may be a function (e.g. linear, log, exponential function, monotonic function) of a fraction of a quantity (e.g. power, magnitude) of the local maximum over the same quantity of the local minimum. It may also be the function of a difference between the quantity of the local maximum and the same quantity of the local minimum. Significant local peaks may be identified or selected. Each significant local peak may be a local maximum with SNR-like parameter greater than a threshold T1 and/or a local maximum with amplitude greater than a threshold T2. The at least one local minimum and the at least one local minimum in the frequency domain may be identified/computed using a persistence-based approach.

A set of selected significant local peaks may be selected from the set of identified significant local peaks based on a selection criterion (e.g. a quality criterion, a signal quality condition). The characteristics/STI of the object may be computed based on the set of selected significant local peaks and frequency values associated with the set of selected significant local peaks. In one example, the selection criterion may always correspond to select the strongest peaks in a range. While the strongest peaks may be selected, the unselected peaks may still be significant (rather strong).

Unselected significant peaks may be stored and/or monitored as "reserved" peaks for use in future selection in future sliding time windows. As an example, there may be a particular peak (at a particular frequency) appearing consistently over time. Initially, it may be significant but not selected (as other peaks may be stronger). But in later time, the peak may become stronger and more dominant and may be selected. When it became "selected", it may be back-traced in time and made "selected" in the earlier time when it was significant but not selected. In such case, the back-traced peak may replace a previously selected peak in an early time. The replaced peak may be the relatively weakest, or a peak that appear in isolation in time (i.e. appearing only briefly in time).

In another example, the selection criterion may not correspond to select the strongest peaks in the range. Instead, it may consider not only the "strength" of the peak, but the "trace" of the peak—peaks that may have happened in the past, especially those peaks that have been identified for a long time.

For example, if a finite state machine (FSM) is used, it may select the peak(s) based on the state of the FSM. Decision thresholds may be computed adaptively (and/or dynamically) based on the state of the FSM.

A similarity score and/or component similarity score may be computed (e.g. by a server (e.g. hub device), the processor, the Type 1 device, the Type 2 device, a local server, a cloud server, and/or another device) based on a pair of temporally adjacent CI of a TSCI. The pair may come from the same sliding window or two different sliding windows. The similarity score may also be based on a pair of, temporally adjacent or not so adjacent, CI from two different TSCI. The similarity score and/or component similar score may be/comprise: time reversal resonating strength (TRRS), correlation, cross-correlation, auto-correlation, correlation indicator, covariance, cross-covariance, auto-covariance, inner product of two vectors, distance score, norm, metric, quality metric, signal quality condition, statistical characteristics, discrimination score, neural network, deep learning network, machine learning, training, discrimination, weighted averaging, preprocessing, denoising, signal conditioning, filtering, time correction, timing compensation, phase offset compensation, transformation, component-wise operation, feature extraction, finite state machine, and/or another score. The characteristics and/or STI may be determined/computed based on the similarity score.

Any threshold may be pre-determined, adaptively (and/or dynamically) determined and/or determined by a finite state machine. The adaptive determination may be based on time, space, location, antenna, path, link, state, battery life, remaining battery life, available power, available computational resources, available network bandwidth, etc.

A threshold to be applied to a test statistics to differentiate two events (or two conditions, or two situations, or two states), A and B, may be determined. Data (e.g. CI, channel state information (CSI), power parameter) may be collected under A and/or under B in a training situation. The test statistics may be computed based on the data. Distributions of the test statistics under A may be compared with distributions of the test statistics under B (reference distribution), and the threshold may be chosen according to some criteria. The criteria may comprise: maximum likelihood (ML), maximum aposterior probability (MAP), discriminative training, minimum Type 1 error for a given Type 2 error, minimum Type 2 error for a given Type 1 error, and/or other criteria (e.g. a quality criterion, signal quality condition). The threshold may be adjusted to achieve different sensitivity to the A, B and/or another event/condition/situation/state. The threshold adjustment may be automatic, semi-automatic and/or manual. The threshold adjustment may be applied once, sometimes, often, periodically, repeatedly, occasionally, sporadically, and/or on demand. The threshold adjustment may be adaptive (and/or dynamically adjusted). The threshold adjustment may depend on the object, object movement/location/direction/action, object characteristics/ STI/size/property/trait/habit/behavior, the venue, feature/ fixture/furniture/barrier/material/machine/living thing/ thing/object/boundary/surface/medium that is in/at/of the venue, map, constraint of the map (or environmental model), the event/state/situation/condition, time, timing, duration, current state, past history, user, and/or a personal preference, etc.

A stopping criterion (or skipping or bypassing or blocking or pausing or passing or rejecting criterion) of an iterative algorithm may be that change of a current parameter (e.g. offset value) in the updating in an iteration is less than a threshold. The threshold may be 0.5, 1, 1.5, 2, or another number. The threshold may be adaptive (and/or dynamically adjusted). It may change as the iteration progresses. For the offset value, the adaptive threshold may be determined based on the task, particular value of the first time, the current time offset value, the regression window, the regression analysis, the regression function, the regression error, the convexity of the regression function, and/or an iteration number.

The local extremum may be determined as the corresponding extremum of the regression function in the regression window. The local extremum may be determined based on a set of time offset values in the regression window and a set of associated regression function values. Each of the set of associated regression function values associated with the set of time offset values may be within a range from the corresponding extremum of the regression function in the regression window.

The searching for a local extremum may comprise robust search, minimization, maximization, optimization, statistical optimization, dual optimization, constraint optimization, convex optimization, global optimization, local optimization an energy minimization, linear regression, quadratic regression, higher order regression, linear programming, nonlinear programming, stochastic programming, combinatorial optimization, constraint programming, constraint satisfaction, calculus of variations, optimal control, dynamic programming, mathematical programming, multi-objective optimization, multi-modal optimization, disjunctive programming, space mapping, infinite-dimensional optimization, heuristics, metaheuristics, convex programming, semidefinite programming, conic programming, cone programming, integer programming, quadratic programming, fractional programming, numerical analysis, simplex algorithm, iterative method, gradient descent, subgradient method, coordinate descent, conjugate gradient method, Newton's algorithm, sequential quadratic programming, interior point method, ellipsoid method, reduced gradient method, quasi-Newton method, simultaneous perturbation stochastic approximation, interpolation method, pattern search method, line search, non-differentiable optimization, genetic algorithm, evolutionary algorithm, dynamic relaxation, hill climbing, particle swarm optimization, gravitation search algorithm, simulated annealing, memetic algorithm, differential evolution, dynamic relaxation, stochastic tunneling, Tabu search, reactive search optimization, curve fitting, least square, simulation based optimization, variational calculus, and/or variant. The search for local extremum may be associated with an objective function, loss function, cost function, utility function, fitness function, energy function, and/or an energy function.

Regression may be performed using regression function to fit sampled data (e.g. CI, feature of CI, component of CI) or another function (e.g. autocorrelation function) in a regression window. In at least one iteration, a length of the regression window and/or a location of the regression window may change. The regression function may be linear function, quadratic function, cubic function, polynomial function, and/or another function.

The regression analysis may minimize at least one of: error, aggregate error, component error, error in projection domain, error in selected axes, error in selected orthogonal axes, absolute error, square error, absolute deviation, square deviation, higher order error (e.g. third order, fourth order), robust error (e.g. square error for smaller error magnitude and absolute error for larger error magnitude, or first kind of error for smaller error magnitude and second kind of error for larger error magnitude), another error, weighted sum (or weighted mean) of absolute/square error (e.g. for wireless transmitter with multiple antennas and wireless receiver with multiple antennas, each pair of transmitter antenna and receiver antenna form a link), mean absolute error, mean square error, mean absolute deviation, and/or mean square deviation. Error associated with different links may have different weights. One possibility is that some links and/or some components with larger noise or lower signal quality metric may have smaller or bigger weight), weighted sum of square error, weighted sum of higher order error, weighted sum of robust error, weighted sum of the another error, absolute cost, square cost, higher order cost, robust cost, another cost, weighted sum of absolute cost, weighted sum of square cost, weighted sum of higher order cost, weighted sum of robust cost, and/or weighted sum of another cost.

The regression error determined may be an absolute error, square error, higher order error, robust error, yet another error, weighted sum of absolute error, weighted sum of square error, weighted sum of higher order error, weighted sum of robust error, and/or weighted sum of the yet another error.

The time offset associated with maximum regression error (or minimum regression error) of the regression function with respect to the particular function in the regression window may become the updated current time offset in the iteration.

A local extremum may be searched based on a quantity comprising a difference of two different errors (e.g. a difference between absolute error and square error). Each of the two different errors may comprise an absolute error, square error, higher order error, robust error, another error, weighted sum of absolute error, weighted sum of square error, weighted sum of higher order error, weighted sum of robust error, and/or weighted sum of the another error.

The quantity may be compared with a reference data or a reference distribution, such as an F-distribution, central F-distribution, another statistical distribution, threshold, threshold associated with probability/histogram, threshold associated with probability/histogram of finding false peak, threshold associated with the F-distribution, threshold associated the central F-distribution, and/or threshold associated with the another statistical distribution.

The regression window may be determined based on at least one of: the movement (e.g. change in position/location) of the object, quantity associated with the object, the at least one characteristics and/or STI of the object associated with the movement of the object, estimated location of the local extremum, noise characteristics, estimated noise characteristics, signal quality metric, F-distribution, central F-distribution, another statistical distribution, threshold, preset threshold, threshold associated with probability/histogram, threshold associated with desired probability, threshold associated with probability of finding false peak, threshold associated with the F-distribution, threshold associated the central F-distribution, threshold associated with the another statistical distribution, condition that quantity at the window center is largest within the regression window, condition that the quantity at the window center is largest within the regression window, condition that there is only one of the local extremum of the particular function for the particular value of the first time in the regression window, another regression window, and/or another condition.

The width of the regression window may be determined based on the particular local extremum to be searched. The local extremum may comprise first local maximum, second local maximum, higher order local maximum, first local maximum with positive time offset value, second local maximum with positive time offset value, higher local maximum with positive time offset value, first local maximum with negative time offset value, second local maximum with negative time offset value, higher local maximum with negative time offset value, first local minimum, second local minimum, higher local minimum, first local minimum with positive time offset value, second local minimum with positive time offset value, higher local minimum with positive time offset value, first local minimum with negative time offset value, second local minimum with negative time offset value, higher local minimum with negative time offset value, first local extremum, second local extremum, higher local extremum, first local extremum with positive time offset value, second local extremum with positive time offset value, higher local extremum with positive time offset value, first local extremum with negative time offset value, second local extremum with negative time offset value, and/or higher local extremum with negative time offset value.

A current parameter (e.g. time offset value) may be initialized based on a target value, target profile, trend, past trend, current trend, target speed, speed profile, target speed profile, past speed trend, the motion or movement (e.g. change in position/location) of the object, at least one characteristics and/or STI of the object associated with the movement of object, positional quantity of the object, initial speed of the object associated with the movement of the object, predefined value, initial width of the regression window, time duration, value based on carrier frequency of the signal, value based on subcarrier frequency of the signal, bandwidth of the signal, amount of antennas associated with the channel, noise characteristics, signal h metric, and/or an adaptive (and/or dynamically adjusted) value. The current time offset may be at the center, on the left side, on the right side, and/or at another fixed relative location, of the regression window.

In the presentation, information may be displayed with a map (or environmental model) of the venue. The information may comprise: location, zone, region, area, coverage area, corrected location, approximate location, location with respect to (w.r.t.) a map of the venue, location w.r.t. a segmentation of the venue, direction, path, path w.r.t. the map and/or the segmentation, trace (e.g. location within a time window such as the past 5 seconds, or past 10 seconds; the time window duration may be adjusted adaptively (and/or dynamically); the time window duration may be adaptively (and/or dynamically) adjusted w.r.t. speed, acceleration, etc.), history of a path, approximate regions/zones along a path, history/summary of past locations, history of past locations of interest, frequently-visited areas, customer traffic, crowd distribution, crowd behavior, crowd control information, speed, acceleration, motion statistics, breathing rate, heart rate, presence/absence of motion, presence/absence of people or pets or object, presence/absence of vital sign, gesture, gesture control (control of devices using gesture), location-based gesture control, information of a location-based operation, identity (ID) or identifier of the respect object (e.g. pet, person, self-guided machine/device, vehicle, drone, car, boat, bicycle, self-guided vehicle, machine with fan, air-conditioner, TV, machine with movable part), identification of a user (e.g. person), information of the user, location/speed/acceleration/direction/motion/gesture/gesture control/motion trace of the user, ID or identifier of the user, activity of the user, state of the user, sleeping/resting characteristics of the user, emotional state of the user, vital sign of the user, environment information of the venue, weather information of the venue, earthquake, explosion, storm, rain, fire, temperature, collision, impact, vibration, event, door-open event, door-close event, window-open event, window-close event, fall-down event, burning event, freezing event, water-related event, wind-related event, air-movement event, accident event, pseudo-periodic event (e.g. running on treadmill, jumping up and down, skipping rope, somersault, etc.), repeated event, crowd event, vehicle event, gesture of the user (e.g. hand gesture, arm gesture, foot gesture, leg gesture, body gesture, head gesture, face gesture, mouth gesture, eye gesture, etc.).

The location may be 2-dimensional (e.g. with 2D coordinates), 3-dimensional (e.g. with 3D coordinates). The location may be relative (e.g. w.r.t. a map or environmental model) or relational (e.g. halfway between point A and point B, around a corner, up the stairs, on top of table, at the ceiling, on the floor, on a sofa, close to point A, a distance R from point A, within a radius of R from point A, etc.). The location may be expressed in rectangular coordinate, polar coordinate, and/or another representation.

The information (e.g. location) may be marked with at least one symbol. The symbol may be time varying. The symbol may be flashing and/or pulsating with or without changing color/intensity. The size may change over time. The orientation of the symbol may change over time. The symbol may be a number that reflects an instantaneous quantity (e.g. vital sign/breathing rate/heart rate/gesture/state/status/action/motion of a user, temperature, network traffic, network connectivity, status of a device/machine, remaining power of a device, status of the device, etc.). The rate of change, the size, the orientation, the color, the intensity and/or the symbol may reflect the respective motion. The information may be presented visually and/or described verbally (e.g. using pre-recorded voice, or voice synthesis). The information may be described in text. The information may also be presented in a mechanical way (e.g. an animated gadget, a movement of a movable part).

The user-interface (UI) device may be a smart phone (e.g. iPhone, Android phone), tablet (e.g. iPad), laptop (e.g. notebook computer), personal computer (PC), device with graphical user interface (GUI), smart speaker, device with voice/audio/speaker capability, virtual reality (VR) device, augmented reality (AR) device, smart car, display in the car, voice assistant, voice assistant in a car, etc.

The map (or environmental model) may be 2-dimensional, 3-dimensional and/or higher-dimensional. (e.g. a time varying 2D/3D map/environmental model) Walls, windows, doors, entrances, exits, forbidden areas may be marked on the map or the model. The map may comprise floor plan of a facility. The map or model may have one or more layers (overlays). The map/model may be a maintenance map/model comprising water pipes, gas pipes, wiring, cabling, air ducts, crawl-space, ceiling layout, and/or underground layout. The venue may be segmented/subdivided/zoned/grouped into multiple zones/regions/geographic regions/sectors/sections/territories/districts/precincts/localities/neighborhoods/areas/stretches/expanse such as bedroom, living room, storage room, walkway, kitchen, dining room, foyer, garage, first floor, second floor, rest room, offices, conference room, reception area, various office areas, various warehouse regions, various facility areas, etc. The segments/regions/areas may be presented in a map/model. Different regions may be color-coded. Different regions may be presented with a characteristic (e.g. color, brightness, color intensity, texture, animation, flashing, flashing rate, etc.). Logical segmentation of the venue may be done using the at least one heterogeneous Type 2 device, or a server (e.g. hub device), or a cloud server, etc.

Here is an example of the disclosed system, apparatus, and method. Stephen and his family want to install the disclosed wireless motion detection system to detect motion in their 2000 sqft two-storey town house in Seattle, Wash. Because his house has two storeys, Stephen decided to use one Type 2 device (named A) and two Type 1 devices (named B and C) in the ground floor. His ground floor has predominantly three rooms: kitchen, dining room and living room arranged in a straight line, with the dining room in the middle. The kitchen and the living rooms are on opposite end of the house. He put the Type 2 device (A) in the dining room, and put one Type 1 device (B) in the kitchen and the other Type 1 device (C) in the living room. With this placement of the devices, he is practically partitioning the ground floor into 3 zones (dining room, living room and kitchen) using the motion detection system. When motion is detected by the AB pair and the AC pair, the system would analyze the motion information and associate the motion with one of the 3 zones.

When Stephen and his family go out on weekends (e.g. to go for a camp during a long weekend), Stephen would use a mobile phone app (e.g. Android phone app or iPhone app) to turn on the motion detection system. When the system detects motion, a warning signal is sent to Stephen (e.g. an SMS text message, an email, a push message to the mobile phone app, etc.). If Stephen pays a monthly fee (e.g. $10/month), a service company (e.g. security company) will receive the warning signal through wired network (e.g. broadband) or wireless network (e.g. home WiFi, LTE, 3G, 2.5G, etc.) and perform a security procedure for Stephen (e.g. call him to verify any problem, send someone to check on the house, contact the police on behalf of Stephen, etc.). Stephen loves his aging mother and cares about her well-being when she is alone in the house. When the mother is alone in the house while the rest of the family is out (e.g. go to work, or shopping, or go on vacation), Stephen would turn on the motion detection system using his mobile app to ensure the mother is ok. He then uses the mobile app to monitor his mother's movement in the house. When Stephen uses the mobile app to see that the mother is moving around the house among the 3 regions, according to her daily routine, Stephen knows that his mother is doing ok. Stephen is thankful that the motion detection system can help him monitor his mother's well-being while he is away from the house.

On a typical day, the mother would wake up at around 7 AM. She would cook her breakfast in the kitchen for about 20 minutes. Then she would eat the breakfast in the dining room for about 30 minutes. Then she would do her daily exercise in the living room, before sitting down on the sofa in the living room to watch her favorite TV show. The motion detection system enables Stephen to see the timing of the movement in each of the 3 regions of the house. When the motion agrees with the daily routine, Stephen knows roughly that the mother should be doing fine. But when the motion pattern appears abnormal (e.g. there is no motion until 10 AM, or she stayed in the kitchen for too long, or she remains motionless for too long, etc.), Stephen suspects something is wrong and would call the mother to check on her. Stephen may even get someone (e.g. a family member, a neighbor, a paid personnel, a friend, a social worker, a service provider) to check on his mother.

At some time, Stephen feels like repositioning the Type 2 device. He simply unplugs the device from the original AC power plug and plug it into another AC power plug. He is happy that the wireless motion detection system is plug-and-play and the repositioning does not affect the operation of the system. Upon powering up, it works right away.

Sometime later, Stephen is convinced that our wireless motion detection system can really detect motion with very high accuracy and very low alarm, and he really can use the mobile app to monitor the motion in the ground floor. He decides to install a similar setup (i.e. one Type 2 device and two Type 1 devices) in the second floor to monitor the bedrooms in the second floor. Once again, he finds that the system set up is extremely easy as he simply needs to plug the Type 2 device and the Type 1 devices into the AC power plug in the second floor. No special installation is needed. And he can use the same mobile app to monitor motion in the ground floor and the second floor. Each Type 2 device in the ground floor/second floor can interact with all the Type 1 devices in both the ground floor and the second floor. Stephen is happy to see that, as he doubles his investment in the Type 1 and Type 2 devices, he has more than double the capability of the combined systems.

According to various embodiments, each CI (CI) may comprise at least one of: channel state information (CSI), frequency domain CSI, frequency representation of CSI, frequency domain CSI associated with at least one sub-band, time domain CSI, CSI in domain, channel response, estimated channel response, channel impulse response (CIR), channel frequency response (CFR), channel characteristics, channel filter response, CSI of the wireless multipath channel, information of the wireless multipath channel, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another CI. In one embodiment, the disclosed system has hardware components (e.g. wireless transmitter/receiver with antenna, analog circuitry, power supply, processor, memory) and corresponding software components. According to various embodiments of the present teaching, the disclosed system includes Bot (referred to as a Type 1 device) and Origin (referred to as a Type 2 device) for vital sign detection and monitoring. Each device comprises a transceiver, a processor and a memory.

The disclosed system can be applied in many cases. In one example, the Type 1 device (transmitter) may be a small WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. In one example, the Type 2 (receiver) may be a WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. The Type 1 device and Type 2 devices may be placed in/near a conference room to count people. The Type 1 device and Type 2 devices may be in a well-being monitoring system for older adults to monitor their daily activities and any sign of symptoms (e.g. dementia, Alzheimer's disease). The Type 1 device and Type 2 device may be used in baby monitors to monitor the vital signs (breathing) of a living baby. The Type 1 device and Type 2 devices may be placed in bedrooms to monitor quality of sleep and any sleep apnea. The Type 1 device and Type 2 devices may be placed in cars to monitor well-being of passengers and driver, detect any sleeping of driver and detect any babies left in a car. The Type 1 device and Type 2 devices may be used in logistics to prevent human trafficking by monitoring any human hidden in trucks and containers. The Type 1 device and Type 2 devices may be deployed by emergency service at disaster area to search for trapped victims in debris. The Type 1 device and Type 2 devices may be deployed in an area to detect breathing of any intruders. There are numerous applications of wireless breathing monitoring without wearables.

Hardware modules may be constructed to contain the Type 1 transceiver and/or the Type 2 transceiver. The hardware modules may be sold to/used by variable brands to design, build and sell final commercial products. Products using the disclosed system and/or method may be home/office security products, sleep monitoring products, WiFi products, mesh products, TV, STB, entertainment system, HiFi, speaker, home appliance, lamps, stoves, oven, microwave oven, table, chair, bed, shelves, tools, utensils, torches, vacuum cleaner, smoke detector, sofa, piano, fan, door, window, door/window handle, locks, smoke detectors, car accessories, computing devices, office devices, air conditioner, heater, pipes, connectors, surveillance camera, access point, computing devices, mobile devices, LTE devices, 3G/4G/5G/6G devices, UMTS devices, 3GPP devices, GSM devices, EDGE devices, TDMA devices, FDMA devices, CDMA devices, WCDMA devices, TD-SCDMA devices, gaming devices, eyeglasses, glass panels, VR goggles, necklace, watch, waist band, belt, wallet, pen, hat, wearables, implantable device, tags, parking tickets, smart phones, etc.

The summary may comprise: analytics, output response, selected time window, subsampling, transform, and/or projection. The presenting may comprise presenting at least one of: monthly/weekly/daily view, simplified/detailed view, cross-sectional view, small/large form-factor view, color-coded view, comparative view, summary view, animation, web view, voice announcement, and another presentation related to the periodic/repetition characteristics of the repeating motion.

A Type 1/Type 2 device may be an antenna, a device with antenna, a device with a housing (e.g. for radio, antenna, data/signal processing unit, wireless IC, circuits), device that has interface to attach/connect to/link antenna, device that is interfaced to/attached to/connected to/linked to another device/system/computer/phone/network/data aggregator, device with a user interface (UI)/graphical UI/display, device with wireless transceiver, device with wireless transmitter, device with wireless receiver, internet-of-thing (IoT) device, device with wireless network, device with both wired networking and wireless networking capability, device with wireless integrated circuit (IC), Wi-Fi device, device with Wi-Fi chip (e.g. 802.11a/b/g/n/ac/ax standard compliant), Wi-Fi access point (AP), Wi-Fi client, Wi-Fi router, Wi-Fi repeater, Wi-Fi hub, Wi-Fi mesh network router/hub/AP, wireless mesh network router, adhoc network device, wireless mesh network device, mobile device (e.g. 2G/2.5G/3G/3.5G/4G/LTE/5G/6G/7G, UMTS, 3GPP, GSM, EDGE, TDMA, FDMA, CDMA, WCDMA, TD-SCDMA), cellular device, base station, mobile network base station, mobile network hub, mobile network compatible device, LTE device, device with LTE module, mobile module (e.g. circuit board with mobile-enabling chip (IC) such as Wi-Fi chip, LTE chip, BLE chip), Wi-Fi chip (IC), LTE chip, BLE chip, device with mobile module, smart phone, companion device (e.g. dongle, attachment, plugin) for smart phones, dedicated device, plug-in device, AC-powered device, battery-powered device, device with processor/memory/set of instructions, smart device/gadget/items: clock, stationary, pen, user-interface, paper, mat, camera, television (TV), set-top-box, microphone, speaker, refrigerator, oven, machine, phone, wallet, furniture, door, window, ceiling, floor, wall, table, chair, bed, night-stand, air-conditioner, heater, pipe, duct, cable, carpet, decoration, gadget, USB device, plug, dongle, lamp/light, tile, ornament, bottle, vehicle, car, AGV, drone, robot, laptop, tablet, computer, harddisk, network card, instrument, racket, ball, shoe, wearable, clothing, glasses, hat, necklace, food, pill, small device that moves in the body of creature (e.g. in blood vessels, in lymph fluid, digestive system), and/or another device. The Type 1 device and/or Type 2 device may be communicatively coupled with: the internet, another device with access to internet (e.g. smart phone), cloud server (e.g. hub device), edge server, local server, and/or storage. The Type 1 device and/or the Type 2 device may operate with local control, can be controlled by another device via a wired/wireless connection, can operate automatically, or can be controlled by a central system that is remote (e.g. away from home).

In one embodiment, a Type B device may be a transceiver that may perform as both Origin (a Type 2 device, a Rx device) and Bot (a Type 1 device, a Tx device), i.e., a Type B device may be both Type 1 (Tx) and Type 2 (Rx) devices (e.g. simultaneously or alternately), for example, mesh devices, a mesh router, etc. In one embodiment, a Type A device may be a transceiver that may only function as Bot (a Tx device), i.e., Type 1 device only or Tx only, e.g., simple IoT devices. It may have the capability of Origin (Type 2 device, Rx device), but somehow it is functioning only as Bot in the embodiment. All the Type A and Type B devices form a tree structure. The root may be a Type B device with network (e.g. internet) access. For example, it may be connected to broadband service through a wired connection (e.g. Ethernet, cable modem, ADSL/HDSL modem) connection or a wireless connection (e.g. LTE, 3G/4G/5G, WiFi, Bluetooth, microwave link, satellite link, etc.). In one embodiment, all the Type A devices are leaf node. Each Type B device may be the root node, non-leaf node, or leaf node.

Type 1 device (transmitter, or Tx) and Type 2 device (receiver, or Rx) may be on same device (e.g. RF chip/IC) or simply the same device. The devices may operate at high frequency band, such as 28 GHz, 60 GHz, 77 GHz, etc. The RF chip may have dedicated Tx antennas (e.g. 32 antennas) and dedicated Rx antennas (e.g. another 32 antennas).

One Tx antenna may transmit a wireless signal (e.g. a series of probe signal, perhaps at 100 Hz). Alternatively, all Tx antennas may be used to transmit the wireless signal with beamforming (in Tx), such that the wireless signal is focused in certain direction (e.g. for energy efficiency or boosting the signal to noise ratio in that direction, or low power operation when "scanning" that direction, or low power operation if object is known to be in that direction).

The wireless signal hits an object (e.g. a living human lying on a bed 4 feet away from the Tx/Rx antennas, with breathing and heart beat) in a venue (e.g. a room). The object motion (e.g. lung movement according to breathing rate, or blood-vessel movement according to heart beat) may impact/modulate the wireless signal. All Rx antennas may be used to receive the wireless signal.

Beamforming (in Rx and/or Tx) may be applied (digitally) to "scan" different directions. Many directions can be scanned or monitored simultaneously. With beamforming, "sectors" (e.g. directions, orientations, bearings, zones, regions, segments) may be defined related to the Type 2 device (e.g. relative to center location of antenna array). For each probe signal (e.g. a pulse, an ACK, a control packet, etc.), a channel information or CI (e.g. channel impulse response/CIR, CSI, CFR) is obtained/computed for each sector (e.g. from the RF chip). In breathing detection, one may collect CIR in a sliding window (e.g. 30 sec, and with 100 Hz sounding/probing rate, one may have 3000 CIR over 30 sec).

The CIR may have many taps (e.g. N1 components/taps). Each tap may be associated with a time lag, or a time-of-flight (tof, e.g. time to hit the human 4 feet away and back). When a person is breathing in a certain direction at a certain distance (e.g. 4 ft), one may search for the CIR in the "certain direction". Then one may search for the tap corresponding to the "certain distance". Then one may compute the breathing rate and heart rate from that tap of that CIR.

One may consider each tap in the sliding window (e.g. 30 second window of "component time series") as a time function (e.g. a "tap function", the "component time series"). One may examine each tap function in search of a strong periodic behavior (e.g. corresponds to breathing, perhaps in the range of 10 bpm to 40 bpm).

The Type 1 device and/or the Type 2 device may have external connections/links and/or internal connections/links. The external connections (e.g. connection 1110) may be associated with 2G/2.5G/3G/3.5G/4G/LTE/5G/6G/7G/NBIoT, UWB, WiMax, Zigbee, 802.16 etc. The internal connections (e.g., 1114A and 1114B, 1116, 1118, 1120) may be associated with WiFi, an IEEE 802.11 standard, 802.11a/b/g/n/ac/ad/af/ag/ah/ai/aj/aq/ax/ay, Bluetooth, Bluetooth 1.0/1.1/1.2/2.0/2.1/3.0/4.0/4.1/4.2/5, BLE, mesh network, an IEEE 802.16/1/1a/1b/2/2a/a/b/c/d/e/f/g/h/i/j/k/l/m/n/o/p/ standard.

The Type 1 device and/or Type 2 device may be powered by battery (e.g. AA battery, AAA battery, coin cell battery, button cell battery, miniature battery, bank of batteries, power bank, car battery, hybrid battery, vehicle battery, container battery, non-rechargeable battery, rechargeable battery, NiCd battery, NiMH battery, Lithium ion battery, Zinc carbon battery, Zinc chloride battery, lead acid battery, alkaline battery, battery with wireless charger, smart battery, solar battery, boat battery, plane battery, other battery, temporary energy storage device, capacitor, fly wheel).

Any device may be powered by DC or direct current (e.g. from battery as described above, power generator, power convertor, solar panel, rectifier, DC-DC converter, with various voltages such as 1.2V, 1.5V, 3V, 5V, 6V, 9V, 12V, 24V, 40V, 42V, 48V, 110V, 220V, 380V, etc.) and may thus have a DC connector or a connector with at least one pin for DC power.

Any device may be powered by AC or alternating current (e.g. wall socket in a home, transformer, invertor, shore-power, with various voltages such as 100V, 110V, 120V, 100-127V, 200V, 220V, 230V, 240V, 220-240V, 100-240V, 250V, 380V, 50 Hz, 60 Hz, etc.) and thus may have an AC connector or a connector with at least one pin for AC power. The Type 1 device and/or the Type 2 device may be positioned (e.g. installed, placed, moved to) in the venue or outside the venue.

For example, in a vehicle (e.g. a car, truck, lorry, bus, special vehicle, tractor, digger, excavator, teleporter, bulldozer, crane, forklift, electric trolley, AGV, emergency vehicle, freight, wagon, trailer, container, boat, ferry, ship, submersible, airplane, air-ship, lift, mono-rail, train, tram, rail-vehicle, railcar, etc.), the Type 1 device and/or Type 2 device may be an embedded device embedded in the vehicle, or an add-on device (e.g. aftermarket device) plugged into a port in the vehicle (e.g. OBD port/socket, USB port/socket, accessory port/socket, 12V auxiliary power outlet, and/or 12V cigarette lighter port/socket).

For example, one device (e.g. Type 2 device) may be plugged into 12V cigarette lighter/accessory port or OBD port or the USB port (e.g. of a car/truck/vehicle) while the other device (e.g. Type 1 device) may be plugged into 12V cigarette lighter/accessory port or the OBD port or the USB port. The OBD port and/or USB port can provide power, signaling and/or network (of the car/truck/vehicle). The two devices may jointly monitor the passengers including children/babies in the car. They may be used to count the passengers, recognize the driver, detect presence of passenger in a particular seat/position in the vehicle.

In another example, one device may be plugged into 12V cigarette lighter/accessory port or OBD port or the USB port of a car/truck/vehicle while the other device may be plugged into 12V cigarette lighter/accessory port or OBD port or the USB port of another car/truck/vehicle.

In another example, there may be many devices of the same type A (e.g. Type 1 or Type 2) in many heterogeneous vehicles/portable devices/smart gadgets (e.g. automated guided vehicle/AGV, shopping/luggage/moving cart, parking ticket, golf cart, bicycle, smart phone, tablet, camera, recording device, smart watch, roller skate, shoes, jackets, goggle, hat, eye-wear, wearable, Segway, scooter, luggage tag, cleaning machine, vacuum cleaner, pet tag/collar/wearable/implant), each device either plugged into 12V accessory port/OBD port/USB port of a vehicle or embedded in a vehicle. There may be one or more device of the other type B (e.g. B is Type 1 if A is Type 2, or B is Type 2 if A is Type 1) installed at locations such as gas stations, street lamp post, street corners, tunnels, multi-storey parking facility, scattered locations to cover a big area such as factory/stadium/train station/shopping mall/construction site. The Type A device may be located, tracked or monitored based on the TSCI.

The area/venue may have no local connectivity, e.g., broadband services, WiFi, etc. The Type 1 and/or Type 2 device may be portable. The Type 1 and/or Type 2 device may support plug and play.

Pairwise wireless links may be established between many pairs of devices, forming the tree structure. In each pair (and the associated link), a device (second device) may be a non-leaf (Type B). The other device (first device) may be a leaf (Type A or Type B) or non-leaf (Type B). In the link, the first device functions as a bot (Type 1 device or a Tx device) to send a wireless signal (e.g. probe signal) through the wireless multipath channel to the second device. The second device may function as an Origin (Type 2 device or Rx device) to receive the wireless signal, obtain the TSCI and compute a "linkwise analytics" based on the TSCI.

One goal of the present teaching is to enable contactless sleep monitoring on any low-cost, Wi-Fi-enabled IoT devices, including those having only a single antenna and on a 20 MHz 2.4 GHz channel. The state-of-the-art sleep monitoring algorithm estimates motion and breathing rates to infer and stage sleep. However, sleep estimation only works reliably on 5 GHz channels with 40 MHz or more bandwidths, and barely works for a 20 MHz 2.4 GHz channel. In some embodiments, the present teaching resorts to motion detection alone and circumvents the need of breathing estimation for sleep monitoring. Motion detection has demonstrated to be extremely efficient and accurate and can run on any IoTs. The key insight is that people make involuntary body movements during sleep (BMS), such as poster changes, limb movements, head movements, etc. These movements exhibit distinct behavioral patterns that are differentiable from voluntary motions in the day time. Albeit being occasional, instantaneous, and weak, these BMS can still be captured precisely by Wi-Fi-based motion detection. Based on this observation, the present teaching discloses AnySleep, a sleep monitoring system based on body movements during sleep, which can run on any Wi-Fi IoT devices.

In some embodiments, AnySleep first introduces a boosted motion indicator, named micromotion, which can capture tiny BMS motion more reliably than the existing motion statistics, while causing negligible computation overhead. Based on the time series of the detected motions, AnySleep first analyzes the presence and activeness of the user. It then detects BMS by investigating the unique behavioral patterns of typical BMS during night. The system may then calculate a BMS score, which is further refined as a sleep likelihood based on the estimated presence and activeness information. Finally, an iterative searching algorithm is designed to recognize the most likely period of sleep and use a heuristic metric to assess the sleep quality.

Behavioral quiescence, i.e., the absence of voluntary motor behavior, is an essential characteristic of sleep. However, people do move (quite a lot) during sleep, a fact that is elusive and somewhat counter-intuitive. Not only do we change sleep postures, but we also move our head, hands/arms, and legs, etc. All these lead to a considerable amount of movements, which can be termed as Body Movements during Sleep (BMS). According to clinical studies, healthy adults usually experience, in average, 10 times of major posture changes and tens of or even a few hundreds of minor body movements per night, which certainly vary over nights and across subjects.

In some embodiments, the disclosed motion detection may be based on WiDetect, which is the most sensitive and robust motion detector using WiFi signals that has been commercialized as real products. To capture the tiny involuntary motion during sleep, however, the system has enhanced WiDetect for micro motion detection by optimizing the motion sensitivity.

Given a wireless channel between a pair of Wi-Fi devices, the ideal CSI estimation for the subcarrier with frequency f measured at time t can be denoted as:

$$H(t, f) = \sum_{l=1}^{L} a_l(t) \exp(-j2\pi f \tau_l(t)),$$

where $a_l(t)$ and $\tau_l(t)$ denote the complex amplitude and propagation delay of the l-th multipath component, respectively. Due to timing and frequency synchronization errors in real Wi-Fi systems, the measured CSI contains significant phase offsets and becomes $$\tilde{H}(t,f) = \exp(-j(\alpha(t)+\beta(t)f))H(t,f)+n(t,f),$$

where $\alpha(t)$ and $\beta(t)$ are the random initial and linear phase offsets at time t, respectively. For brevity, H(t, f) is still used for the real measurement $\tilde{H}(t, f)$ hereafter.

As the phase information is severely distorted and is non-trivial to calibrate, one can mainly exploit the measured CSI amplitude for motion detection. Nevertheless, the derived motion statistics can be directly extended to incorporate phase information if it is properly cleaned. Denote the power response of a CSI measurement H(t, f) as $$G(t, f) \triangleq |H(t, f)|^2.$$

WiDetect defines a novel metric within the range of [0,1] to indicate the existence and strength of surrounding motion, which is termed as motion statistic and can be calculated from the auto-correlation function (ACF) of the CSI. Specifically, the motion statistic on subcarrier f is defined as (omitting the notion of time t for brevity):

$$\phi(f) = \lim_{\tau \to 0} \rho_G(\tau, f) \triangleq \rho_G\left(\tau = \frac{1}{F_s}, f\right). \quad (1)$$

Putting it simply, in presence of motion, one can have $\lim_{\tau \to 0} \rho_G(\tau, f) > 0$; while if there is no motion in the environment, $\lim_{\tau \to 0} \rho_G(\tau, f) = 0$. Therefore, $\lim_{\tau \to 0} \rho_G(\tau, f)$ provably, and also practically, embodies a good indicator for the presence of motion, which is only determined by the power response of the motion and the measurement noises and is independent of the environments, locations, orientations, and subjects, etc. In Eqn. (1), one can use the first sample of the ACF, $$\rho_G\left(\tau = \frac{1}{F_s}, f\right),$$

as an approximation of $\lim_{\tau \to 0} \rho_G(\tau, f)$ since the channel sampling rate is limited in practice. In some embodiments, the average over all subcarriers is taken as the overall motion statistic $$\phi = \frac{1}{F} \sum_{f=1}^{F} \phi(f)$$

so that a proper threshold for motion detection can be theoretically determined.

Depending on the placement of the devices and the distances from the subject to the transceivers, the averaged motion statistic may not be super sensitive to very tiny motion (e.g., small body movements during sleep) due to CSI measurement noises. Therefore, the system can maximize the motion signals so that the AnySleep system can reliably sense body motions during sleep. In some embodiments, maximal ratio combining (MRC) can be performed to optimally combine the motion statistics calculated on individual subcarriers, instead of the equal gain averaging. MRC is a general diversity fusion method that maximizes the SNR by combining multiple receiving signals in an optimal way, which has been widely used in wireless communication and, recently, wireless sensing. Particularly, the ACF on different subcarriers are inherently synchronized and independent from the time origin and that the noise variances for different subcarriers are the same, thus satisfying the conditions to apply MRC. Given a fixed number of F subcarriers, the motion signal will thus be maximized by combining the motion statistics as follows:

$$\varrho_G(\tau, f) = \sum_{f=1}^{F} w(f) \rho_G(\tau, f),$$

where w(f) denotes the optimal weight for combining multiple subcarriers, which depends on the channel gain. The calculated motion statistic itself can serve as the channel gain for each subcarrier, and therefore can be used as the optimal weights for combining, i.e., $$\varrho_G(\tau, f) = \sum_{f=1}^{F} \rho_G\left(\tau = \frac{1}{F_s}, f\right) \rho_G(\tau, f).$$

Then the boosted motion statistic for micro motion detection can be, again, estimated as the first sample of the maximized ACF $$\varphi = \varrho_G\left(\tau = \frac{1}{F_s}, f\right).$$

In practice, instead of fusing all F subcarriers, one may sort all $\rho_G(t, f)$ and select the K subcarriers of the largest motion statistics for MRC. This would further increase the values of the combined $\varrho_G(\tau, f)$.

One issue for the boosted signal is about the noise level in absence of motion. As mentioned earlier, the averaged motion statistic φ approximates 0 if no motion presents, and thus a theoretical threshold can be effectively obtained for motion detection. The optimized micro motion statistic φ, however, not only boosts the motion signal but also enlarges the noises (including environmental dynamics of non-interest) to some extent. Therefore, the value of φ does not necessarily approximate 0 in empty environment, but will be at some level greater than 0 depending on the device noises and environmental conditions. Fortunately, one can devise a mechanism to automatically and adaptively estimate the noise level and determine an appropriate threshold for micro motion detection.

FIG. 1 illustrates an example of sleep data, which shows that the disclosed micromotion boosts the motion values compared to the regular motion statistics, underpinning a foundation for reliable and continuous BMS detection.

One disclosed approach to track sleep period is to identify the body movements during sleep. The body movements during sleep can exhibit distinct patterns that can be differentiated from activity motions in the daytime. Therefore, the system can recognize the sleep period by detecting the time period with the BMS patterns. The key challenge, however, is how to detect BMS accurately, robustly, and efficiently.

Figure 2:
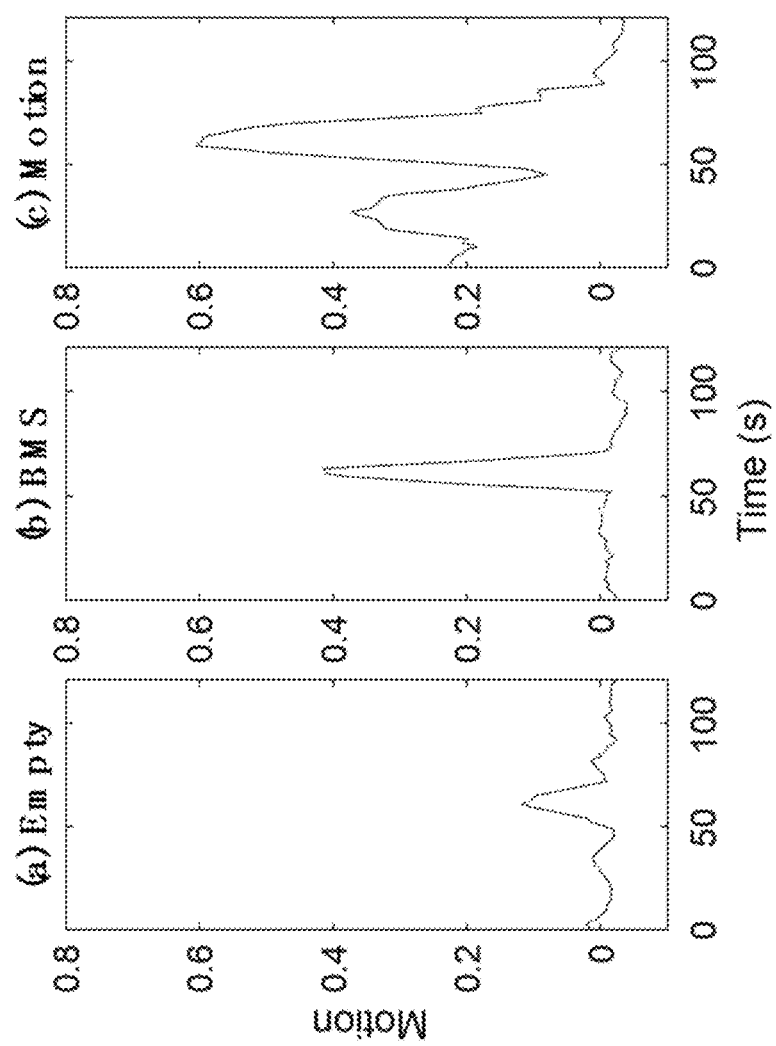
FIG. 2 illustrates an example of detecting body movements during sleep (BMS), according to some embodiments of the present disclosure.

FIG. 2 illustrates an example of body movements during sleep. As seen, compared with daily motions, BMS appear to be (1) transient: motions occur due to BMS but usually only last for a very short time, and the environment is otherwise quiet with no motion; (2) significant: motions due to BMS mostly cause quite high motion statistics, outstanding in the mostly quiet sleep time and comparable to large motions in the daytime; and (3) sparse: the moments with body movements during sleep are sparse throughout the entire sleep period. Consequently, motions due to BMS exhibit spiky and sparse patterns, which turn out to be unique characteristics for BMS detection.

One can formulate BMS detection as a spiky peak detection problem. Accounting for the above properties of BMS, one can devise the following constraints for the BMS motion peak detection. First, a minimum peak height means the maximum motion is required to be larger than a minimum peak height. Second, a maximum peak width means the formed motion peak due to one time of BMS should be narrow and spiky. In other words, the peak should appear and then vanish within a short time of w seconds, where w denotes the maximum peak width. Third, an isolation means there should be only one peak at a time as BMS are sparse and non-continuous. Fourth, the motion level beyond a potential peak should be low, ideally around noise level. This is to reflect the fact of motion absence except for body movements during sleep.

FIG. 2 illustrates possible peaks in the case of empty environment, sleep, and daily active motion, respectively. As seen, the BMS in sleep time exhibits a unique pattern compared with empty and motion cases.

To minimize computation, one can adopt an iterative approach for the disclosed BMS detection. Specifically, one can examine one condition at a time and will stop once a criterion is not met. The disclosed peak detection algorithm may not be perfect but is sufficient for BMS detection. First, not all possible BMS will be detected. For example, extremely small BMS (e.g., mouth movements) may be missing. Second, some motions caused by daytime activities may be detected as well. However, the goal is not to detect every single body movements of sleep but to detect the sleep period. The disclosed BMS detection underpins this goal even with some missing and false detections.

In some embodiments, the system can also perform presence detection and activity detection, both based on the (micro) motion statistics. The purpose is to eliminate the periods without human presence or with activities for sleep consideration. Apparently, sleep can only happen when a human subject stays quiet without voluntary activities.

Presence detection is to detect whether or not a user presents in the space. This can be done by examining the captured motion levels since a human subject cannot stay completely still for a long time. Whenever there are some voluntary motions, they will be reflected by the motion statistics. Evan when a user is sleeping, the potential unconscious BMS can trigger micro motion as well. This is different from the case when the environment is empty without any moving targets, in which case both the motion and micro motion estimation will be around zero.

One can employ a simple yet effective rule for presence detection. First, the system can perform motion detection by fusing motion and micro motion. Specifically, one can have $I_M(t)=\mathbb{1}[\phi(t)>\eta|\varphi(t)>\zeta]$ for any time t, where $\eta$ and $\zeta$ are the thresholds for motion and micro motion detection, respectively. Then presence indicator is a simple expansion of motion detection. One can apply a sliding window $W_P$ over time, and presence is claimed for the entire window if any motion is detected within it. This is based on the empirical observation that human cannot appear/disappear suddenly and $W_P$ is accordingly determined as a few minutes, e.g., 10 minutes.

Activity is defined when a user is being active, resulting in relatively intensive motion. Therefore, activity detection is based on the ratio of detection motion within a certain time window $W_A$. Specifically, activities are marked for a window as long as the motion ratio $\Sigma_{t \in W_A} I_M(t)/|W_A|$ is greater than a threshold ratio. $|W_A|$ denotes the window length, which can be normally chose as a few minutes (e.g., 5 minutes).

Figure 4:
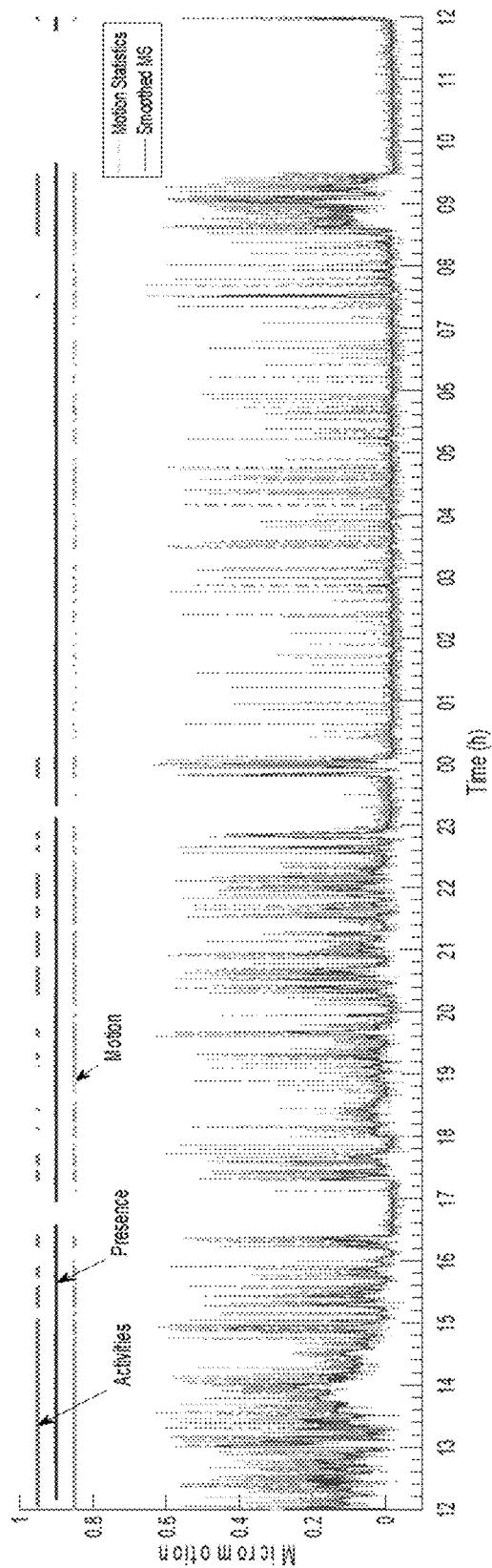
FIG. 4 illustrates an example of estimated presence and activities throughout a whole day of 24 hours based on motion detection, according to some embodiments of the present disclosure.

FIG. 4 is an example of the estimated presence and activities throughout a whole day of 24 hours.

In some embodiments, one can define a minimum unit of sleep as $W_U$ to indicate the shortest nap people would normally take. The value of $W_U$ can be determined empirically and quite arbitrarily as, for example, 15 minutes assuming a meaningful sleep lasts for at least such long. Then the system can break down the time into many of such units and examine the sleep likelihood of each of these units. The more BMS-like motions and the less high and consecutive motions, the more likely a sleep occurs. Correspondingly, the sleep likelihood estimation is also based on the motion statistics and the BMS detections.

Figure 3:
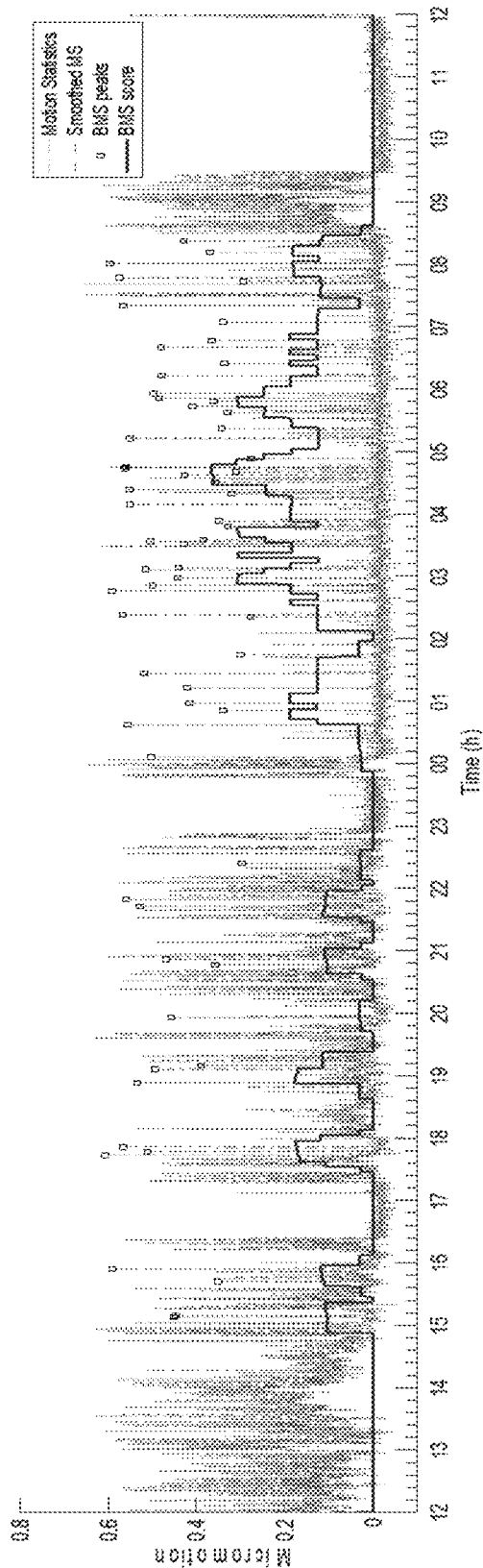
FIG. 3 illustrates an example of calculated BMS score, according to some embodiments of the present disclosure.

Considering a unit time $W_U\langle T \rangle$ ending at time T, the system can first calculate a BMS score for the unit as $B_U(t)=N_{BMS}(W_U\langle T \rangle)/|W_U|$, where $|W_U|$ is the length in seconds of the window $W_U\langle T \rangle$ and $N_{BMS}(W_U\langle t \rangle)$ denotes the amount of detected BMS within the $N_U$ seconds of window $W_U\langle T \rangle$. FIG. 3 shows an example of the calculated BMS score. As seen, although there can be non-zero BMS scores in the day time, the BMS scores corresponding to the actual sleep period are outstandingly higher than other periods, thanks to the denser BMS.

Then the system can calculate a sleep likelihood $L(t)=(1-M_I(t))\times B(t)$, where $M_I(t)$ is the motion intensity at time t, which is the averaged value of the motion statistic $\phi(t)$ over a certain window. The entire time window $W_U\langle t \rangle$ features the same BMS score $B_U(t)$ for every time point t. Importantly, the BMS score is set to zero for any time with activity or without presence, since, again, sleep and thus BMS are unlikely to happen if a user is voluntarily active or absent.

Figure 5:
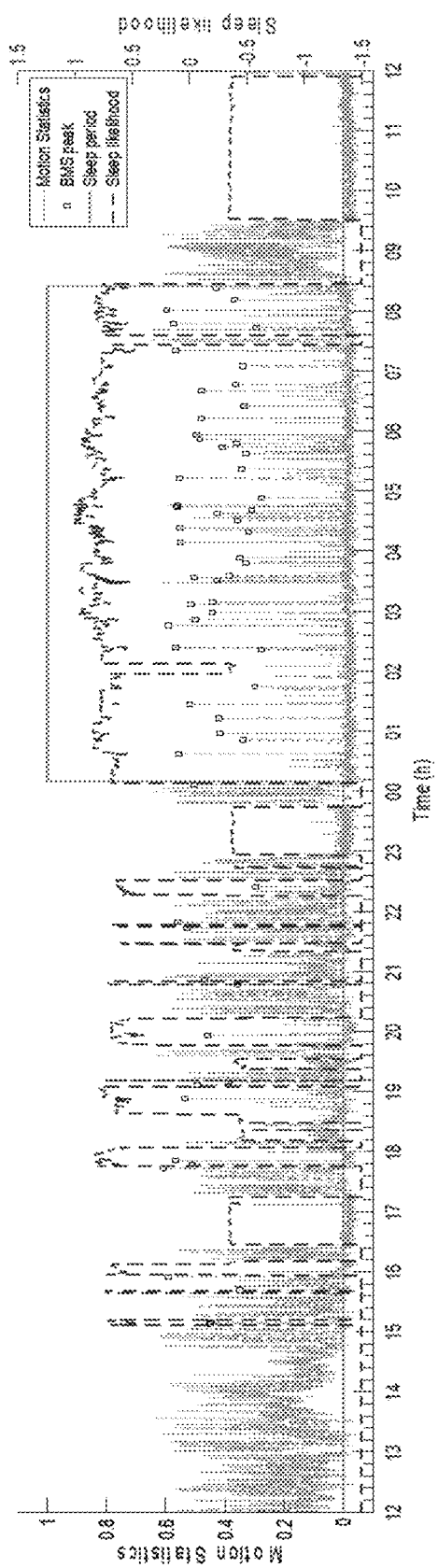
FIG. 5 illustrates an example of estimated sleep likelihood and sleep tracking result, according to some embodiments of the present disclosure.

FIG. 5 illustrates an example of the estimated sleep likelihood. One can further incorporate two factors for a better estimation. First, one can quantize the sleep likelihood as binary values by using the minimum likelihood value as an adaptive threshold: $L^b(t)=\mathbb{1}[L(t)>l]$, where $\mathbb{1}[\cdot]$ is an indicator function. $l=\min(L(t), \forall t\in W_O\langle T \rangle)$ denotes the sleep likelihood threshold for quantization, where $W_O(T)$ is a larger observation window that ends at time T and potentially covers the entire actual sleep period. Second, one can define a motion penalty based on the motion detection results. The motion penalty differs from the motion intensity as the former only applies to the time moments when motion is detected (i.e., $\phi(t)>\eta$), while the latter is the averaged motion statistic $\phi(t)$ that is always there for every single time point t. With the above two additional factors, the final sleep likelihood for each time point t then becomes $L'(t)=L(t)+L^b(t)-pI_M(t)$, where p is the constant motion penalty in presence of motion and $I_M(t)=\mathbb{1}[\phi(t)>\eta]$ is an indicator function of motion presence. FIG. 5 illustrates an example of the final sleep likelihood estimation. For brevity, $L(t)$ is still used for $L'(t)$ hereafter.

Given an observation window $W_O\langle T \rangle$, one can have a time series of sleep likelihood values $\{L(t), t\in W_O\langle T \rangle\}$. The window $W_O\langle T \rangle$ is a larger one, e.g., one day of motion data, such that it can cover the potential sleep period, if any. The remaining task is to recognize the entire sleep period based on the estimated sleep likelihood. The system can achieve so by finding the period P* within $W_O\langle T \rangle$ that maximizes the integral sleep likelihood. One can first identify k initial periods, each of one-hour segments that feature the largest integral sleep likelihood values. Then the sleep recognition algorithm starts from each of the identified segment and iteratively expands to former and later time, with a step size s. The reason that the system initially chooses top-k segments for searching is because that the largest one, in rare cases, may be a false high value and fall out of the actual sleep period. The total sleep likelihood of a period $P_i$ is calculated as the sum of the sleep likelihood over time, i.e., $Q(P_i)=\Sigma_{t\in P_i} L(t)$.

The sleep durations of the majority of people fall in a common range, e.g., around 7 to 8 hours per day. Therefore, to avoid unrealistic long or short sleep periods, the system can adjust the original total sleep likelihood Q by considering the typical distribution of normal sleep. Specifically, the system can build a Gaussian distribution based on the normal sleep time reported in medical literature. Then if the period $P_i$ being considered is out of the 3–$\sigma$ zone of the normal distribution, an attenuation factor of the corresponding probability will be applied to the calculated total score $Q(P_i)$.

Finally, the most likely period P* is found as the one that maximizes the total score Q(P*). P* will be claimed as a detected sleep period if the total score Q(P*) is greater than a certain threshold. In some embodiments of AnySleep, at most one sleep period will be detected for a given window $W_O \langle T \rangle$. In case a user wakes up during a sleep and then sleeps again, the two periods of sleep will be automatically combined as one sleep and the wake-up time will be reflected in the corresponding sleep summary, as detailed next. An example of sleep recognition is shown in FIG. 5.

For the recognized sleep periods, several sleep-related properties are assessed and reported. These include start time (i.e., time to bed/sleep), end time (i.e., wake up time), sleep duration, awake time during sleep, wake-up times during a sleep, etc. Most properties are straight-forward to calculate based on the detected sleep period. Awake time is estimated as the durations which observe activities during sleep, while wake-up times are number of non-consecutive activity periods detected. One can also calculate a sleep score to indicate the sleep quality. Computing a sleep score is a complicated task, which is even more challenging when one only has motion information. Despite rich research on BMS, there lacks an established formula to calculate sleep score from the BMS. In AnySleep, based on the intuition that the longer one sleeps and the more quiet (i.e., less motion) one experiences, the higher sleep score one could have, the present teaching discloses an empirical formula as below:

$$S_{sleep} = \min\left(\left(\frac{100}{8}D - \alpha M_a\right) * (1 - M_W), 100\right)$$

where D is the sleep time in hours, $M_a = \Sigma_{t \in W_O} \mathbb{1}[\phi(t) > \eta_{low}]$ denotes the motion-indicated wakeness, and $M_w = \Sigma_{t \in W_O} \mathbb{1}[\phi(t) > \eta_{high}]/(D \times 3600)$ indicates the motion activeness. As the motion statistic is mostly independent of the environment, one can empirically set the low motion threshold $\eta_{low}=0.35$ and the high one as $\eta_{high}=0.5$. $\alpha$ is a constant weighting factor that is empirically determined such that the calculated sleep scores are mostly in a reasonable range especially for normal sleep of healthy subjects.

The above shows how to detect a possible sleep period, given a particular time window with motion observations. In practice, the motion data will enter in real-time, and thus the algorithm needs to run every once a while (e.g., every 10 minutes, depending on user preferences) to update the sleep tracking results. To do so, the system can slide the observation window $W_O$ over time and takes the latest data ending at the current time point as input. Given any window $W_O$, the disclosed sleep tracking algorithm will either detect and output a potential sleep period or announce no sleep therein. As the sliding step is much smaller than the window size, the sliding windows will overlap and lead to potential conflicting detection results. In other words, multiple time windows covering the same sleep period, entirely or partially, may output different sleep information.

To handle sleep tracking in real-time system and address the above issues, consider a window $W_O \langle T \rangle$ ending at time T, and assume a sleep period $P_{W_O}$ is detected. As mentioned earlier, $P_{W_O}$ should contain the detected time to bed (i.e., starting time), time to wake up (i.e., end time), other sleep summary information, and particularly, a sleep likelihood score of the detected sleep period. The disclosed AnySleep system can maintain a list of the detected sleep periods, denoted as $\mathbb{P}=\{P_{W_O}(T_1), \ldots, P_{W_O}(T_N)\}$ where $P_{W_O}(T_i)$ is the detected sleep period given observation window $W_O \langle T_i \rangle$. In some embodiments, AnySleep then performs online updating to confirm one and only one most likely sleep period for a given time period.

Specifically, every time when a new sleep period $P_{W_O}(T_c)$ is detected, e.g., one for the latest time window ending at current time $T_c$, the sleep period will be compared with all previously detected periods that overlap with $P_{W_O}(T_c)$. $P_{W_O}(T_c)$ will be added into the history list $\mathbb{P}$ only if its sleep likelihood score is the maximum among those of all its overlapped sleep periods. In such cases, all the overlapped sleep periods of $P_{W_O}(T_c)$ will become outdated and thus removed from $\mathbb{P}$. Otherwise, $P_{W_O}(T_c)$ will simply be discarded and $\mathbb{P}$ remains unchanged. By doing so, the periods maintained in $\mathbb{P}$ become the most likely detections to date and will be reflected to users upon real-time user queries.

Finally, a sleep segment in $\mathbb{P}$ will be finally confirmed and no longer updated if the corresponding end time becomes earlier than the starting time of the current observations window, $W_O \langle T_c \rangle$, as no further sleep periods will be possible to be detected for the concerned time period.

In some embodiments, while AnySleep system involves quite some parameters and thresholds, the system can determine some key parameters automatically and adaptively.

First, for empty level of micromotion, one can safely assume that, over a sufficiently long time of observation (e.g., a full day), there will be at least some time the user is absent or still/quasi-still. Such periods can be treated as the empty case, and the corresponding motion measurements can be utilized to estimate the reference empty level for micromotion. To do so, the system will find a certain period throughout the day that experiences the lowest motion and none of the motion statistics exceed the threshold (i.e., no motion occurs). The system may then estimate the average motion within this period as the empty micromotion level, which will be then subtracted from the original micromotion estimates.

Second, for motion/micromotion threshold, the system can determine an adaptive motion/micromotion threshold with reference to the motion level when there is no user present. Therefore, the system can still find the most likely "empty" period throughout the day. Instead of using the average motion level, the system now detects the maximum motion statistics/micromotion of the empty window as the adaptive threshold for motion/micromotion.

Third, for leveraging history, although the motion/micromotion levels in empty environments may vary a little in different environments and on different devices, the values should be consistent once a specific system has been deployed at a certain site. Therefore, in practical deployment, the estimated empty levels, thresholds, and other parameters should not change too vastly over time. Inspired by this observation, one can update the parameters in a more conservative way by considering historical estimates. Specifically, for any parameter $\gamma$, the system can update its latest value as below: $\tilde{\gamma}_i = \beta_\gamma \gamma_{i-1} + (1-\beta_\gamma)\gamma_i$, where $\gamma_i$ is the estimate based on the current observations, $\gamma_{i-1}$ denotes the previously determined value, and $\beta_\gamma$ is a low-pass averaging factor. By doing so, the system can also avoid outlying values produced by the automatic parameter selection (e.g., wrong motion threshold can be estimated if the users are highly active throughout a certain day).

Figure 6:
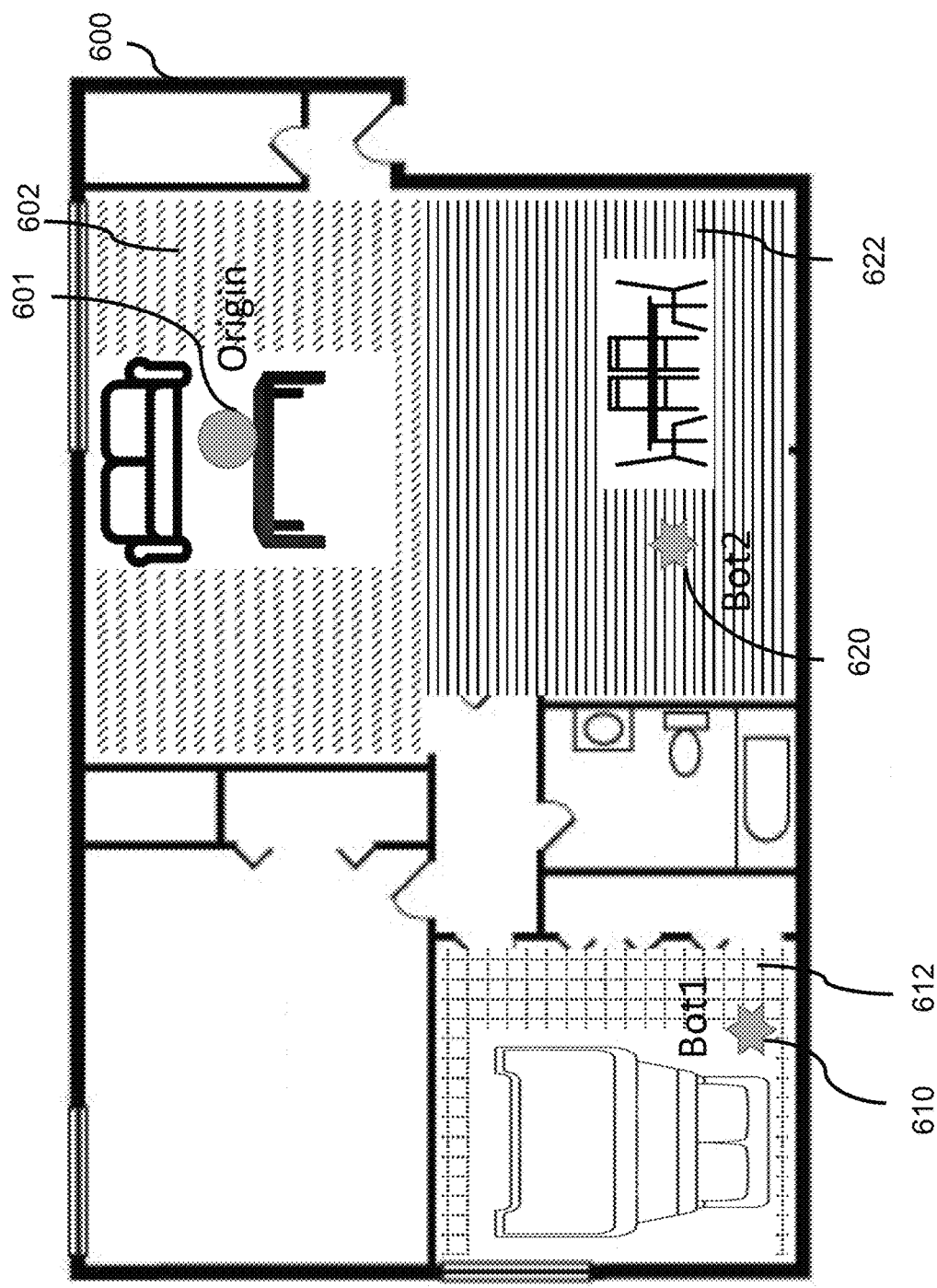
FIG. 6 illustrates an exemplary scenario where object motion or sleep motion is detected in a venue, according to some embodiments of the present disclosure.

FIG. 6 illustrates an exemplary scenario where object motion or sleep motion is detected in a venue, according to one embodiment of the present teaching. FIG. 6 shows a setup that can be used for WiDetect, AnySleep, or any motion detection system described herein. For example, as shown in FIG. 6, in a 2-bedroom apartment 600, Origin 601 may be placed in the living-room area 602, Bot 1 610 may be placed in a bedroom1-area 612, and Bot 2 620 may be placed in the dining-room area 622. Each of Bot 1 610 and Bot 2 620 can transmit a wireless signal to the Origin 601, which can obtain channel information of a wireless multipath channel based on the wireless signal. The Origin 601, by itself or through a third device like a motion detector, can compute motion information based on the channel information and detect object/user motion/activity based on the motion information. That is, the Origin 601, by itself or through a third device like a motion detector, can detect object/user motion/activity based on wireless signals transmitted by Bot 1 610 and/or Bot 2 620.

In some embodiments, if object motion is detected based on wireless signals transmitted by both Bot 1 610 and Bot 2 620, the activity/motion or the object (e.g. person/user) may be in the living-room area 602. If object motion, e.g. sleep motion, is detected based only on wireless signals transmitted by Bot 1 610, the activity/motion or the object (e.g. person/user) may be in the bedroom-1 area 612. If object motion/activity is detected based only on wireless signals transmitted by Bot 2 620, the activity/motion or the object (e.g. person/user) may be in the dining-room area 622. If object motion/activity cannot be detected based on wireless signals transmitted by either Bot 1 610 or Bot 2 620, then it may be determined that nobody and no object is in the apartment 600.

Figure 7:
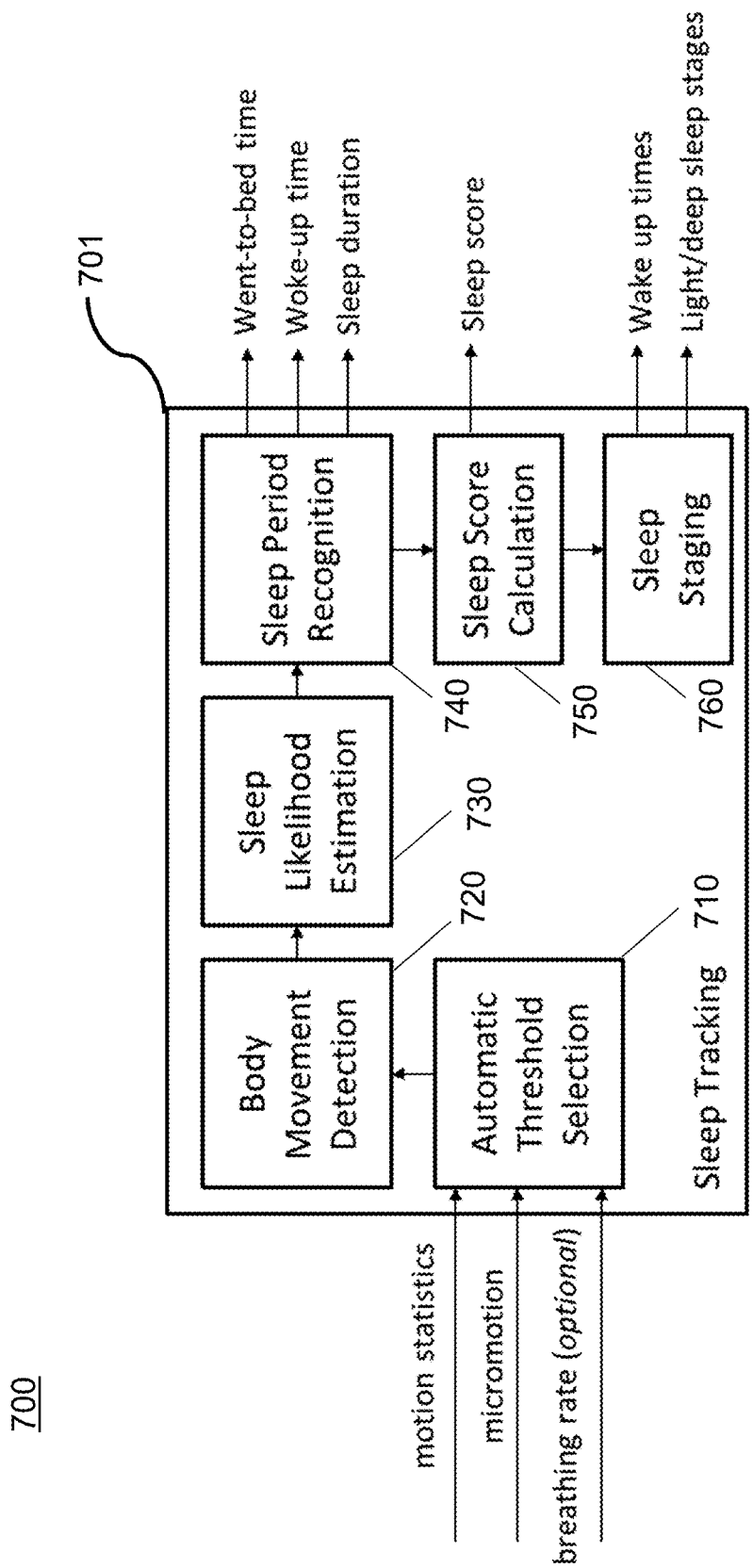
FIG. 7 illustrates an exemplary method for radio-based sleep tracking, according to some embodiments of the present disclosure.

FIG. 7 illustrates an exemplary method 700 for radio-based sleep tracking, according to some embodiments of the present disclosure. As shown in FIG. 7, the method 700 is performed by a sleep tracking module 701, which includes: an automatic threshold selection module 710, a body movement detection module 720, a sleep likelihood estimation module 730, a sleep period recognition module 740, a sleep score calculation module 750, and a sleep staging module 760.

The automatic threshold selection module 710 can take inputs of motion statistics, micromotion data, and optionally breathing rate, based on a wireless motion detection, e.g. as shown in FIG. 6. In some embodiments, the sleep tracking module 701 can take inputs with arbitrary time lengths, but would produce the best results if the inputs cover the entire sleep period. In some embodiments, the disclosed method does not require any input (e.g., regular bedtime, # of people) from a user. After the body movement detection module 720 and the sleep likelihood estimation module 730, a sleep period can be recognized at the sleep period recognition module 740. In some embodiments, the sleep period recognition module 740 can generate outputs including: a went-to-bed time, a woke-up time, and a sleep duration of the monitored and tracked sleep motion. The sleep score calculation module 750 can calculate and generate a sleep score as an output, e.g. to indicate a quality of the sleep. In some embodiments, the sleep staging module 760 may determine sleep staging by generating outputs including: wake up times and light/deep sleep stages.

In some embodiments, a two-person sleeping can be treated indifferently, and the method 700 may just output one shared time-to-bed and wake-up time. In some embodiments, the method 700 can support both 5 GHz and 2.4 GHz wireless signals for motion detection, while 5 GHz wireless signal has a better performance.

Figure 8:
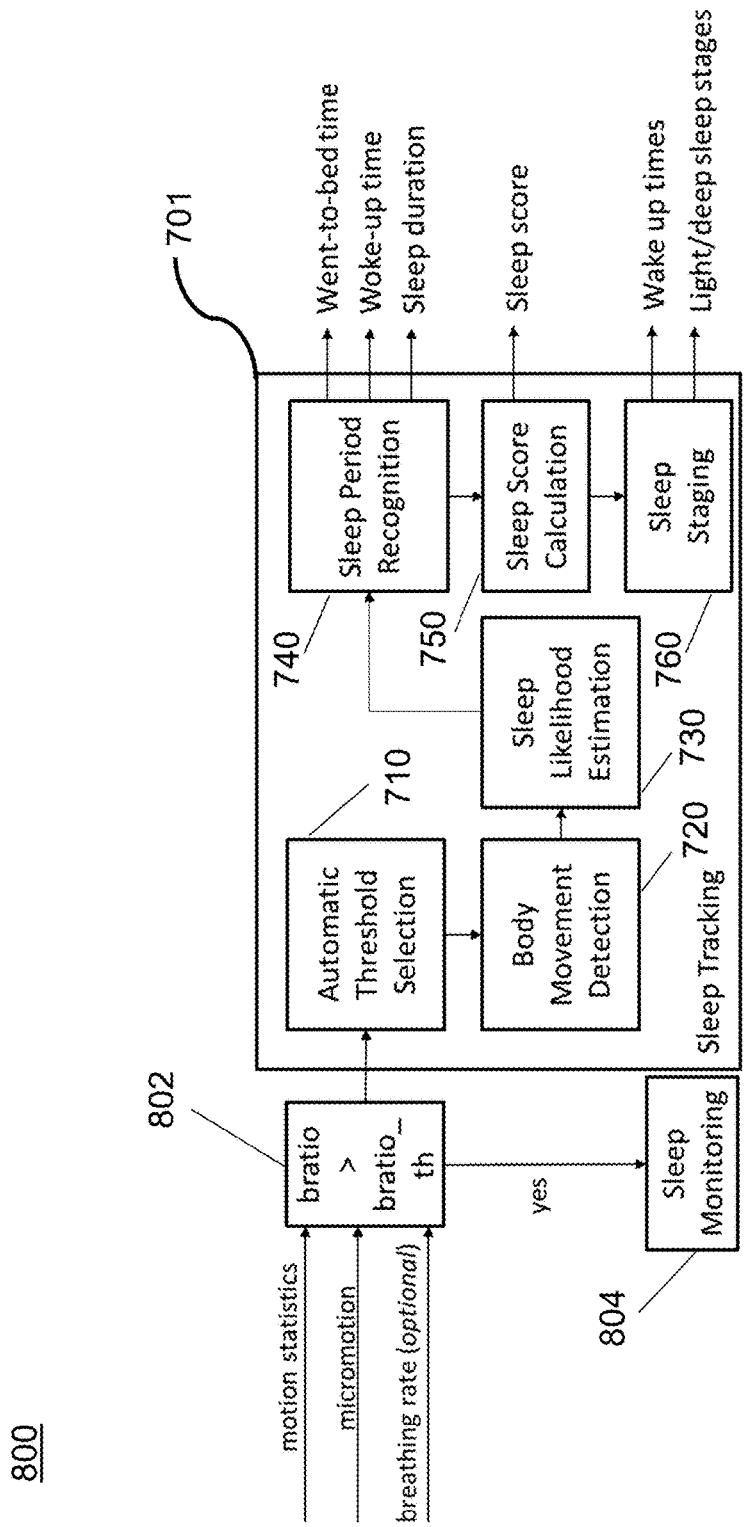
FIG. 8 illustrates an exemplary unified method for sleep monitoring and tracking, according to some embodiments of the present disclosure.

FIG. 8 illustrates an exemplary unified method 800 for sleep monitoring and tracking, according to some embodiments of the present disclosure. Compared to the method 700 in FIG. 7, the method 800 includes a determination step 802, where a breathing rate estimation (bratio) in a certain time period is calculated based on inputs of motion statistics, mocromotion data, and optionally breathing rate, and then compared to a threshold bratio_th. If bratio>bratio_th, which means there is a good amount of breathing rate, the method 800 goes to a sleep monitoring process 804. If not, the method 800 goes to the sleep tracking process which may be performed as described above with respect to the method 700 in FIG. 7.

Figure 9:
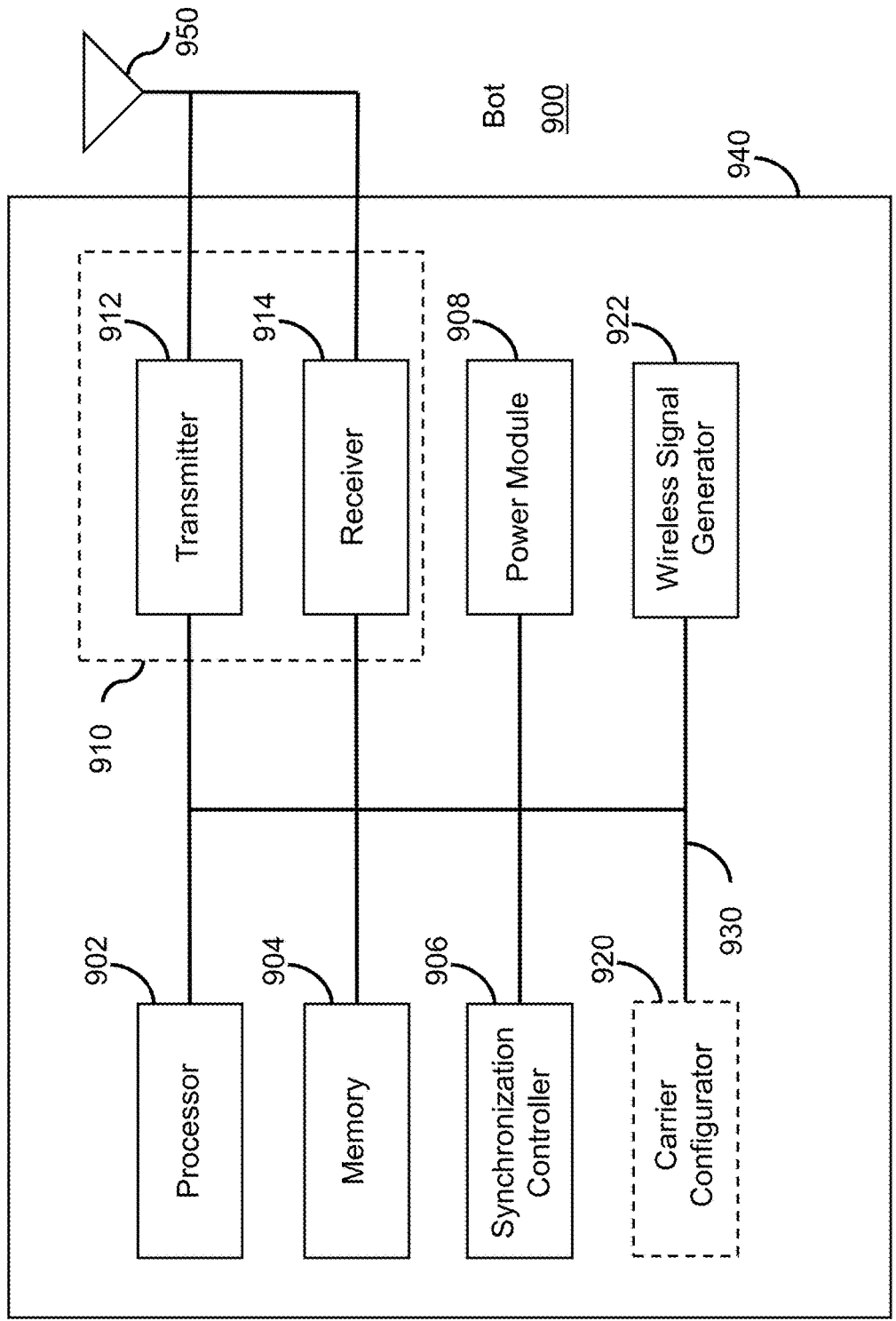
FIG. 9 illustrates an exemplary block diagram of a first wireless device of a system for radio-based sleep tracking, according to some embodiments of the present disclosure.

FIG. 9 illustrates an exemplary block diagram of a first wireless device, e.g. a Bot 900, of a system for radio-based sleep tracking, according to some embodiments of the present disclosure. The Bot 900 is an example of a device that can be configured to implement the various methods described herein. As shown in FIG. 9, the Bot 900 includes a housing 940 containing a processor 902, a memory 904, a transceiver 910 comprising a transmitter 912 and receiver 914, a synchronization controller 906, a power module 908, an optional carrier configurator 920 and a wireless signal generator 922.

In this embodiment, the processor 902 controls the general operation of the Bot 900 and can include one or more processing circuits or modules such as a central processing unit (CPU) and/or any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable circuits, devices and/or structures that can perform calculations or other manipulations of data.

The memory 904, which can include both read-only memory (ROM) and random access memory (RAM), can provide instructions and data to the processor 902. A portion of the memory 904 can also include non-volatile random access memory (NVRAM). The processor 902 typically performs logical and arithmetic operations based on program instructions stored within the memory 904. The instructions (a.k.a., software) stored in the memory 904 can be executed by the processor 902 to perform the methods described herein. The processor 902 and the memory 904 together form a processing system that stores and executes software. As used herein, "software" means any type of instructions, whether referred to as software, firmware, middleware, microcode, etc. which can configure a machine or device to perform one or more desired functions or processes. Instructions can include code (e.g., in source code format, binary code format, executable code format, or any other suitable format of code). The instructions, when executed by the one or more processors, cause the processing system to perform the various functions described herein.

The transceiver 910, which includes the transmitter 912 and receiver 914, allows the Bot 900 to transmit and receive data to and from a remote device (e.g., an Origin or another Bot). An antenna 950 is typically attached to the housing 940 and electrically coupled to the transceiver 910. In various embodiments, the Bot 900 includes (not shown) multiple transmitters, multiple receivers, and multiple transceivers. In one embodiment, the antenna 950 is replaced with a multi-antenna array 950 that can form a plurality of beams each of which points in a distinct direction. The transmitter 912 can be configured to wirelessly transmit signals having different types or functions, such signals being generated by the processor 902. Similarly, the receiver 914 is configured to receive wireless signals having different types or functions, and the processor 902 is configured to process signals of a plurality of different types.

The Bot 900 in this example may serve as a Bot or TX in FIGS. 1-8 for wireless sleep tracking. For example, the wireless signal generator 922 may generate and transmit, via the transmitter 912, a wireless signal through a wireless channel in the venue. The wireless signal carries information of the channel. Because the wireless signal is impacted by a sleep motion of a user in the venue, the channel information includes information about the motion and location of the motion. As such, motion detection and tracking can be performed following the methods disclosed above. The generation of the wireless signal at the wireless signal generator 922 may be based on a request for sound sensing from another device, e.g. an Origin, or based on a system pre-configuration. That is, the Bot 900 may or may not know that the wireless signal transmitted will be used for wireless sound sensing.

The synchronization controller 906 in this example may be configured to control the operations of the Bot 900 to be synchronized or un-synchronized with another device, e.g. an Origin or another Bot. In one embodiment, the synchronization controller 906 may control the Bot 900 to be synchronized with an Origin that receives the wireless signal transmitted by the Bot 900. In another embodiment, the synchronization controller 906 may control the Bot 900 to transmit the wireless signal asynchronously with other Bots. In another embodiment, each of the Bot 900 and other Bots may transmit the wireless signals individually and asynchronously.

The carrier configurator 920 is an optional component in Bot 900 to configure transmission resources, e.g. time and carrier, for transmitting the wireless signal generated by the wireless signal generator 922. In one embodiment, each CI of the time series of CI has one or more components each corresponding to a carrier or sub-carrier of the transmission of the wireless signal. The wireless sound sensing may be based on any one or any combination of the components.

The power module 908 can include a power source such as one or more batteries, and a power regulator, to provide regulated power to each of the above-described modules in FIG. 9. In some embodiments, if the Bot 900 is coupled to a dedicated external power source (e.g., a wall electrical outlet), the power module 908 can include a transformer and a power regulator.

The various modules discussed above are coupled together by a bus system 930. The bus system 930 can include a data bus and, for example, a power bus, a control signal bus, and/or a status signal bus in addition to the data bus. It is understood that the modules of the Bot 900 can be operatively coupled to one another using any suitable techniques and mediums.

Although a number of separate modules or components are illustrated in FIG. 9, persons of ordinary skill in the art will understand that one or more of the modules can be combined or commonly implemented. For example, the processor 902 can implement not only the functionality described above with respect to the processor 902, but also implement the functionality described above with respect to the wireless signal generator 922. Conversely, each of the modules illustrated in FIG. 9 can be implemented using a plurality of separate components or elements.

Figure 10:
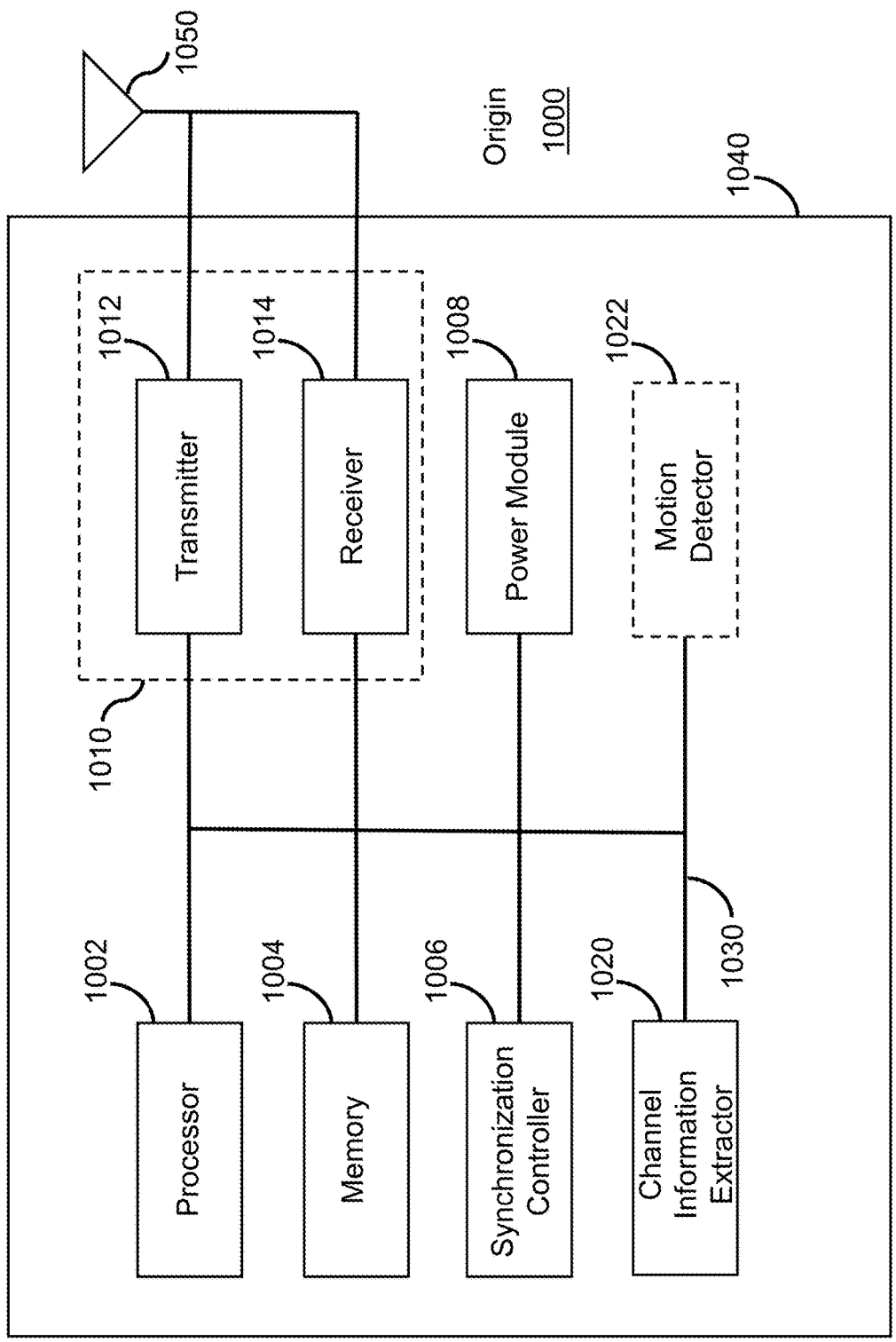
FIG. 10 illustrates an exemplary block diagram of a second wireless device of a system for radio-based sleep tracking, according to some embodiments of the present disclosure.

FIG. 10 illustrates an exemplary block diagram of a second wireless device, e.g. an Origin 1000, of a system for radio-based sleep tracking, according to some embodiments of the present disclosure. The Origin 1000 is an example of a device that can be configured to implement the various methods described herein. The Origin 1000 in this example may serve as an Origin or RX in FIGS. 1-8 for wireless sensing in a venue. As shown in FIG. 10, the Origin 1000 includes a housing 1040 containing a processor 1002, a memory 1004, a transceiver 1010 comprising a transmitter 1012 and a receiver 1014, a power module 1008, a synchronization controller 1006, a channel information extractor 1020, and an optional motion detector 1022.

In this embodiment, the processor 1002, the memory 1004, the transceiver 1010 and the power module 1008 work similarly to the processor 902, the memory 904, the transceiver 910 and the power module 908 in the Bot 900. An antenna 1050 or a multi-antenna array 1050 is typically attached to the housing 1040 and electrically coupled to the transceiver 1010.

The Origin 1000 may be a second wireless device that has a different type from that of the first wireless device (e.g. the Bot 900). In particular, the channel information extractor 1020 in the Origin 1000 is configured for receiving the wireless signal through the wireless channel, and obtaining a time series of channel information (CI) of the wireless channel based on the wireless signal. The channel information extractor 1020 may send the extracted CI to the optional motion detector 1022 or to a motion detector outside the Origin 1000 for wireless sound sensing in the venue.

The motion detector 1022 is an optional component in the Origin 1000. In one embodiment, it is within the Origin 1000 as shown in FIG. 10. In another embodiment, it is outside the Origin 1000 and in another device, which may be a Bot, another Origin, a cloud server, a fog server, a local server, and an edge server. The optional motion detector 1022 may be configured for detecting sound information from a vibrating object or source in the venue based on motion information. The motion information may be computed based on the time series of CI by the motion detector 1022 or another motion detector outside the Origin 1000.

The synchronization controller 1006 in this example may be configured to control the operations of the Origin 1000 to be synchronized or un-synchronized with another device, e.g. a Bot, another Origin, or an independent motion detector. In one embodiment, the synchronization controller 1006 may control the Origin 1000 to be synchronized with a Bot that transmits a wireless signal. In another embodiment, the synchronization controller 1006 may control the Origin 1000 to receive the wireless signal asynchronously with other Origins. In another embodiment, each of the Origin 1000 and other Origins may receive the wireless signals individually and asynchronously. In one embodiment, the optional motion detector 1022 or a motion detector outside the Origin 1000 is configured for asynchronously computing respective heterogeneous motion information based on the respective time series of CI.

The various modules discussed above are coupled together by a bus system 1030. The bus system 1030 can include a data bus and, for example, a power bus, a control signal bus, and/or a status signal bus in addition to the data bus. It is understood that the modules of the Origin 1000 can be operatively coupled to one another using any suitable techniques and mediums.

Although a number of separate modules or components are illustrated in FIG. 10, persons of ordinary skill in the art will understand that one or more of the modules can be combined or commonly implemented. For example, the processor 1002 can implement not only the functionality described above with respect to the processor 1002, but also implement the functionality described above with respect to the channel information extractor 1020. Conversely, each of the modules illustrated in FIG. 10 can be implemented using a plurality of separate components or elements.

Figure 11:
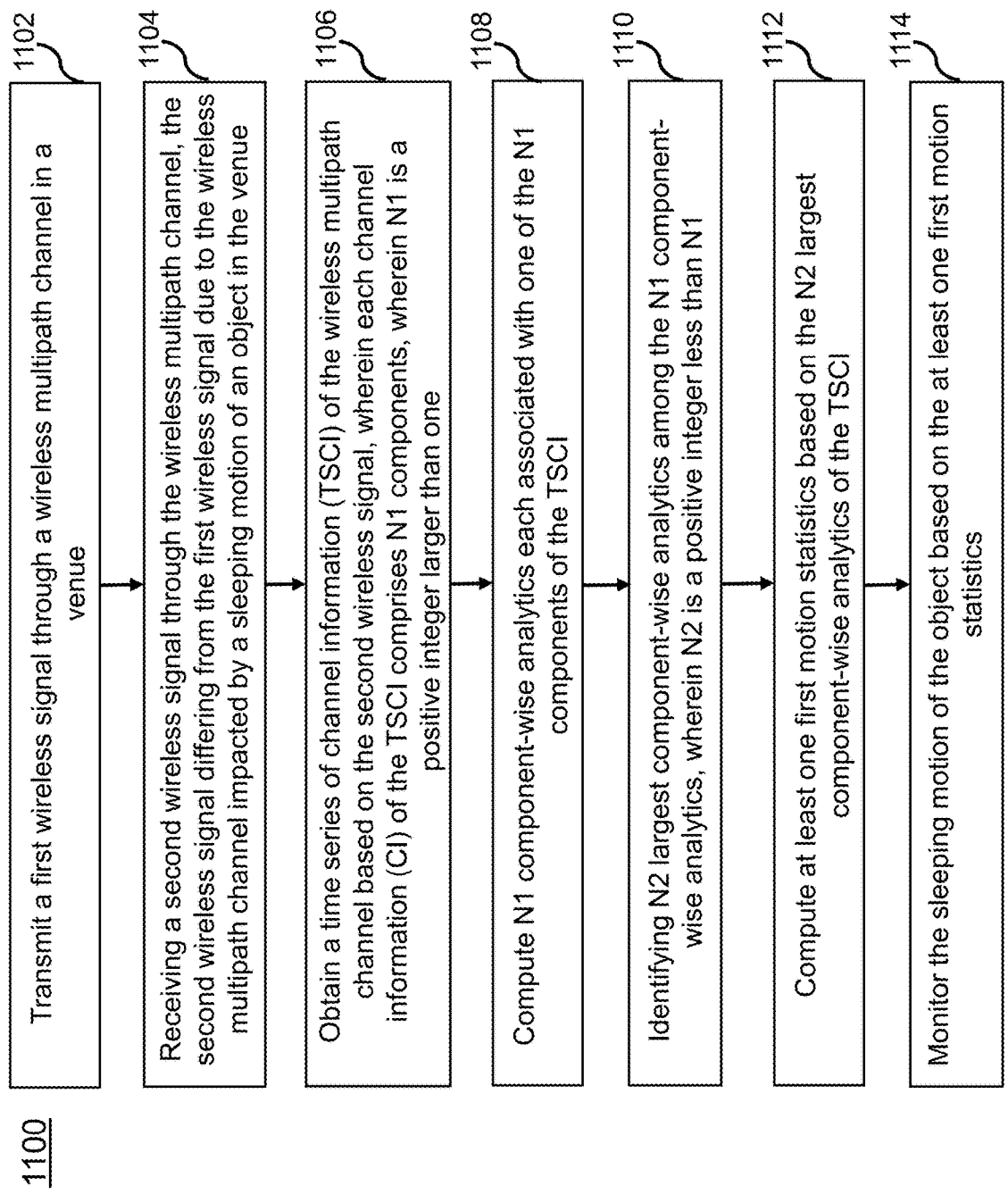
FIG. 11 illustrates a flow chart of an exemplary method for radio-based sleep tracking, according to some embodiments of the present disclosure.

FIG. 11 illustrates a flow chart of an exemplary method 1100 for radio-based sleep tracking, according to some embodiments of the present disclosure. In various embodiments, the method 1100 can be performed by the systems disclosed above and herein. At operation 1102, a first wireless signal is transmitted through a wireless multipath channel in a venue. At operation 1104, a second wireless signal is received through the wireless multipath channel, the second wireless signal differing from the first wireless signal due to the wireless multipath channel impacted by a sleeping motion of an object in the venue. At operation 1106, a time series of channel information (TSCI) of the wireless multipath channel is obtained based on the second wireless signal, wherein each channel information (CI) of the TSCI comprises N1 components, wherein N1 is a positive integer larger than one. At operation 1108, N1 component-wise analytics each associated with one of the N1 components of the TSCI are computed. At operation 1110, N2 largest component-wise analytics are identified among the N1 component-wise analytics, wherein N2 is a positive integer less than N1. At operation 1112, at least one first motion statistics is computed based on the N2 largest component-wise analytics of the TSCI. At operation 1114, the sleeping motion of the object is monitored based on the at least one first motion statistics. The order of the operations in FIG. 11 may be changed according to various embodiments of the present teaching.

In some embodiments, the present teaching discloses systems and methods for sleep tracking using two motion statistics but without using breathing statistics. An exemplary method includes the following steps. First, the system can compute motion statistics (MS), for each pair of TX-RX. Then, the system can compute micro motion statistics (MM), for each TX-RX link. The system may perform automatic (e.g. dynamic, adaptive, or periodic) selection of thresholds for MS and MM. For any time instance, the system can compute MM-residue by subtracting L1 from MM, where the L1 or "MM empty-mrc-motion-level" may be an estimate of DC level of MM when the object (e.g. person or user) is absent and the venue is "quiet" in terms of MM. This may be used in a preliminary screen of the presence of the object. It may be min{mean(MM[w]): all window w in a period}, where the window size may be 30, 60 or 90 minutes, and the "mean" here may be a weighted mean. In some embodiments, L1 may be updated periodically (e.g. once a day). It may be a weighted average of the current value and the past (or even future) few values (e.g. it may be low-pass filtered for continuity, perhaps to suppress noise).

In some embodiment, for any time instance, the system can detect motion if either MS>T1 or MM>T2. The T1 or "MS threshold" or "T_MS" may be an estimate of MS level when the object is absent. It may be max {MS[arg min(mean(MS[w]))]}. It may be to compute the mean of each sliding window (e.g. 5, 10, 15, 20, 25, or 30, etc. minutes) of MS in a period (e.g. 24 hours), identify the sliding window with the smallest mean which should be a "quiet" window with no person/user present, compute max of MS in the window. The T_MS may be adjusted by subtracting or adding a quantity. The T2 or "MM threshold" or "T_MM" may be an estimate of MM level when the object is absent. It may be max {MM[arg min(mean(MM[w]))]}.

For any sliding time window, the system can compute a presence of object in a sliding window if motion is detect in any time stance in the sliding window. For any sliding time window, the system can detect an activity in the sliding window if the amount of time instance in the sliding window with motion detected exceeds a threshold (e.g. 30% of all time instances in the sliding window). The system can identify peaks of MM such that (i) peak MM>T3, (ii) "right_base"–"left_base"<T4. (i.e. identify all peaks and then eliminate those that do not satisfy both (i) and (ii).) The goal is to find peaks corresponding to movements naturally occurring during sleep, or "body-motion-during-sleep" (i.e. body motion such as body rolling/turning or hand/head/body motion).

The T3 or "min_peak_height" is a threshold to qualify sleep motion. Basically a legitimate sleep motion cannot be too small. It may be min[mean(sorted_MM_res[1:k]), 0.5], wherein k may be 50. Within a period (e.g. 24 hours), the threshold may be a mean of the largest k (e.g. 50) MM. The "right_min" or "right_base" is the time of first minimum point on the right hand side for the neighboring MM below the T3. The "left_min" or "left_base" is the time of first minimum point on the left hand side for the neighboring MM below the T3. The T4 or "min_base_gap" is another threshold to qualify sleep motion. Basically a legitimate sleep motion cannot be too long in time duration (e.g. end within 2 seconds). The right_min-left_min is a measure of the "duration" of the motion associated with the MM peak.

Optionally, the system can eliminate peaks s.t. a peak-prominence measure (a measure of height of a peak relative to lowest contour) is larger than a threshold. Optionally, the system can eliminate or merge neighboring peaks that are close to each other (e.g. within 10 minutes). In some embodiments, the system can eliminate a peak if no presence of object (defined above) is detected in a (small) window around the peak. In some embodiments, the system can eliminate a peak if activity (defined above) is detected beyond the "left_base" and the "right_base" within a (larger) window around the peak, e.g. the window around the peak at time t, from (t−delta) to (t+delta). In some embodiments, the system can eliminate a peak if it is the only peak (e.g. singular peak) within a long time period (e.g. 90 minutes, 2 hours, 3 hours).

For each time instance of the remaining peak, the system can compute a body-movement-during-sleep indicator (BMS) as 1 if a remaining peak occurs at the time, and 0 if no remaining peak occur at the time. For each sliding window (e.g. 30 minute long), the system can count the remaining peaks in the sliding window and compute a BMS score ("BMS_score") as the percentage of time instances in the sliding window being the remaining peaks. It may be sum(BMS[w])/w. For each time instance, the system can compute a sleep likelihood score (SL) based on the BMS and a motion intensity measure. It may be (1−motion_intensity)* BMS_score. Likelihood should be higher if there are more BMS.

For each time instance, the system can compute a sleep indicator (SI) as 1 if SL>T5 and 0 otherwise, where T5 may be min(SL(SL>0)), i.e. a minimum among the non-zero SL). For each time instance, the system can compute a test score based on SL, and SI. It may be SL+SI−motion_penalty. Within a day, the system can find the 1-hour period with the highest sum of test score as an initial estimate of a sleep period.

The system may expand the sleep period to the left and to the right recursively (e.g. expand to right, then to left, then to right, and so on) with an increment step of Delta_T. When total duration of sleep period is approaching or beyond a normal range (e.g. 8/9 hours; the value may be adaptively adjusted based on a recognition of the user, e.g. 8/9/10 hours for a child, 7/8/9 hours for an adult, or 5/6 hours for an older person; the value may be adjusted based on the day of the week, e.g. longer for weekends or holidays and shorter for week days), the test score may be reduced s.t. it is e.g. Delta_T may be 5, 10, 15, or etc. (minutes). Recursion may stop when total sum of test score start to decrease (i.e. when test score is negative).

In some embodiments, the system can compute sleep analytics such as sleep start time (beginning time of sleep period), sleep end time (end time of sleep period), sleep duration (length of sleep period), interruption during sleep (number of times interruption occur during sleep period), interruption duration during sleep (or "awake_time_during_sleep", which is the amount of time during the sleep period that activity is detected), wakeup_times, and/or activity_times.

The following numbered clauses provide implementation examples for radio-based sleep tracking.

Clause 1. A method/device/system/software of a radio-based sleep tracking system, comprising: transmitting a wireless signal from a Type1 heterogeneous wireless device of the system through a wireless multipath channel in a venue, wherein the wireless multipath channel is impacted by a sleeping motion of an object in the venue; receiving the wireless signal by a Type2 heterogeneous wireless device of the system through the wireless multipath channel, wherein the received wireless signal differs from the transmitted wireless signal due to the wireless multipath channel and the sleeping motion of the object; obtaining a time series of channel information (TSCI) of the wireless multipath channel based on the received wireless signal using a process, a memory and a set of instructions, wherein each channel information (CI) of the TSCI comprises N1 components; computing N1 component-wise analytics each associated with one of the N1 components of the TSCI; identifying N2 largest component-wise analytics; computing a first motion statistics based on the N2 largest component-wise analytics of the TSCI; monitoring the sleeping motion of the object based on the first motion statistics.

In some embodiments, CI may be CSI, CFR, CIR. The N1 components may be subcarrier values of CFR, or tap values of CIR. The component-wise analytics may be term-by-term multiplication of corresponding component For example, let X(t1) and X(t2) be two CI at time t1 and t2, each CI being N1-tuples. The i^th component-wise analytics may be X1(i)*X2(i), where X1(i) and X2(i) are the i^{th} components of X(t1) and X(t2). It may be an estimate of component-wise auto-correlation function. The analytics may also be the magnitude, or a magnitude feature (e.g. a function of the magnitude), of the X1(i)*X2(i). It may be a weighted average of multiple pairs of (t1, t2), e.g. (1,2), (2,3), (3,4) with the same time difference (i.e. t2−t1). In some embodiments, the first motion analytics may be "micro motion" (MM). It may be an average or weighted average of a feature of N2 largest component-wise analytics. The feature may be absolute value, magnitude, magnitude square, etc. The object may be a person. The "sleep motion" may include motion when the person is sleep, and also motion when the person is not sleep, or even absent in the venue. When the person is absent, there may be no motion, i.e. the sleep motion may be NIL or zero.

Clause 2. The method/device/system/software of the radio-based sleep tracking system of clause 1, further comprising: identifying the N2 largest component-wise analytics by one of the following: (a) thresholding the N1 component-wise analytics based on a threshold; or (b) sorting N1 component-wise analytics to find the N2 largest component-wise analytics.

Clause 3. The method/device/system/software of the radio-based sleep tracking system of clause 1, further comprising: computing a time series of the first motion statistics, each first motion statistics associated with a time stamp; computing a set of potential body-motion-during sleep (BMS), each potential BMS (PBMS) being a local maximum point or a local peak of the time series of first motion statistics; monitoring the sleeping motion of the object based on the set of PBMS.

Clause 4. The method/device/system/software of the radio-based sleep tracking system of clause 3, further comprising: performing a BMS test on a PBMS and the time series of first motion statistics, removing a PBMS from the set of PBMS if the PBMS fails the BMS test.

Clause 5. The method/device/system/software of the radio-based sleep tracking system of clause 4, further comprising: performing the BMS test based on a magnitude feature of the PBMS, wherein the PBMS fails the BMS test if the local peak of the first motion statistics associated of the PBMS has the magnitude feature less than a threshold.

Clause 6. The method/device/system/software of the radio-based sleep tracking system of clause 5, further comprising: computing the threshold adaptively based on at least one of: a weighted mean of the magnitude feature of a number of largest first motion statistics in a period of time and a predefined quantity.

Clause 7. The method/device/system/software of the radio-based sleep tracking system of clause 4, further comprising: performing the BMS test based on a width measure associated with the PBMS, wherein the PBMS fails the BMS test if the width measure is larger than a threshold.

Clause 8. The method/device/system/software of the radio-based sleep tracking system of clause 7, further comprising: computing a left minimum point which is the nearest minimum point to the left of PBMS in the time series of first motion statistics; computing a right minimum point which is the nearest minimum point to the right of PBMS in the time series of first motion statistics; computing the width measure as a time difference between the left minimum point and the right minimum point.

Clause 9. The method/device/system/software of the radio-based sleep tracking system of clause 7, further comprising: computing a left drop point which is a nearest point to the left of PBMS in the time series of first motion statistics when the first motion statistics has a magnitude feature below a first target value; computing a right drop point which is a nearest point to the right of PBMS in the time series of first motion statistics when the first motion statistics has a magnitude feature below a second target value; computing the width measure as a time difference between the left drop point and the right drop point.

Clause 10. The method/device/system/software of the radio-based sleep tracking system of clause 9: wherein at least one of: the first target value and the second target value is one of the following: a predefined threshold, or an adaptive threshold based on a peak magnitude feature of the first motion statistics at the PBMS.

Clause 11. The method/device/system/software of the radio-based sleep tracking system of clause 10: wherein the adaptive threshold is one of: a difference of the peak magnitude feature and a predefined quantity, or a fraction of the peak magnitude feature.

Clause 12. The method/device/system/software of the radio-based sleep tracking system of clause 4, further comprising: performing the BMS test based on a height measure associated with the PBMS, wherein the PBMS fails the BMS test if the height measure is less than a threshold.

Clause 13. The method/device/system/software of the radio-based sleep tracking system of clause 12, further comprising: computing at least one of: a left minimum or a right minimum, wherein the left minimum point is a first adjacent minimum point to the left of the PBMS in the time series of first motion statistics, wherein the right minimum point is a first adjacent minimum point to the right of the PBMS in the time series of first motion statistics; computing the height measure based on at least one of: a difference of a magnitude feature of the first motion statistics between the PBMS and the left minimum point, a difference of the magnitude feature of the first motion statistics between the PBMS and the right minimum point, a quotient of another magnitude feature of the first motion statistics between the PBMS and the left minimum point, a quotient of the another magnitude feature of the first motion statistics between the PBMS and the right minimum point.

Clause 14. The method/device/system/software of the radio-based sleep tracking system of clause 12, further comprising: computing a left drop point which is a point to the left of PBMS in the time series of first motion statistics at a first time difference from the PBMS; computing a right drop point which is a point to the right of PBMS in the time series of first motion statistics at a second time difference from the PBMS; computing the height measure based on at least one of: a difference of a magnitude feature of the first motion statistics between the PBMS and the left drop point, a difference of the magnitude feature of the first motion statistics between the PBMS and the right drop point, a quotient of another magnitude feature of the left drop point and the PBMS, or a quotient of the another magnitude feature of the right drop point and the PBMS.

Clause 15. The method/device/system/software of the radio-based sleep tracking system of clause 4, further comprising: computing a width measure and a height measure associated with the PBMS; computing a prominence measure based on an increasing function of the height measure and a decreasing function of the width measure, wherein the PBMS fails the BMS test if the prominence measure is less than a threshold.

Clause 16. The method/device/system/software of the radio-based sleep tracking system of clause 15, further comprising: computing the prominence measure based on at least one of: a quotient, a difference or a comparison of the height measure and the width measure.

Clause 17. The method/device/system/software of the radio-based sleep tracking system of clause 4, further comprising: computing a left drop point which is a point to the left of PBMS in the time series of first motion statistics at a first time difference from the PBMS; computing a left boundary point which is a point to the left of PBMS in the time series of first motion statistics at a second time difference from the PBMS; computing a right drop point which is a point to the right of PBMS in the time series of first motion statistics at a third time difference from the PBMS; computing a right boundary point which is a point to the right of PBMS in the time series of first motion statistics at a fourth time difference from the PBMS; performing the BMS test based on a neighborhood dominance measure computed based on the left drop point, the left boundary point, the right drop point and the right boundary point, wherein the PBMS fails the BMS test if the neighborhood dominance measure is larger than a threshold.

Clause 18. The method/device/system/software of the radio-based sleep tracking system of clause 17, further comprising: computing the neighborhood dominance measure based on at least one of: a maximum of a magnitude feature of the first motion statistics between the left drop point and the left boundary point, a maximum of the magnitude feature of the first motion statistics between the right drop point and the right boundary point, a percentile point of the magnitude feature of the first motion statistics between the left drop point and the left boundary point, a percentile point of the magnitude feature of the first motion statistics between the right drop point and the right boundary point, a weighted average of a number of percentile points of the magnitude feature of the first motion statistics between the left drop point and the left boundary point, a weighted average of a number of percentile points of the magnitude feature of the first motion statistics between the right drop point and the right boundary point.

Clause 19. The method/device/system/software of the radio-based sleep tracking system of clause 17: wherein at least one of the following is true: the second time difference is equal to the fourth time difference, the first time difference is equal to the third time difference, both the first time difference and the third time different are predefined quantities, both the second time difference and the fourth time different are predefined quantities, the left drop point is the nearest minimum point to the left of PBMS in the time series of first motion statistics, the right drop point is the nearest minimum point to the right of PBMS in the time series of first motion statistics, the left boundary point is the nearest minimum point to the left of PBMS in a time series of lowpass-filtered first motion statistics, the right boundary point is the nearest minimum point to the right of PBMS in the time series of lowpass-filtered first motion statistics.

Clause 20. The method/device/system/software of the radio-based sleep tracking system of clause 4, further comprising: detecting a presence of the object in a time period around the PBMS based on the first motion statistics in the time period; performing the BMS test based on the presence detection of the object, wherein the PBMS fails the BMS test if presence of the object is not detected in the time period.

Clause 21. The method/device/system/software of the radio-based sleep tracking system of clause 20, further comprising: detecting a motion of the object at each time in the time period based on the first motion statistics; wherein the presence of the object is detected in the time period if the motion of the object is detected at any time during the time period.

Clause 22. The method/device/system/software of the radio-based sleep tracking system of clause 21: wherein the motion of the object is detected at a time if the first motion statistics at that time is larger than a first threshold or a second motion statistics at that time computed based on the TSCI is larger than a second threshold.

Clause 23. The method/device/system/software of the radio-based sleep tracking system of clause 22: for either of the first or second motion statistics, computing the respective threshold based on at least one of: a filtering of the time series of the motion statistics, a weighted averaging of the motion statistics, a minimization after the filtering, a minimization after the weighted averaging, a particular sliding time window associated with at least one of: the minimization after the filtering, or the minimization after the weighted averaging, a maximum of the motion statistics in the particular sliding time window.

Clause 24. The method/device/system/software of the radio-based sleep tracking system of clause 4, further comprising: detecting a non-sleeping activity of the object in a time period around the PBMS based on the first motion statistics in the time period; performing the BMS test based on the non-sleeping activity detection of the object, wherein the PBMS fails the BMS test if non-sleeping activity of the object is detected in the time period.

Clause 25. The method/device/system/software of the radio-based sleep tracking system of clause 24, further comprising: detecting a motion of the object at each time in the time period based on the first motion statistics, wherein the motion of the object is detected at a time if the first motion statistics at that time is larger than a first threshold or a second motion statistics at that time computed based on the TSCI is larger than a second threshold; computing a percentage of time in the time period at which the motion of the object is detected, wherein the non-sleeping activity of the object is detected in the time period if the percentage is larger than a threshold.

Clause 26. The method/device/system/software of the radio-based sleep tracking system of clause 4, further comprising: performing the BMS test based on a time difference between the PBMS and an immediate past PBMS, wherein the PBMS fails the BMS test if the time difference is less than a threshold.

Clause 27. The method/device/system/software of the radio-based sleep tracking system of clause 4, further comprising: performing the BMS test based on a time difference between the PBMS and a neighboring PBMS, merging the PBMS and the neighboring PBMS if the time difference is less than a threshold.

Clause 28. The method/device/system/software of the radio-based sleep tracking system of clause 4, further comprising: computing a time series of sleep likelihood (TSSL) for a period of time, each sleep likelihood (SL) associated with a time, wherein each SL is computed based on a motion intensity at the time and a count of PBMS in a time period associated with the time; computing a time series of sleep indicator (TSSI) for the period of time, each sleep indicator (SI) based on a comparison of the respective SL with a threshold, monitoring the sleep motion of the object based on the TSSL and the TSSI.

Clause 29. The method/device/system/software of the radio-based sleep tracking system of clause 28, further comprising: computing a time series of testing score (TS) for the period of time, each TS based on the SL, the SI and a penalty for large motion intensity; partitioning the period of time into a number of non-overlapping time units; computing a sum of test scores for each time unit; among the time units, identifying a time unit with the largest sum of test scores and initializing a sleep period as the time unit and a total testing score (TTS) as the associated largest sum of test scores; iteratively expanding the sleep period by adding an adjoining incremental time window either to the right or to the left of the sleep period and updating the TTS by adding the TS associated with the increment time window to TTS; in each iteration, adding a penalty to the TTS if the sleep period has a duration approaching or exceeding a typical sleep duration of the object; stopping the iteration based on a stopping criterion; monitoring the sleeping motion of the object based on the sleep period, the TTS, and the TS, the PBMS and the first motion statistics in the sleep period.

Clause 30. The method/device/system/software of the radio-based sleep tracking system of clause 29, further comprising: computing a sleep analytics based on the sleep period, the TTS, and the TS, the PBMS and the first motion statistics in the sleep period, wherein the sleep analytics comprises at least one of: a sleep starting time, a beginning time of the sleep period, a sleep waking-up time, an ending time of the sleep period, a sleep duration, a total duration of the sleep period, an amount of interruption during sleep, a count of non-sleep activities during the sleep period, a count of toilet visits during sleep period, a total duration of interrupts during sleep, a total time duration of non-sleep activities during the sleep period, a total time duration of toilet visits during the sleep period, an amount of body motion, a count of PBMS during the sleep period, an amount of awake time during sleep, a duration of awake time during sleep, a sleep score, a sleep quality score, a motion factor, a motion wakeness, a percentage of time or an amount of time that a first motion analytics, a second motion analytics computed based on the TSCI, a SL, a SI, a TS, a derivative or an integration is greater than a threshold during the sleep period, a percentage of time or an amount of time that a first motion analytics, a second motion analytics, a SL, a SI, a TS, a derivative or an integration is less than a threshold.

Clause 31. The method/device/system/software of the radio-based sleep tracking system of clause 1, comprising: wherein each of the N1 component-wise analytics is a pair-wise analytics based on a pair of CI of the TCSI; computing each of the N1 component-wise analytics based on the respective components of the pair of CI of the TSCI.

Clause 32. The method/device/system/software of the radio-based sleep tracking system of clause 31, comprising: computing each component-wise analytics based on a multiplication of the respective components of the pair of CI.

Clause 33. The method/device/system/software of the radio-based sleep tracking system of clause 32, comprising: wherein each component-wise analytics is an estimate of a component-wise correlation of the respective components of the pair of CI.

Clause 34. The method/device/system/software of the radio-based sleep tracking system of clause 31, comprising: wherein each of the N1 component-wise analytics is a pairwise analytics based on multiple pairs of CI of the TCSI; computing each of the N1 component-wise analytics based on the multiple pairs of CI.

Clause 35. The method/device/system/software of the radio-based sleep tracking system of clause 34, comprising: computing each component-wise analytics based on a weighted average of a number of multiplicative product of the respective components of each of the multiple pairs of CI.

Clause 36. The method/device/system/software of the radio-based sleep tracking system of clause 35, comprising: wherein all of the multiple pairs of CI have a common time difference between the pair of CI; wherein each component-wise analytics is an estimate of a component-wise correlation of the respective components of the pair of CI associated with the common time difference.

Clause 37. The method/device/system/software of the radio-based sleep tracking system of clause 34, comprising: wherein the multiple pairs of CI are consecutive or adjacent in time.

Clause 38. The method/device/system/software of the radio-based sleep tracking system of clause 1, further comprising: computing a time series of the first motion statistics; computing a baseline value of the first motion statistics in a period of time based on the first motion statistics of the time series in the period of time; subtracting the baseline value from each first motion statistics in the period of time.

Clause 39. The method/device/system/software of the radio-based sleep tracking system of clause 38, further comprising: wherein there are more than one periods of time; computing more than one of the baseline value of the first motion statistics, one for each period of time; computing an aggregated baseline value associated with a particular time period based on an aggregation of the more than one baseline values; subtracting the aggregated baseline value from each first motion statistics in the particular period of time.

The features described above may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., C, Java), including compiled or interpreted languages, and it may be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

While the present teaching contains many specific implementation details, these should not be construed as limitations on the scope of the present teaching or of what may be claimed, but rather as descriptions of features specific to particular embodiments of the present teaching. Certain features that are described in this specification in the context of separate embodiments may also be implemented in combination in a single embodiment. Conversely, various features that are described in the context of a single embodiment may also be implemented in multiple embodiments separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Particular embodiments of the subject matter have been described. Any combination of the features and architectures described above is intended to be within the scope of the following claims. Other embodiments are also within the scope of the following claims. In some cases, the actions recited in the claims may be performed in a different order and still achieve desirable results. In addition, the processes depicted in the accompanying figures do not necessarily require the particular order shown, or sequential order, to achieve desirable results. In certain implementations, multitasking and parallel processing may be advantageous.

We claim:
1. A system for radio-based sleep tracking, comprising:
a transmitter configured to transmit a first wireless signal through a wireless multipath channel in a venue;
a receiver configured to receive a second wireless signal through the wireless multipath channel, wherein the second wireless signal differs from the first wireless signal due to the wireless multipath channel which is impacted by a sleeping motion of an object in the venue; and
a processor configured for:
obtaining a time series of channel information (TSCI) of the wireless multipath channel based on the second wireless signal, wherein each channel information (CI) of the TSCI comprises N1 components, wherein N1 is a positive integer larger than one,
computing N1 component-wise analytics each associated with one of the N1 components of the TSCI, wherein each of the N1 component-wise analytics is a pair-wise analytics computed based on a pair of CI of the TSCI,
identifying N2 largest component-wise analytics among the N1 component-wise analytics, wherein N2 is a positive integer less than N1,
computing a time series of first motion statistics based on the N2 largest component-wise analytics of the TSCI, computing a set of potential body-motion-during sleep (BMS), each potential BMS (PBMS) being a local maximum point or a local peak of the time series of first motion statistics, performing at least one BMS test on each PBMS in the set of PBMS and the time series of first motion statistics, wherein the at least one BMS test comprises a first BMS test that is performed based on a width measure associated with each PBMS, removing a PBMS from the set of PBMS when the PBMS fails any BMS test, wherein the PBMS fails the first BMS test when the width measure is larger than a first threshold, and monitoring the sleeping motion of the object based on the time series of first motion statistics and the set of PBMS.

2. The system of claim 1, wherein the N2 largest component-wise analytics are identified by one of the following:

comparing each of the N1 component-wise analytics to a threshold to obtain the N2 largest component-wise analytics; or sorting the N1 component-wise analytics to find the N2 largest component-wise analytics.

3. The system of claim 1, wherein:

the at least one BMS test further comprises a second BMS test that is performed based on a magnitude feature of each PBMS, wherein the PBMS fails the second BMS test when the local peak of a first motion statistics associated of the PBMS has the magnitude feature less than a second threshold; and the second threshold is computed adaptively based on at least one of: a weighted mean of the magnitude feature of a number of largest first motion statistics in a period of time and a predefined quantity.

4. The system of claim 1, wherein the width measure is computed based on:

computing a left drop point which is a nearest point to the left of PBMS in the time series of first motion statistics when the first motion statistics has a magnitude feature below a first target value;

computing a right drop point which is a nearest point to the right of PBMS in the time series of first motion statistics when the first motion statistics has a magnitude feature below a second target value; and computing the width measure as a time difference between the left drop point and the right drop point.

5. The system of claim 4, wherein at least one of the first target value or the second target value is an adaptive threshold based on a peak magnitude feature of the first motion statistics at the PBMS.

6. The system of claim 5, wherein:

a third BMS test is performed based on a height measure associated with each PBMS, wherein the PBMS fails the third BMS test when the height measure is less than a third threshold.

7. The system of claim 6, wherein the height measure is computed based on:

computing at least one of: a left minimum point or a right minimum point, wherein the left minimum point is a first adjacent minimum point to the left of the PBMS in the time series of first motion statistics, wherein the right minimum point is a first adjacent minimum point to the right of the PBMS in the time series of first motion statistics; and computing the height measure based on at least one of:

a difference of a first magnitude feature of the first motion statistics between the PBMS and the left minimum point, a difference of the first magnitude feature of the first motion statistics between the PBMS and the right minimum point, a quotient of a second magnitude feature of the first motion statistics between the PBMS and the left minimum point, a quotient of the second magnitude feature of the first motion statistics between the PBMS and the right minimum point.

8. The system of claim 7, wherein the processor is further configured for:

computing a prominence measure based on an increasing function of the height measure and a decreasing function of the width measure, wherein the PBMS fails a fourth BMS test when the prominence measure is less than a fourth threshold.

9. The system of claim 8, wherein the processor is further configured for:

computing a left dropping point which is a point to the left of PBMS in the time series of first motion statistics at a first time difference from the PBMS;

computing a left boundary point which is a point to the left of PBMS in the time series of first motion statistics at a second time difference from the PBMS;

computing a right dropping point which is a point to the right of PBMS in the time series of first motion statistics at a third time difference from the PBMS;

computing a right boundary point which is a point to the right of PBMS in the time series of first motion statistics at a fourth time difference from the PBMS; and performing a fifth BMS test based on a neighborhood dominance measure computed based on the left dropping point, the left boundary point, the right dropping point and the right boundary point, wherein the PBMS fails the fifth BMS test when the neighborhood dominance measure is larger than a fifth threshold.

10. The system of claim 9, wherein the processor is further configured for:

detecting a presence of the object in a time period around the PBMS based on a first motion statistics in the time period; and performing a sixth BMS test based on the detecting, wherein the PBMS fails the sixth BMS test when presence of the object is not detected in the time period.

11. The system of claim 10, wherein the processor is further configured for:

detecting a motion of the object at each time in the time period based on the first motion statistics, wherein the presence of the object is detected in the time period when the motion of the object is detected at any time during the time period, wherein the motion of the object is detected at a time when the first motion statistics at that time is larger than a sixth threshold or a second motion statistics at that time computed based on the TSCI is larger than a seventh threshold.

12. The system of claim 11, wherein the processor is further configured for:

detecting a non-sleeping activity of the object in a time period around the PBMS based on the first motion statistics in the time period, wherein the non-sleeping activity of the object is detected in the time period when a percentage of time in the time period at which the motion of the object is detected is larger than an eighth threshold; and performing a seventh BMS test based on the non-sleeping activity detection of the object, wherein the PBMS fails the seventh BMS test when non-sleeping activity of the object is detected in the time period.

13. The system of claim 12, wherein the processor is further configured for:

performing an eighth BMS test based on a time difference between the PBMS and a neighboring PBMS, wherein the PBMS fails the eighth BMS test when the time difference is less than a ninth threshold; and merging the PBMS and the neighboring PBMS when the time difference is less than a tenth threshold.

14. The system of claim 13, wherein the processor is further configured for:

computing a time series of sleep likelihood (TSSL) for a period of time, each sleep likelihood (SL) associated with a time, wherein each SL is computed based on a motion intensity at the time and a count of PBMS in a period of time associated with the time;

computing a time series of sleep indicator (TSSI) for the period of time, each sleep indicator (SI) is computed based on a comparison of a respective SL with a threshold; and monitoring the sleep motion of the object based on the TSSL and the TSSI.

15. The system of claim 14, wherein the processor is further configured for:

computing a time series of testing score (TS) for the period of time, each TS based on the SL, the SI and a penalty for large motion intensity;

partitioning the period of time into a number of non-overlapping time units;

computing a sum of test scores for each time unit;

among the non-overlapping time units, identifying a time unit with the largest sum of test scores, initializing a sleep period as the time unit, and initializing a total testing score (TTS) as the associated largest sum of test scores;

iteratively expanding the sleep period by adding an adjoining incremental time window either to the right or to the left of the sleep period and iteratively updating the TTS by adding the TS associated with the increment time window to TTS;

in each iteration, adding a penalty to the TTS when the sleep period has a duration approaching or exceeding a typical sleep duration of the object;

stopping the iteration based on a stopping criterion; and monitoring the sleeping motion of the object based on the sleep period, the TTS, the TS, the PBMS and the first motion statistics in the sleep period.

16. The system of claim 15, wherein the processor is further configured for:

computing a sleep analytics based on the sleep period, the TTS, the TS, the PBMS and the first motion statistics in the sleep period.

17. The system of claim 16, wherein:

each of the N1 component-wise analytics is computed based on respective components of the pair of CI of the TSCI.

18. The system of claim 17, wherein the processor is further configured for:

computing each component-wise analytics based on a multiplication of the respective components of the pair of CI.

19. The system of claim 18, wherein:

each component-wise analytics is an estimate of a component-wise correlation of the respective components of the pair of CI.

20. The system of claim 19, wherein:

each of the N1 component-wise analytics is a pair-wise analytics based on multiple pairs of CI of the TCSI; and each of the N1 component-wise analytics is computed based on the multiple pairs of CI.

21. The system of claim 20, wherein the processor is further configured for:

computing each component-wise analytics based on a weighted average of a number of multiplicative product of the respective components of each of the multiple pairs of CI.

22. The system of claim 21, wherein:

all of the multiple pairs of CI have a common time difference between the pair of CI;

each component-wise analytics is an estimate of a component-wise correlation of the respective components of the pair of CI associated with the common time difference; and the multiple pairs of CI are consecutive or adjacent in time.

23. The system of claim 22, wherein the processor is further configured for:

computing a baseline value for a first time period based on the time series of first motion statistics in the first time period; and subtracting the baseline value from each first motion statistics in the first time period.

24. The system of claim 23, wherein the processor is further configured for:

computing a plurality of baseline values, each of which is computed for a corresponding time period;

computing an aggregated baseline value associated with a particular time period based on an aggregation of the plurality of baseline values; and subtracting the aggregated baseline value from each first motion statistics in the particular time period.

25. A wireless device of a system for radio-based sleep tracking, comprising:

a processor;

a memory communicatively coupled to the processor; and a receiver communicatively coupled to the processor, wherein:

an additional wireless device of the system is configured to transmit a first wireless signal through a wireless multipath channel in a venue, the receiver is configured to receive a second wireless signal through the wireless multipath channel, the second wireless signal differs from the first wireless signal due to the wireless multipath channel which is impacted by a sleeping motion of an object in the venue, and the processor is configured for:

obtaining a time series of channel information (TSCI) of the wireless multipath channel based on the second wireless signal, wherein each channel information (CI) of the TSCI comprises N1 components, wherein N1 is a positive integer larger than one, computing N1 component-wise analytics each associated with one of the N1 components of the TSCI, wherein each of the N1 component-wise analytics is a pair-wise analytics computed based on a pair of CI of the TSCI, identifying N2 largest component-wise analytics among the N1 component-wise analytics, wherein N2 is a positive integer less than N1, computing a time series of first motion statistics based on the N2 largest component-wise analytics of the TSCI, computing a set of potential body-motion-during sleep (BMS), each potential BMS (PBMS) being a local maximum point or a local peak of the time series of first motion statistics, performing at least one BMS test on each PBMS in the set of PBMS and the time series of first motion statistics, wherein the at least one BMS test comprises a first BMS test that is performed based on a width measure associated with each PBMS, removing a PBMS from the set of PBMS when the PBMS fails any BMS test, wherein the PBMS fails the first BMS test when the width measure is larger than a first threshold, and monitoring the sleeping motion of the object based on the time series of first motion statistics and the set of PBMS.

26. A method for radio-based sleep tracking, comprising:

transmitting a first wireless signal through a wireless multipath channel in a venue;

receiving a second wireless signal through the wireless multipath channel, wherein the second wireless signal differs from the first wireless signal due to the wireless multipath channel which is impacted by a sleeping motion of an object in the venue;

obtaining a time series of channel information (TSCI) of the wireless multipath channel based on the second wireless signal, wherein each channel information (CI) of the TSCI comprises N1 components, wherein N1 is a positive integer larger than one;

computing N1 component-wise analytics each associated with one of the N1 components of the TSCI, wherein each of the N1 component-wise analytics is a pair-wise analytics computed based on a pair of CI of the TSCI;

identifying N2 largest component-wise analytics among the N1 component-wise analytics, wherein N2 is a positive integer less than N1;

computing a time series of first motion statistics based on the N2 largest component-wise analytics of the TSCI;

computing a set of potential body-motion-during sleep (BMS), each potential BMS (PBMS) being a local maximum point or a local peak of the time series of first motion statistics;

performing at least one BMS test on each PBMS in the set of PBMS and the time series of first motion statistics, wherein the at least one BMS test comprises a first BMS test that is performed based on a width measure associated with each PBMS;

removing a PBMS from the set of PBMS when the PBMS fails any BMS test, wherein the PBMS fails the first BMS test when the width measure is larger than a first threshold; and monitoring the sleeping motion of the object based on the time series of first motion statistics and the set of PBMS.

\* \* \* \* \*